United States Patent
Otsuji et al.

(10) Patent No.: US 12,018,276 B2
(45) Date of Patent: Jun. 25, 2024

(54) LYMPHOCYTE PRODUCTION METHOD

(71) Applicant: TAKARA BIO INC., Shiga (JP)

(72) Inventors: Tomomi Otsuji, Kusatsu (JP); Yuka Hirase, Kusatsu (JP); Asako Hatsuyama, Kusatsu (JP); Sachiko Okamoto, Kusatsu (JP); Tatsuji Enoki, Kusatsu (JP); Junichi Mineno, Kusatsu (JP)

(73) Assignee: TAKARA BIO INC., Shiga (JP)

( * ) Notice: Subject to any disclaimer, the term of this patent is extended or adjusted under 35 U.S.C. 154(b) by 397 days.

(21) Appl. No.: 16/961,773

(22) PCT Filed: Jan. 24, 2019

(86) PCT No.: PCT/JP2019/002202
§ 371 (c)(1),
(2) Date: Jul. 13, 2020

(87) PCT Pub. No.: WO2019/146673
PCT Pub. Date: Aug. 1, 2019

(65) Prior Publication Data
US 2021/0062141 A1 Mar. 4, 2021

(30) Foreign Application Priority Data
Jan. 25, 2018 (JP) ................. 2018-010494

(51) Int. Cl.
*C12N 5/00* (2006.01)
*C07K 14/78* (2006.01)
*C12N 5/078* (2010.01)

(52) U.S. Cl.
CPC ............ *C12N 5/0068* (2013.01); *C07K 14/78* (2013.01); *C12N 5/0634* (2013.01); *C12N 2533/50* (2013.01); *C12N 2533/52* (2013.01)

(58) Field of Classification Search
CPC .............. C12N 5/0068; C12N 2533/50; C12N 2533/52; C12N 5/0634; C07K 14/78
See application file for complete search history.

(56) References Cited

U.S. PATENT DOCUMENTS

| | | |
|---|---|---|
| 8,216,837 B2 | 7/2012 | Muraki et al. |
| 8,765,469 B2 | 7/2014 | Marui et al. |
| 8,927,273 B2 | 1/2015 | Ideno et al. |
| 9,062,287 B2 * | 6/2015 | Ideno ............. A61P 31/10 |
| 2009/0221077 A1 | 9/2009 | Ideno et al. |
| 2010/0150886 A1 | 6/2010 | Marui et al. |
| 2010/0255578 A1 | 10/2010 | Muraki et al. |
| 2021/0254018 A1 * | 8/2021 | Otsuji ............. A61K 38/39 |

FOREIGN PATENT DOCUMENTS

| | | | |
|---|---|---|---|
| EP | 1 916 302 | 4/2008 | |
| EP | 2 305 793 | 4/2011 | |
| EP | 3 492 592 | 6/2019 | |
| WO | 2005/019450 | 3/2005 | |
| WO | 2007/020880 | 2/2007 | |
| WO | WO-2007044396 A2 * | 4/2007 | ............ A61K 45/06 |
| WO | 2007/142300 | 12/2007 | |
| WO | WO-2017035577 A1 * | 3/2017 | ............ A61L 27/54 |
| WO | 2018/021543 | 2/2018 | |

OTHER PUBLICATIONS

To, W. S., & Midwood, K. S. (2011). Plasma and cellular fibronectin: distinct and independent functions during tissue repair. Fibrogenesis & tissue repair, 4, 1-17. (Year: 2011).*
Davis et al. Fibronectin promotes proliferation of naive and memory T cells by signaling through both the VLA-4 and VLA-5 integrin molecules. Journal of Immunology 1990, 145;3:785-793. (Year: 1990).*
Extended European Search Report dated Oct. 27, 2021 in corresponding European Patent Application No. 19744513.3, 8 pages.
Mizobata et al., "Fibronectin promotes the proliferation of cytotoxic T lymphocytes generated from cancer patients", British Journal of Cancer, 1996, vol. 74, No. 10, pp. 1598-1604, 7 pages.
Hosoi et al., "Stimulation through very late antigen-4 and -5 improves the multifunctionality and memory formation of CD8+ T cells", European Journal of Immunology, 2014, vol. 44, No. 6, pp. 1747-1758, 13 pages.
Office Action dated Jul. 19, 2022 in corresponding Japanese Patent Application No. 2019-567132, with English Translation, 14 pages.
International Search Report dated Apr. 23, 2019 in PCT Application No. PCT/JP2019/002202.
International Preliminary Report on Patentability dated Jul. 28, 2020 in PCT Application No. PCT/JP2019/002202.
Mizobata, "Basic research on culture method of cytotoxic T lymphocytes using solid phased Fibronectin and anti-CD3 antibody", The Journal of the Wakayama Medical Society, 1995, vol. 46, No. 4, pp. 457-467.
Cardarelli et al., "Fibronectin Augments Anti-CD3-Mediated IL-2 Receptor (CD25) Expression on Human Peripheral Blood Lymphocytes", Cellular Immunology, 1991, vol. 135, pp. 105-117.
Ideno et al., "Development of Novel Large-Scale T Cell Expansion Method in Combination with Immobilized Anti-CD3 Monoclonal Antibody and RetroNectin", Biotherapy, 2008, vol. 22, No. 5, pp. 297-302.
First Office Action including search report dated Feb. 17, 2023, in corresponding Chinese Patent Application No. 201980010078.2, with English translation, 15 pages.

* cited by examiner

*Primary Examiner* — Allison M Fox
*Assistant Examiner* — Jennifer S Spence
(74) *Attorney, Agent, or Firm* — Wenderoth, Lind & Ponack, L.L.P.

(57) ABSTRACT

In the present invention, lymphocytes are efficiently grown by culturing lymphocytes in the presence of a novel recombinant fibronectin fragment.

10 Claims, 2 Drawing Sheets
Specification includes a Sequence Listing.

[FIG. 1]
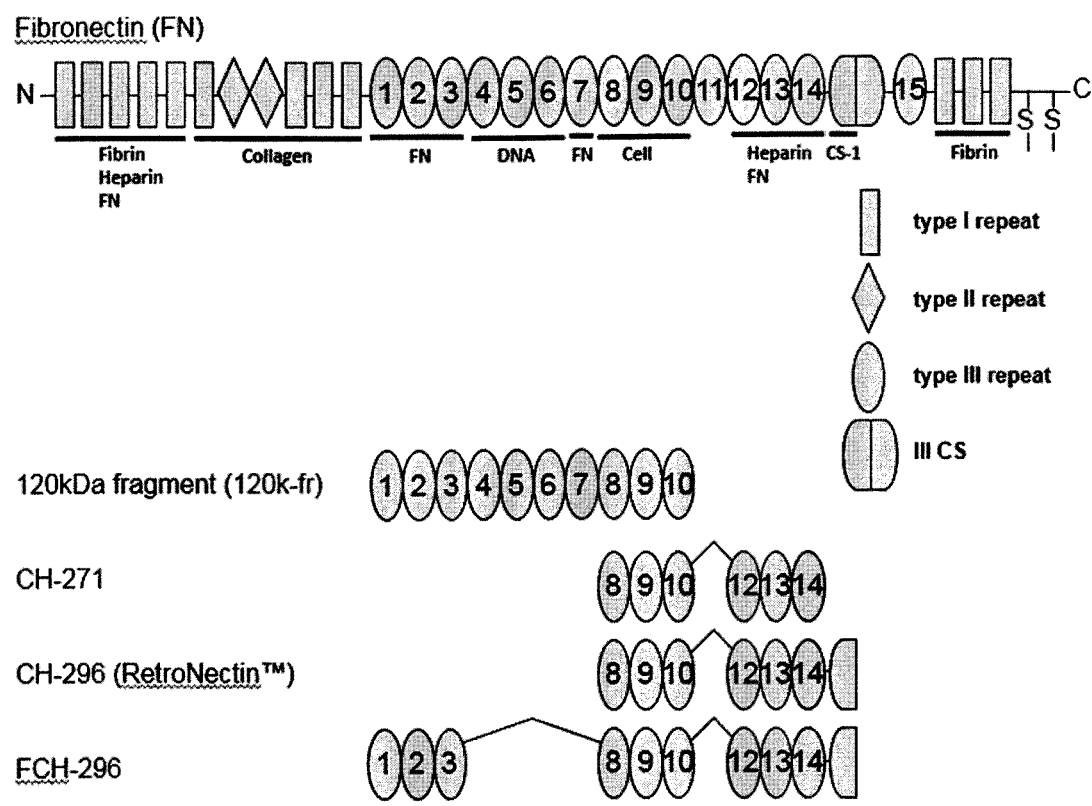

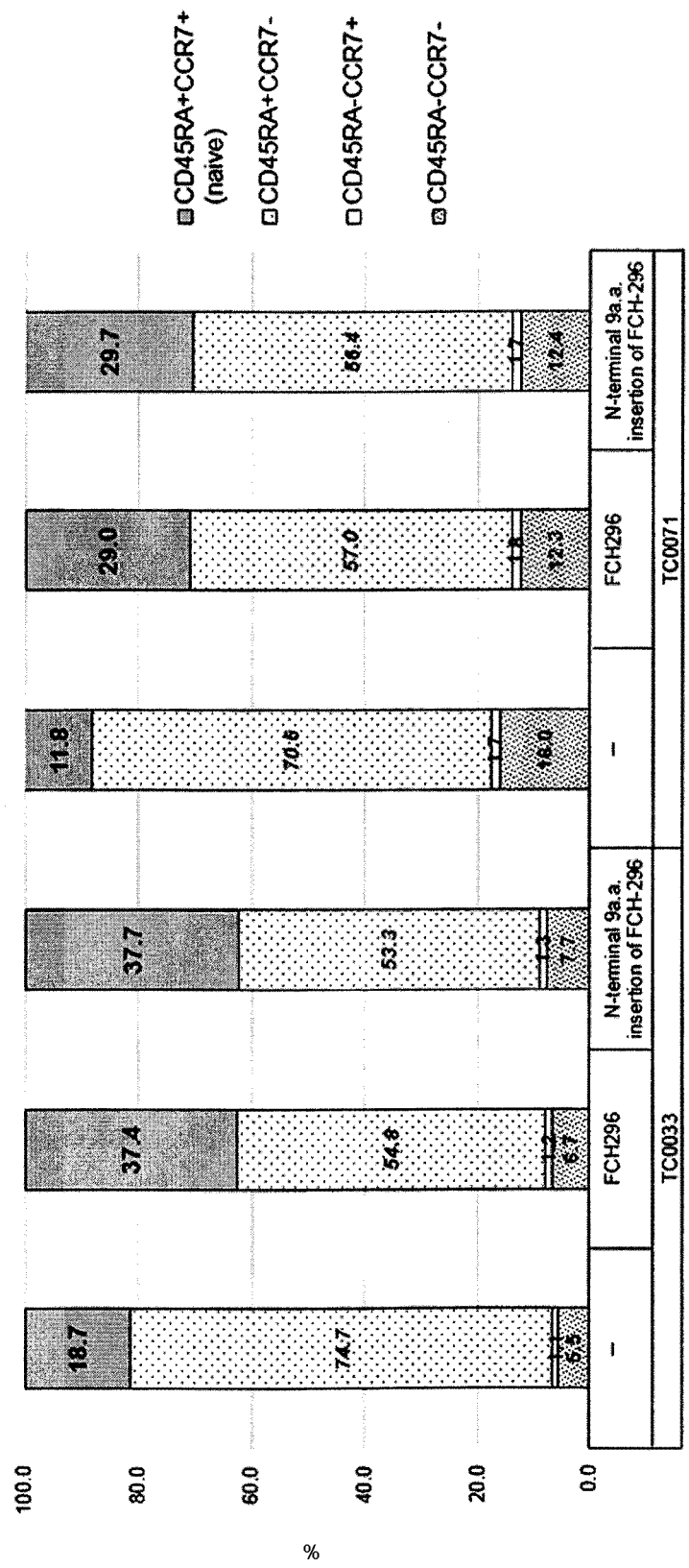
[Fig. 2]

SEQUENCE LISTING

```
<160> NUMBER OF SEQ ID NOS: 39

<210> SEQ ID NO 1
<211> LENGTH: 92
<212> TYPE: PRT
<213> ORGANISM: Artificial Sequence
<220> FEATURE:
<223> OTHER INFORMATION: Partial region of fibronectin named III-1

<400> SEQUENCE: 1

Ser Gly Pro Val Glu Val Phe Ile Thr Glu Thr Pro Ser Gln Pro Asn
```

```
1               5                   10                  15
Ser His Pro Ile Gln Trp Asn Ala Pro Gln Pro Ser His Ile Ser Lys
            20                  25                  30

Tyr Ile Leu Arg Trp Arg Pro Lys Asn Ser Val Gly Arg Trp Lys Glu
            35                  40                  45

Ala Thr Ile Pro Gly His Leu Asn Ser Tyr Thr Ile Lys Gly Leu Lys
            50                  55                  60

Pro Gly Val Val Tyr Glu Gly Gln Leu Ile Ser Ile Gln Gln Tyr Gly
65                  70                  75                  80

His Gln Glu Val Thr Arg Phe Asp Phe Thr Thr Thr
                    85                  90

<210> SEQ ID NO 2
<211> LENGTH: 91
<212> TYPE: PRT
<213> ORGANISM: Artificial Sequence
<220> FEATURE:
<223> OTHER INFORMATION: Partial region of fibronectin named III-2

<400> SEQUENCE: 2

Ser Pro Leu Val Ala Thr Ser Glu Ser Val Thr Glu Ile Thr Ala Ser
1               5                   10                  15

Ser Phe Val Val Ser Trp Val Ser Ala Ser Asp Thr Val Ser Gly Phe
            20                  25                  30

Arg Val Glu Tyr Glu Leu Ser Glu Gly Asp Glu Pro Gln Tyr Leu
            35                  40                  45

Asp Leu Pro Ser Thr Ala Thr Ser Val Asn Ile Pro Asp Leu Leu Pro
            50                  55                  60

Gly Arg Lys Tyr Ile Val Asn Val Tyr Gln Ile Ser Glu Asp Gly Glu
65                  70                  75                  80

Gln Ser Leu Ile Leu Ser Thr Ser Gln Thr Thr
                    85                  90

<210> SEQ ID NO 3
<211> LENGTH: 96
<212> TYPE: PRT
<213> ORGANISM: Artificial Sequence
<220> FEATURE:
<223> OTHER INFORMATION: Partial region of fibronectin named III-3

<400> SEQUENCE: 3

Ala Pro Asp Ala Pro Pro Asp Pro Thr Val Asp Gln Val Asp Asp Thr
1               5                   10                  15

Ser Ile Val Val Arg Trp Ser Arg Pro Gln Ala Pro Ile Thr Gly Tyr
            20                  25                  30

Arg Ile Val Tyr Ser Pro Ser Val Glu Gly Ser Ser Thr Glu Leu Asn
            35                  40                  45

Leu Pro Glu Thr Ala Asn Ser Val Thr Leu Ser Asp Leu Gln Pro Gly
            50                  55                  60

Val Gln Tyr Asn Ile Thr Ile Tyr Ala Val Glu Glu Asn Gln Glu Ser
65                  70                  75                  80

Thr Pro Val Val Ile Gln Gln Glu Thr Thr Gly Thr Pro Arg Ser Asp
                    85                  90                  95

<210> SEQ ID NO 4
<211> LENGTH: 90
<212> TYPE: PRT
<213> ORGANISM: Artificial Sequence
<220> FEATURE:
```

<223> OTHER INFORMATION: Partial region of fibronectin named III-4

<400> SEQUENCE: 4

Thr Val Pro Ser Pro Arg Asp Leu Gln Phe Val Glu Val Thr Asp Val
1               5                   10                  15

Lys Val Thr Ile Met Trp Thr Pro Pro Glu Ser Ala Val Thr Gly Tyr
            20                  25                  30

Arg Val Asp Val Ile Pro Val Asn Leu Pro Gly Glu His Gly Gln Arg
        35                  40                  45

Leu Pro Ile Ser Arg Asn Thr Phe Ala Glu Val Thr Gly Leu Ser Pro
    50                  55                  60

Gly Val Thr Tyr Tyr Phe Lys Val Phe Ala Val Ser His Gly Arg Glu
65                  70                  75                  80

Ser Lys Pro Leu Thr Ala Gln Gln Thr Thr
                85                  90

<210> SEQ ID NO 5
<211> LENGTH: 90
<212> TYPE: PRT
<213> ORGANISM: Artificial Sequence
<220> FEATURE:
<223> OTHER INFORMATION: Partial region of fibronectin named III-5

<400> SEQUENCE: 5

Lys Leu Asp Ala Pro Thr Asn Leu Gln Phe Val Asn Glu Thr Asp Ser
1               5                   10                  15

Thr Val Leu Val Arg Trp Thr Pro Pro Arg Ala Gln Ile Thr Gly Tyr
            20                  25                  30

Arg Leu Thr Val Gly Leu Thr Arg Arg Gly Gln Pro Arg Gln Tyr Asn
        35                  40                  45

Val Gly Pro Ser Val Ser Lys Tyr Pro Leu Arg Asn Leu Gln Pro Ala
    50                  55                  60

Ser Glu Tyr Thr Val Ser Leu Val Ala Ile Lys Gly Asn Gln Glu Ser
65                  70                  75                  80

Pro Lys Ala Thr Gly Val Phe Thr Thr Leu
                85                  90

<210> SEQ ID NO 6
<211> LENGTH: 87
<212> TYPE: PRT
<213> ORGANISM: Artificial Sequence
<220> FEATURE:
<223> OTHER INFORMATION: Partial region of fibronectin named III-6

<400> SEQUENCE: 6

Gln Pro Gly Ser Ser Ile Pro Pro Tyr Asn Thr Glu Val Thr Glu Thr
1               5                   10                  15

Thr Ile Val Ile Thr Trp Thr Pro Ala Pro Arg Ile Gly Phe Lys Leu
            20                  25                  30

Gly Val Arg Pro Ser Gln Gly Gly Glu Ala Pro Arg Glu Val Thr Ser
        35                  40                  45

Asp Ser Gly Ser Ile Val Val Ser Gly Leu Thr Pro Gly Val Glu Tyr
    50                  55                  60

Val Tyr Thr Ile Gln Val Leu Arg Asp Gly Gln Glu Arg Asp Ala Pro
65                  70                  75                  80

Ile Val Asn Lys Val Val Thr
                85

```
<210> SEQ ID NO 7
<211> LENGTH: 93
<212> TYPE: PRT
<213> ORGANISM: Artificial Sequence
<220> FEATURE:
<223> OTHER INFORMATION: Partial region of fibronectin named III-7

<400> SEQUENCE: 7

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Gly Tyr Arg Ile Thr Thr Thr Pro Thr Asn Gly Gln Gln Gly Asn Ser
        35                  40                  45

Leu Glu Glu Val Val His Ala Asp Gln Ser Ser Cys Thr Phe Asp Asn
    50                  55                  60

Leu Ser Pro Gly Leu Glu Tyr Asn Val Ser Val Tyr Thr Val Lys Asp
65                  70                  75                  80

Asp Lys Glu Ser Val Pro Ile Ser Asp Thr Ile Ile Pro
                85                  90

<210> SEQ ID NO 8
<211> LENGTH: 87
<212> TYPE: PRT
<213> ORGANISM: Artificial Sequence
<220> FEATURE:
<223> OTHER INFORMATION: Partial region of fibronectin named III-8

<400> SEQUENCE: 8

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
        35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr
                85

<210> SEQ ID NO 9
<211> LENGTH: 90
<212> TYPE: PRT
<213> ORGANISM: Artificial Sequence
<220> FEATURE:
<223> OTHER INFORMATION: Partial region of fibronectin named III-9

<400> SEQUENCE: 9

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80
```

```
Ser Pro Leu Leu Ile Gly Gln Gln Ser Thr
            85                  90
```

<210> SEQ ID NO 10
<211> LENGTH: 94
<212> TYPE: PRT
<213> ORGANISM: Artificial Sequence
<220> FEATURE:
<223> OTHER INFORMATION: Partial region of fibronectin named III-10

<400> SEQUENCE: 10

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
            85                  90
```

<210> SEQ ID NO 11
<211> LENGTH: 90
<212> TYPE: PRT
<213> ORGANISM: Artificial Sequence
<220> FEATURE:
<223> OTHER INFORMATION: Partial region of fibronectin named III-11

<400> SEQUENCE: 11

```
Glu Ile Asp Lys Pro Ser Gln Met Gln Val Thr Asp Val Gln Asp Asn
1               5                   10                  15

Ser Ile Ser Val Lys Trp Leu Pro Ser Ser Pro Val Thr Gly Tyr
            20                  25                  30

Arg Val Thr Thr Thr Pro Lys Asn Gly Pro Gly Pro Thr Lys Thr Lys
        35                  40                  45

Thr Ala Gly Pro Asp Gln Thr Glu Met Thr Ile Glu Gly Leu Gln Pro
    50                  55                  60

Thr Val Glu Tyr Val Val Ser Val Tyr Ala Gln Asn Pro Ser Gly Glu
65                  70                  75                  80

Ser Gln Pro Leu Val Gln Thr Ala Val Thr
            85                  90
```

<210> SEQ ID NO 12
<211> LENGTH: 92
<212> TYPE: PRT
<213> ORGANISM: Artificial Sequence
<220> FEATURE:
<223> OTHER INFORMATION: Partial region of fibronectin named III-12

<400> SEQUENCE: 12

```
Ala Ile Pro Ala Pro Thr Asp Leu Lys Phe Thr Gln Val Thr Pro Thr
1               5                   10                  15

Ser Leu Ser Ala Gln Trp Thr Pro Pro Asn Val Gln Leu Thr Gly Tyr
            20                  25                  30

Arg Val Arg Val Thr Pro Lys Glu Lys Thr Gly Pro Met Lys Glu Ile
        35                  40                  45
```

```
Asn Leu Ala Pro Asp Ser Ser Ser Val Val Ser Gly Leu Met Val
         50                  55                  60

Ala Thr Lys Tyr Glu Val Ser Val Tyr Ala Leu Lys Asp Thr Leu Thr
 65                  70                  75                  80

Ser Arg Pro Ala Gln Gly Val Val Thr Thr Leu Glu
                 85                  90

<210> SEQ ID NO 13
<211> LENGTH: 89
<212> TYPE: PRT
<213> ORGANISM: Artificial Sequence
<220> FEATURE:
<223> OTHER INFORMATION: Partial region of fibronectin named III-13

<400> SEQUENCE: 13

Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Gly Phe
                 20                  25                  30

Gln Val Asp Ala Val Pro Ala Asn Gly Gln Thr Pro Ile Gln Arg Thr
             35                  40                  45

Ile Lys Pro Asp Val Arg Ser Tyr Thr Ile Thr Gly Leu Gln Pro Gly
 50                  55                  60

Thr Asp Tyr Lys Ile Tyr Leu Tyr Thr Leu Asn Asp Asn Ala Arg Ser
 65                  70                  75                  80

Ser Pro Val Val Ile Asp Ala Ser Thr
                 85

<210> SEQ ID NO 14
<211> LENGTH: 90
<212> TYPE: PRT
<213> ORGANISM: Artificial Sequence
<220> FEATURE:
<223> OTHER INFORMATION: Partial region of fibronectin named III-14

<400> SEQUENCE: 14

Ala Ile Asp Ala Pro Ser Asn Leu Arg Phe Leu Ala Thr Thr Pro Asn
 1               5                  10                  15

Ser Leu Leu Val Ser Trp Gln Pro Pro Arg Ala Arg Ile Thr Gly Tyr
                 20                  25                  30

Ile Ile Lys Tyr Glu Lys Pro Gly Ser Pro Arg Glu Val Val Pro
             35                  40                  45

Arg Pro Arg Pro Gly Val Thr Glu Ala Thr Ile Thr Gly Leu Glu Pro
 50                  55                  60

Gly Thr Glu Tyr Thr Ile Tyr Val Ile Ala Leu Lys Asn Asn Gln Lys
 65                  70                  75                  80

Ser Glu Pro Leu Ile Gly Arg Lys Lys Thr
                 85                  90

<210> SEQ ID NO 15
<211> LENGTH: 25
<212> TYPE: PRT
<213> ORGANISM: Artificial Sequence
<220> FEATURE:
<223> OTHER INFORMATION: Partial region of fibronectin named CS-1

<400> SEQUENCE: 15

Asp Glu Leu Pro Gln Leu Val Thr Leu Pro His Pro Asn Leu His Gly
 1               5                  10                  15

Pro Glu Ile Leu Asp Val Pro Ser Thr
```

-continued

```
                20                  25

<210> SEQ ID NO 16
<211> LENGTH: 932
<212> TYPE: PRT
<213> ORGANISM: Artificial Sequence
<220> FEATURE:
<223> OTHER INFORMATION: Fibronectin fragment named 120k-fr

<400> SEQUENCE: 16

Ser Gly Pro Val Glu Val Phe Ile Thr Glu Thr Pro Ser Gln Pro Asn
1               5                   10                  15

Ser His Pro Ile Gln Trp Asn Ala Pro Gln Pro Ser His Ile Ser Lys
            20                  25                  30

Tyr Ile Leu Arg Trp Arg Pro Lys Asn Ser Val Gly Arg Trp Lys Glu
        35                  40                  45

Ala Thr Ile Pro Gly His Leu Asn Ser Tyr Thr Ile Lys Gly Leu Lys
    50                  55                  60

Pro Gly Val Val Tyr Glu Gly Gln Leu Ile Ser Ile Gln Gln Tyr Gly
65                  70                  75                  80

His Gln Glu Val Thr Arg Phe Asp Phe Thr Thr Thr Ser Thr Ser Thr
                85                  90                  95

Pro Val Thr Ser Asn Thr Val Thr Gly Glu Thr Thr Pro Phe Ser Pro
            100                 105                 110

Leu Val Ala Thr Ser Glu Ser Val Thr Glu Ile Thr Ala Ser Ser Phe
        115                 120                 125

Val Val Ser Trp Val Ser Ala Ser Asp Thr Val Ser Gly Phe Arg Val
    130                 135                 140

Glu Tyr Glu Leu Ser Glu Gly Asp Glu Pro Gln Tyr Leu Asp Leu
145                 150                 155                 160

Pro Ser Thr Ala Thr Ser Val Asn Ile Pro Asp Leu Leu Pro Gly Arg
                165                 170                 175

Lys Tyr Ile Val Asn Val Tyr Gln Ile Ser Glu Asp Gly Glu Gln Ser
            180                 185                 190

Leu Ile Leu Ser Thr Ser Gln Thr Thr Ala Pro Asp Ala Pro Pro Asp
        195                 200                 205

Pro Thr Val Asp Gln Val Asp Asp Thr Ser Ile Val Val Arg Trp Ser
    210                 215                 220

Arg Pro Gln Ala Pro Ile Thr Gly Tyr Arg Ile Val Tyr Ser Pro Ser
225                 230                 235                 240

Val Glu Gly Ser Ser Thr Glu Leu Asn Leu Pro Glu Thr Ala Asn Ser
                245                 250                 255

Val Thr Leu Ser Asp Leu Gln Pro Gly Val Gln Tyr Asn Ile Thr Ile
            260                 265                 270

Tyr Ala Val Glu Glu Asn Gln Glu Ser Thr Pro Val Val Ile Gln Gln
        275                 280                 285

Glu Thr Thr Gly Thr Pro Arg Ser Asp Thr Val Pro Ser Pro Arg Asp
    290                 295                 300

Leu Gln Phe Val Glu Val Thr Asp Val Lys Val Thr Ile Met Trp Thr
305                 310                 315                 320

Pro Pro Glu Ser Ala Val Thr Gly Tyr Arg Val Asp Val Ile Pro Val
                325                 330                 335

Asn Leu Pro Gly Glu His Gly Gln Arg Leu Pro Ile Ser Arg Asn Thr
            340                 345                 350

Phe Ala Glu Val Thr Gly Leu Ser Pro Gly Val Thr Tyr Tyr Phe Lys
```

```
            355                 360                 365
Val Phe Ala Val Ser His Gly Arg Glu Ser Lys Pro Leu Thr Ala Gln
            370                 375                 380
Gln Thr Thr Lys Leu Asp Ala Pro Thr Asn Leu Gln Phe Val Asn Glu
385                 390                 395                 400
Thr Asp Ser Thr Val Leu Val Arg Trp Thr Pro Pro Arg Ala Gln Ile
                405                 410                 415
Thr Gly Tyr Arg Leu Thr Val Gly Leu Thr Arg Arg Gly Gln Pro Arg
            420                 425                 430
Gln Tyr Asn Val Gly Pro Ser Val Ser Lys Tyr Pro Leu Arg Asn Leu
            435                 440                 445
Gln Pro Ala Ser Glu Tyr Thr Val Ser Leu Val Ala Ile Lys Gly Asn
            450                 455                 460
Gln Glu Ser Pro Lys Ala Thr Gly Val Phe Thr Thr Leu Gln Pro Gly
465                 470                 475                 480
Ser Ser Ile Pro Pro Tyr Asn Thr Glu Val Thr Glu Thr Thr Ile Val
                485                 490                 495
Ile Thr Trp Thr Pro Ala Pro Arg Ile Gly Phe Lys Leu Gly Val Arg
            500                 505                 510
Pro Ser Gln Gly Gly Glu Ala Pro Arg Glu Val Thr Ser Asp Ser Gly
            515                 520                 525
Ser Ile Val Val Ser Gly Leu Thr Pro Gly Val Glu Tyr Val Tyr Thr
            530                 535                 540
Ile Gln Val Leu Arg Asp Gly Gln Glu Arg Asp Ala Pro Ile Val Asn
545                 550                 555                 560
Lys Val Val Thr Pro Leu Ser Pro Pro Thr Asn Leu His Leu Glu Ala
                565                 570                 575
Asn Pro Asp Thr Gly Val Leu Thr Val Ser Trp Glu Arg Ser Thr Thr
            580                 585                 590
Pro Asp Ile Thr Gly Tyr Arg Ile Thr Thr Thr Pro Thr Asn Gly Gln
            595                 600                 605
Gln Gly Asn Ser Leu Glu Glu Val Val His Ala Asp Gln Ser Ser Cys
            610                 615                 620
Thr Phe Asp Asn Leu Ser Pro Gly Leu Glu Tyr Asn Val Ser Val Tyr
625                 630                 635                 640
Thr Val Lys Asp Asp Lys Glu Ser Val Pro Ile Ser Asp Thr Ile Ile
                645                 650                 655
Pro Ala Val Pro Pro Pro Thr Asp Leu Arg Phe Thr Asn Ile Gly Pro
            660                 665                 670
Asp Thr Met Arg Val Thr Trp Ala Pro Pro Pro Ser Ile Asp Leu Thr
            675                 680                 685
Asn Phe Leu Val Arg Tyr Ser Pro Val Lys Asn Glu Glu Asp Val Ala
            690                 695                 700
Glu Leu Ser Ile Ser Pro Ser Asp Asn Ala Val Val Leu Thr Asn Leu
705                 710                 715                 720
Leu Pro Gly Thr Glu Tyr Val Val Ser Val Ser Ser Val Tyr Glu Gln
                725                 730                 735
His Glu Ser Thr Pro Leu Arg Gly Arg Gln Lys Thr Gly Leu Asp Ser
            740                 745                 750
Pro Thr Gly Ile Asp Phe Ser Asp Ile Thr Ala Asn Ser Phe Thr Val
            755                 760                 765
His Trp Ile Ala Pro Arg Ala Thr Ile Thr Gly Tyr Arg Ile Arg His
            770                 775                 780
```

```
His Pro Glu His Phe Ser Gly Arg Pro Arg Glu Asp Arg Val Pro His
785                 790                 795                 800

Ser Arg Asn Ser Ile Thr Leu Thr Asn Leu Thr Pro Gly Thr Glu Tyr
            805                 810                 815

Val Val Ser Ile Val Ala Leu Asn Gly Arg Glu Glu Ser Pro Leu Leu
        820                 825                 830

Ile Gly Gln Gln Ser Thr Val Ser Asp Val Pro Arg Asp Leu Glu Val
            835                 840                 845

Val Ala Ala Thr Pro Thr Ser Leu Leu Ile Ser Trp Asp Ala Pro Ala
850                 855                 860

Val Thr Val Arg Tyr Tyr Arg Ile Thr Tyr Gly Glu Thr Gly Gly Asn
865                 870                 875                 880

Ser Pro Val Gln Glu Phe Thr Val Pro Gly Ser Lys Ser Thr Ala Thr
                885                 890                 895

Ile Ser Gly Leu Lys Pro Gly Val Asp Tyr Thr Ile Thr Val Tyr Ala
            900                 905                 910

Val Thr Gly Arg Gly Asp Ser Pro Ala Ser Ser Lys Pro Ile Ser Ile
        915                 920                 925

Asn Tyr Arg Thr
    930

<210> SEQ ID NO 17
<211> LENGTH: 549
<212> TYPE: PRT
<213> ORGANISM: Artificial Sequence
<220> FEATURE:
<223> OTHER INFORMATION: Fibronectin fragment named CH-271

<400> SEQUENCE: 17

Pro Thr Asp Leu Arg Phe Thr Asn Ile Gly Pro Asp Thr Met Arg Val
1               5                   10                  15

Thr Trp Ala Pro Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
        35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
            85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
            165                 170                 175

Thr Val Ser Asp Val Pro Arg Asp Leu Glu Val Val Ala Ala Thr Pro
        180                 185                 190

Thr Ser Leu Leu Ile Ser Trp Asp Ala Pro Ala Val Thr Val Arg Tyr
    195                 200                 205
```

-continued

Tyr Arg Ile Thr Tyr Gly Glu Thr Gly Gly Asn Ser Pro Val Gln Glu
            210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Ala Ile Pro Ala Pro Thr Asp Leu Lys Phe
        275                 280                 285

Thr Gln Val Thr Pro Thr Ser Leu Ser Ala Gln Trp Thr Pro Pro Asn
    290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
                325                 330                 335

Val Ser Gly Leu Met Val Ala Thr Lys Tyr Glu Val Ser Val Tyr Ala
            340                 345                 350

Leu Lys Asp Thr Leu Thr Ser Arg Pro Ala Gln Gly Val Val Thr Thr
        355                 360                 365

Leu Glu Asn Val Ser Pro Pro Arg Arg Ala Arg Val Thr Asp Ala Thr
    370                 375                 380

Glu Thr Thr Ile Thr Ile Ser Trp Arg Thr Lys Thr Glu Thr Ile Thr
385                 390                 395                 400

Gly Phe Gln Val Asp Ala Val Pro Ala Asn Gly Gln Thr Pro Ile Gln
                405                 410                 415

Arg Thr Ile Lys Pro Asp Val Arg Ser Tyr Thr Ile Thr Gly Leu Gln
            420                 425                 430

Pro Gly Thr Asp Tyr Lys Ile Tyr Leu Tyr Thr Leu Asn Asp Asn Ala
        435                 440                 445

Arg Ser Ser Pro Val Val Ile Asp Ala Ser Thr Ala Ile Asp Ala Pro
    450                 455                 460

Ser Asn Leu Arg Phe Leu Ala Thr Thr Pro Asn Ser Leu Leu Val Ser
465                 470                 475                 480

Trp Gln Pro Pro Arg Ala Arg Ile Thr Gly Tyr Ile Ile Lys Tyr Glu
                485                 490                 495

Lys Pro Gly Ser Pro Pro Arg Glu Val Val Pro Arg Pro Arg Pro Gly
            500                 505                 510

Val Thr Glu Ala Thr Ile Thr Gly Leu Glu Pro Gly Thr Glu Tyr Thr
        515                 520                 525

Ile Tyr Val Ile Ala Leu Lys Asn Asn Gln Lys Ser Glu Pro Leu Ile
    530                 535                 540

Gly Arg Lys Lys Thr
545

<210> SEQ ID NO 18
<211> LENGTH: 574
<212> TYPE: PRT
<213> ORGANISM: Artificial Sequence
<220> FEATURE:
<223> OTHER INFORMATION: Fibronectin fragment named CH-296 (RetroNectin)

<400> SEQUENCE: 18

Pro Thr Asp Leu Arg Phe Thr Asn Ile Gly Pro Asp Thr Met Arg Val
1               5                   10                  15

```
Thr Trp Ala Pro Pro Ser Ile Asp Leu Thr Asn Phe Leu Val Arg
             20                  25                  30

Tyr Ser Pro Val Lys Asn Glu Glu Asp Val Ala Glu Leu Ser Ile Ser
         35                  40                  45

Pro Ser Asp Asn Ala Val Val Leu Thr Asn Leu Leu Pro Gly Thr Glu
     50                  55                  60

Tyr Val Val Ser Val Ser Ser Val Tyr Glu Gln His Glu Ser Thr Pro
 65                  70                  75                  80

Leu Arg Gly Arg Gln Lys Thr Gly Leu Asp Ser Pro Thr Gly Ile Asp
                 85                  90                  95

Phe Ser Asp Ile Thr Ala Asn Ser Phe Thr Val His Trp Ile Ala Pro
             100                 105                 110

Arg Ala Thr Ile Thr Gly Tyr Arg Ile Arg His His Pro Glu His Phe
         115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Ala Ile Pro Ala Pro Thr Asp Leu Lys Phe
        275                 280                 285

Thr Gln Val Thr Pro Thr Ser Leu Ser Ala Gln Trp Thr Pro Pro Asn
    290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
                325                 330                 335

Val Ser Gly Leu Met Val Ala Thr Lys Tyr Glu Val Ser Val Tyr Ala
            340                 345                 350

Leu Lys Asp Thr Leu Thr Ser Arg Pro Ala Gln Gly Val Val Thr Thr
        355                 360                 365

Leu Glu Asn Val Ser Pro Pro Arg Arg Ala Arg Val Thr Asp Ala Thr
    370                 375                 380

Glu Thr Thr Ile Thr Ile Ser Trp Arg Thr Lys Thr Glu Thr Ile Thr
385                 390                 395                 400

Gly Phe Gln Val Asp Ala Val Pro Ala Asn Gly Gln Thr Pro Ile Gln
                405                 410                 415

Arg Thr Ile Lys Pro Asp Val Arg Ser Tyr Thr Ile Thr Gly Leu Gln
            420                 425                 430
```

```
Pro Gly Thr Asp Tyr Lys Ile Tyr Leu Tyr Thr Leu Asn Asp Asn Ala
            435                 440                 445

Arg Ser Ser Pro Val Val Ile Asp Ala Ser Thr Ala Ile Asp Ala Pro
    450                 455                 460

Ser Asn Leu Arg Phe Leu Ala Thr Thr Pro Asn Ser Leu Leu Val Ser
465                 470                 475                 480

Trp Gln Pro Pro Arg Ala Arg Ile Thr Gly Tyr Ile Ile Lys Tyr Glu
                485                 490                 495

Lys Pro Gly Ser Pro Arg Glu Val Val Pro Arg Pro Arg Pro Gly
                500                 505                 510                 Gly

Val Thr Glu Ala Thr Ile Thr Gly Leu Glu Pro Gly Thr Glu Tyr Thr
            515                 520                 525

Ile Tyr Val Ile Ala Leu Lys Asn Asn Gln Lys Ser Glu Pro Leu Ile
            530                 535                 540

Gly Arg Lys Lys Thr Asp Glu Leu Pro Gln Leu Val Thr Leu Pro His
545                 550                 555                 560

Pro Asn Leu His Gly Pro Glu Ile Leu Asp Val Pro Ser Thr
                565                 570
```

<210> SEQ ID NO 19
<211> LENGTH: 881
<212> TYPE: PRT
<213> ORGANISM: Artificial Sequence
<220> FEATURE:
<223> OTHER INFORMATION: Fibronectin fragment named FCH-296

<400> SEQUENCE: 19

```
Met Ser Gly Pro Val Glu Val Phe Ile Thr Glu Thr Pro Ser Gln Pro
1               5                   10                  15

Asn Ser His Pro Ile Gln Trp Asn Ala Pro Gln Pro Ser His Ile Ser
                20                  25                  30

Lys Tyr Ile Leu Arg Trp Arg Pro Lys Asn Ser Val Gly Arg Trp Lys
            35                  40                  45

Glu Ala Thr Ile Pro Gly His Leu Asn Ser Tyr Thr Ile Lys Gly Leu
    50                  55                  60

Lys Pro Gly Val Val Tyr Glu Gly Gln Leu Ile Ser Ile Gln Gln Tyr
65                  70                  75                  80

Gly His Gln Glu Val Thr Arg Phe Asp Phe Thr Thr Thr Ser Thr Ser
                85                  90                  95

Thr Pro Val Thr Ser Asn Thr Val Thr Gly Glu Thr Thr Pro Phe Ser
            100                 105                 110

Pro Leu Val Ala Thr Ser Glu Ser Val Thr Glu Ile Thr Ala Ser Ser
        115                 120                 125

Phe Val Val Ser Trp Val Ser Ala Ser Asp Thr Val Ser Gly Phe Arg
    130                 135                 140

Val Glu Tyr Glu Leu Ser Glu Glu Gly Asp Glu Pro Gln Tyr Leu Asp
145                 150                 155                 160

Leu Pro Ser Thr Ala Thr Ser Val Asn Ile Pro Asp Leu Leu Pro Gly
                165                 170                 175

Arg Lys Tyr Ile Val Asn Val Tyr Gln Ile Ser Glu Asp Gly Glu Gln
            180                 185                 190

Ser Leu Ile Leu Ser Thr Ser Gln Thr Thr Ala Pro Asp Ala Pro Pro
        195                 200                 205

Asp Pro Thr Val Asp Gln Val Asp Asp Thr Ser Ile Val Val Arg Trp
    210                 215                 220
```

```
Ser Arg Pro Gln Ala Pro Ile Thr Gly Tyr Arg Ile Val Tyr Ser Pro
225                 230                 235                 240

Ser Val Glu Gly Ser Ser Thr Glu Leu Asn Leu Pro Glu Thr Ala Asn
            245                 250                 255

Ser Val Thr Leu Ser Asp Leu Gln Pro Gly Val Gln Tyr Asn Ile Thr
        260                 265                 270

Ile Tyr Ala Val Glu Glu Asn Gln Glu Ser Thr Pro Val Val Ile Gln
    275                 280                 285

Gln Glu Thr Thr Gly Thr Pro Arg Ser Asp Gly Ser Ser Gly Ser Ser
290                 295                 300

Gly Ser Ser Pro Thr Asp Leu Arg Phe Thr Asn Ile Gly Pro Asp Thr
305                 310                 315                 320

Met Arg Val Thr Trp Ala Pro Pro Ser Ile Asp Leu Thr Asn Phe
                325                 330                 335

Leu Val Arg Tyr Ser Pro Val Lys Asn Glu Glu Asp Val Ala Glu Leu
            340                 345                 350

Ser Ile Ser Pro Ser Asp Asn Ala Val Val Leu Thr Asn Leu Leu Pro
        355                 360                 365

Gly Thr Glu Tyr Val Val Ser Val Ser Ser Val Tyr Glu Gln His Glu
370                 375                 380

Ser Thr Pro Leu Arg Gly Arg Gln Lys Thr Gly Leu Asp Ser Pro Thr
385                 390                 395                 400

Gly Ile Asp Phe Ser Asp Ile Thr Ala Asn Ser Phe Thr Val His Trp
                405                 410                 415

Ile Ala Pro Arg Ala Thr Ile Thr Gly Tyr Arg Ile Arg His His Pro
            420                 425                 430

Glu His Phe Ser Gly Arg Pro Arg Glu Asp Arg Val Pro His Ser Arg
        435                 440                 445

Asn Ser Ile Thr Leu Thr Asn Leu Thr Pro Gly Thr Glu Tyr Val Val
450                 455                 460

Ser Ile Val Ala Leu Asn Gly Arg Glu Glu Ser Pro Leu Leu Ile Gly
465                 470                 475                 480

Gln Gln Ser Thr Val Ser Asp Val Pro Arg Asp Leu Glu Val Val Ala
                485                 490                 495

Ala Thr Pro Thr Ser Leu Leu Ile Ser Trp Asp Ala Pro Ala Val Thr
            500                 505                 510

Val Arg Tyr Tyr Arg Ile Thr Tyr Gly Glu Thr Gly Gly Asn Ser Pro
        515                 520                 525

Val Gln Glu Phe Thr Val Pro Gly Ser Lys Ser Thr Ala Thr Ile Ser
530                 535                 540

Gly Leu Lys Pro Gly Val Asp Tyr Thr Ile Thr Val Tyr Ala Val Thr
545                 550                 555                 560

Gly Arg Gly Asp Ser Pro Ala Ser Ser Lys Pro Ile Ser Ile Asn Tyr
                565                 570                 575

Arg Thr Glu Ile Asp Lys Pro Ser Met Ala Ile Pro Ala Pro Thr Asp
            580                 585                 590

Leu Lys Phe Thr Gln Val Thr Pro Thr Ser Leu Ser Ala Gln Trp Thr
        595                 600                 605

Pro Pro Asn Val Gln Leu Thr Gly Tyr Arg Val Arg Val Thr Pro Lys
610                 615                 620

Glu Lys Thr Gly Pro Met Lys Glu Ile Asn Leu Ala Pro Asp Ser Ser
625                 630                 635                 640

Ser Val Val Val Ser Gly Leu Met Val Ala Thr Lys Tyr Glu Val Ser
```

-continued

```
                645                 650                 655
Val Tyr Ala Leu Lys Asp Thr Leu Thr Ser Arg Pro Ala Gln Gly Val
            660                 665                 670

Val Thr Thr Leu Glu Asn Val Ser Pro Arg Arg Ala Arg Val Thr
        675                 680                 685

Asp Ala Thr Glu Thr Thr Ile Thr Ile Ser Trp Arg Thr Lys Thr Glu
    690                 695                 700

Thr Ile Thr Gly Phe Gln Val Asp Ala Val Pro Ala Asn Gly Gln Thr
705                 710                 715                 720

Pro Ile Gln Arg Thr Ile Lys Pro Asp Val Arg Ser Tyr Thr Ile Thr
                725                 730                 735

Gly Leu Gln Pro Gly Thr Asp Tyr Lys Ile Tyr Leu Tyr Thr Leu Asn
            740                 745                 750

Asp Asn Ala Arg Ser Ser Pro Val Val Ile Asp Ala Ser Thr Ala Ile
        755                 760                 765

Asp Ala Pro Ser Asn Leu Arg Phe Leu Ala Thr Thr Pro Asn Ser Leu
    770                 775                 780

Leu Val Ser Trp Gln Pro Pro Arg Ala Arg Ile Thr Gly Tyr Ile Ile
785                 790                 795                 800

Lys Tyr Glu Lys Pro Gly Ser Pro Arg Glu Val Val Pro Arg Pro
                805                 810                 815

Arg Pro Gly Val Thr Glu Ala Thr Ile Thr Gly Leu Glu Pro Gly Thr
            820                 825                 830

Glu Tyr Thr Ile Tyr Val Ile Ala Leu Lys Asn Asn Gln Lys Ser Glu
        835                 840                 845

Pro Leu Ile Gly Arg Lys Lys Thr Asp Glu Leu Pro Gln Leu Val Thr
    850                 855                 860

Leu Pro His Pro Asn Leu His Gly Pro Glu Ile Leu Asp Val Pro Ser
865                 870                 875                 880

Thr
```

<210> SEQ ID NO 20
<211> LENGTH: 887
<212> TYPE: PRT
<213> ORGANISM: Artificial Sequence
<220> FEATURE:
<223> OTHER INFORMATION: His-tag FCH-296

<400> SEQUENCE: 20

```
Met His His His His His Ser Gly Pro Val Glu Val Phe Ile Thr
1               5                   10                  15

Glu Thr Pro Ser Gln Pro Asn Ser His Pro Ile Gln Trp Asn Ala Pro
            20                  25                  30

Gln Pro Ser His Ile Ser Lys Tyr Ile Leu Arg Trp Pro Lys Asn
        35                  40                  45

Ser Val Gly Arg Trp Lys Glu Ala Thr Ile Pro Gly His Leu Asn Ser
    50                  55                  60

Tyr Thr Ile Lys Gly Leu Lys Pro Gly Val Val Tyr Glu Gly Gln Leu
65                  70                  75                  80

Ile Ser Ile Gln Gln Tyr Gly His Gln Glu Val Thr Arg Phe Asp Phe
                85                  90                  95

Thr Thr Thr Ser Thr Ser Thr Pro Val Thr Ser Asn Thr Val Thr Gly
            100                 105                 110

Glu Thr Thr Pro Phe Ser Pro Leu Val Ala Thr Ser Glu Ser Val Thr
        115                 120                 125
```

```
Glu Ile Thr Ala Ser Ser Phe Val Ser Trp Val Ser Ala Ser Asp
        130                 135                 140

Thr Val Ser Gly Phe Arg Val Glu Tyr Glu Leu Ser Glu Glu Gly Asp
145                 150                 155                 160

Glu Pro Gln Tyr Leu Asp Leu Pro Ser Thr Ala Thr Ser Val Asn Ile
                165                 170                 175

Pro Asp Leu Leu Pro Gly Arg Lys Tyr Ile Val Asn Val Tyr Gln Ile
                180                 185                 190

Ser Glu Asp Gly Glu Gln Ser Leu Ile Leu Ser Thr Ser Gln Thr Thr
            195                 200                 205

Ala Pro Asp Ala Pro Pro Asp Pro Thr Val Asp Gln Val Asp Asp Thr
210                 215                 220

Ser Ile Val Val Arg Trp Ser Arg Pro Gln Ala Pro Ile Thr Gly Tyr
225                 230                 235                 240

Arg Ile Val Tyr Ser Pro Ser Val Glu Gly Ser Ser Thr Glu Leu Asn
                245                 250                 255

Leu Pro Glu Thr Ala Asn Ser Val Thr Leu Ser Asp Leu Gln Pro Gly
            260                 265                 270

Val Gln Tyr Asn Ile Thr Ile Tyr Ala Val Glu Glu Asn Gln Glu Ser
    275                 280                 285

Thr Pro Val Val Ile Gln Gln Glu Thr Thr Gly Thr Pro Arg Ser Asp
290                 295                 300

Gly Ser Ser Gly Ser Ser Gly Ser Ser Pro Thr Asp Leu Arg Phe Thr
305                 310                 315                 320

Asn Ile Gly Pro Asp Thr Met Arg Val Thr Trp Ala Pro Pro Pro Ser
                325                 330                 335

Ile Asp Leu Thr Asn Phe Leu Val Arg Tyr Ser Pro Val Lys Asn Glu
            340                 345                 350

Glu Asp Val Ala Glu Leu Ser Ile Ser Pro Ser Asp Asn Ala Val Val
        355                 360                 365

Leu Thr Asn Leu Leu Pro Gly Thr Glu Tyr Val Val Ser Val Ser Ser
370                 375                 380

Val Tyr Glu Gln His Glu Ser Thr Pro Leu Arg Gly Arg Gln Lys Thr
385                 390                 395                 400

Gly Leu Asp Ser Pro Thr Gly Ile Asp Phe Ser Asp Ile Thr Ala Asn
                405                 410                 415

Ser Phe Thr Val His Trp Ile Ala Pro Arg Ala Thr Ile Thr Gly Tyr
            420                 425                 430

Arg Ile Arg His His Pro Glu His Phe Ser Gly Arg Pro Arg Glu Asp
        435                 440                 445

Arg Val Pro His Ser Arg Asn Ser Ile Thr Leu Thr Asn Leu Thr Pro
450                 455                 460

Gly Thr Glu Tyr Val Val Ser Ile Val Ala Leu Asn Gly Arg Glu Glu
465                 470                 475                 480

Ser Pro Leu Leu Ile Gly Gln Gln Ser Thr Val Ser Asp Val Pro Arg
                485                 490                 495

Asp Leu Glu Val Val Ala Ala Thr Pro Thr Ser Leu Leu Ile Ser Trp
            500                 505                 510

Asp Ala Pro Ala Val Thr Val Arg Tyr Tyr Arg Ile Thr Tyr Gly Glu
        515                 520                 525

Thr Gly Gly Asn Ser Pro Val Gln Glu Phe Thr Val Pro Gly Ser Lys
530                 535                 540
```

```
Ser Thr Ala Thr Ile Ser Gly Leu Lys Pro Gly Val Asp Tyr Thr Ile
545                 550                 555                 560

Thr Val Tyr Ala Val Thr Gly Arg Gly Asp Ser Pro Ala Ser Ser Lys
                565                 570                 575

Pro Ile Ser Ile Asn Tyr Arg Thr Glu Ile Asp Lys Pro Ser Met Ala
            580                 585                 590

Ile Pro Ala Pro Thr Asp Leu Lys Phe Thr Gln Val Thr Pro Thr Ser
        595                 600                 605

Leu Ser Ala Gln Trp Thr Pro Pro Asn Val Gln Leu Thr Gly Tyr Arg
    610                 615                 620

Val Arg Val Thr Pro Lys Glu Lys Thr Gly Pro Met Lys Glu Ile Asn
625                 630                 635                 640

Leu Ala Pro Asp Ser Ser Val Val Val Ser Gly Leu Met Val Ala
                645                 650                 655

Thr Lys Tyr Glu Val Ser Val Tyr Ala Leu Lys Asp Thr Leu Thr Ser
                660                 665                 670

Arg Pro Ala Gln Gly Val Val Thr Thr Leu Glu Asn Val Ser Pro Pro
                675                 680                 685

Arg Arg Ala Arg Val Thr Asp Ala Thr Glu Thr Thr Ile Thr Ile Ser
690                 695                 700

Trp Arg Thr Lys Thr Glu Thr Ile Thr Gly Phe Gln Val Asp Ala Val
705                 710                 715                 720

Pro Ala Asn Gly Gln Thr Pro Ile Gln Arg Thr Ile Lys Pro Asp Val
                725                 730                 735

Arg Ser Tyr Thr Ile Thr Gly Leu Gln Pro Gly Thr Asp Tyr Lys Ile
                740                 745                 750

Tyr Leu Tyr Thr Leu Asn Asp Asn Ala Arg Ser Ser Pro Val Val Ile
            755                 760                 765

Asp Ala Ser Thr Ala Ile Asp Ala Pro Ser Asn Leu Arg Phe Leu Ala
        770                 775                 780

Thr Thr Pro Asn Ser Leu Leu Val Ser Trp Gln Pro Pro Arg Ala Arg
785                 790                 795                 800

Ile Thr Gly Tyr Ile Ile Lys Tyr Glu Lys Pro Gly Ser Pro Pro Arg
                805                 810                 815

Glu Val Val Pro Arg Pro Arg Pro Gly Val Thr Glu Ala Thr Ile Thr
                820                 825                 830

Gly Leu Glu Pro Gly Thr Glu Tyr Thr Ile Tyr Val Ile Ala Leu Lys
                835                 840                 845

Asn Asn Gln Lys Ser Glu Pro Leu Ile Gly Arg Lys Lys Thr Asp Glu
                850                 855                 860

Leu Pro Gln Leu Val Thr Leu Pro His Pro Asn Leu His Gly Pro Glu
865                 870                 875                 880

Ile Leu Asp Val Pro Ser Thr
                885
```

<210> SEQ ID NO 21
<211> LENGTH: 83
<212> TYPE: PRT
<213> ORGANISM: Artificial Sequence
<220> FEATURE:
<223> OTHER INFORMATION: N-terminal 9a.a. deletion of III-1

<400> SEQUENCE: 21

```
Glu Thr Pro Ser Gln Pro Asn Ser His Pro Ile Gln Trp Asn Ala Pro
1               5                   10                  15
```

```
Gln Pro Ser His Ile Ser Lys Tyr Ile Leu Arg Trp Arg Pro Lys Asn
             20                  25                  30

Ser Val Gly Arg Trp Lys Glu Ala Thr Ile Pro Gly His Leu Asn Ser
         35                  40                  45

Tyr Thr Ile Lys Gly Leu Lys Pro Gly Val Val Tyr Glu Gly Gln Leu
     50                  55                  60

Ile Ser Ile Gln Gln Tyr Gly His Gln Glu Val Thr Arg Phe Asp Phe
65                  70                  75                  80

Thr Thr Thr

<210> SEQ ID NO 22
<211> LENGTH: 86
<212> TYPE: PRT
<213> ORGANISM: Artificial Sequence
<220> FEATURE:
<223> OTHER INFORMATION: N-terminal 6a.a. deletion of III-1

<400> SEQUENCE: 22

Phe Ile Thr Glu Thr Pro Ser Gln Pro Asn Ser His Pro Ile Gln Trp
1               5                  10                  15

Asn Ala Pro Gln Pro Ser His Ile Ser Lys Tyr Ile Leu Arg Trp Arg
             20                  25                  30

Pro Lys Asn Ser Val Gly Arg Trp Lys Glu Ala Thr Ile Pro Gly His
         35                  40                  45

Leu Asn Ser Tyr Thr Ile Lys Gly Leu Lys Pro Gly Val Val Tyr Glu
     50                  55                  60

Gly Gln Leu Ile Ser Ile Gln Gln Tyr Gly His Gln Glu Val Thr Arg
65                  70                  75                  80

Phe Asp Phe Thr Thr Thr
             85

<210> SEQ ID NO 23
<211> LENGTH: 87
<212> TYPE: PRT
<213> ORGANISM: Artificial Sequence
<220> FEATURE:
<223> OTHER INFORMATION: N-terminal 5a.a. deletion of III-1

<400> SEQUENCE: 23

Val Phe Ile Thr Glu Thr Pro Ser Gln Pro Asn Ser His Pro Ile Gln
1               5                  10                  15

Trp Asn Ala Pro Gln Pro Ser His Ile Ser Lys Tyr Ile Leu Arg Trp
             20                  25                  30

Arg Pro Lys Asn Ser Val Gly Arg Trp Lys Glu Ala Thr Ile Pro Gly
         35                  40                  45

His Leu Asn Ser Tyr Thr Ile Lys Gly Leu Lys Pro Gly Val Val Tyr
     50                  55                  60

Glu Gly Gln Leu Ile Ser Ile Gln Gln Tyr Gly His Gln Glu Val Thr
65                  70                  75                  80

Arg Phe Asp Phe Thr Thr Thr
             85

<210> SEQ ID NO 24
<211> LENGTH: 89
<212> TYPE: PRT
<213> ORGANISM: Artificial Sequence
<220> FEATURE:
<223> OTHER INFORMATION: N-terminal 3a.a. deletion of III-1

<400> SEQUENCE: 24
```

```
Val Glu Val Phe Ile Thr Glu Thr Pro Ser Gln Pro Asn Ser His Pro
1               5                   10                  15

Ile Gln Trp Asn Ala Pro Gln Pro Ser His Ile Ser Lys Tyr Ile Leu
            20                  25                  30

Arg Trp Arg Pro Lys Asn Ser Val Gly Arg Trp Lys Glu Ala Thr Ile
        35                  40                  45

Pro Gly His Leu Asn Ser Tyr Thr Ile Lys Gly Leu Lys Pro Gly Val
    50                  55                  60

Val Tyr Glu Gly Gln Leu Ile Ser Ile Gln Gln Tyr Gly His Gln Glu
65              70                  75                  80

Val Thr Arg Phe Asp Phe Thr Thr Thr
                85
```

<210> SEQ ID NO 25
<211> LENGTH: 872
<212> TYPE: PRT
<213> ORGANISM: Artificial Sequence
<220> FEATURE:
<223> OTHER INFORMATION: N-terminal 9a.a. deletion of FCH-296

<400> SEQUENCE: 25

```
Met Glu Thr Pro Ser Gln Pro Asn Ser His Pro Ile Gln Trp Asn Ala
1               5                   10                  15

Pro Gln Pro Ser His Ile Ser Lys Tyr Ile Leu Arg Trp Arg Pro Lys
            20                  25                  30

Asn Ser Val Gly Arg Trp Lys Glu Ala Thr Ile Pro Gly His Leu Asn
        35                  40                  45

Ser Tyr Thr Ile Lys Gly Leu Lys Pro Gly Val Val Tyr Glu Gly Gln
    50                  55                  60

Leu Ile Ser Ile Gln Gln Tyr Gly His Gln Glu Val Thr Arg Phe Asp
65              70                  75                  80

Phe Thr Thr Thr Ser Thr Ser Thr Pro Val Thr Ser Asn Thr Val Thr
                85                  90                  95

Gly Glu Thr Thr Pro Phe Ser Pro Leu Val Ala Thr Ser Glu Ser Val
                100                 105                 110

Thr Glu Ile Thr Ala Ser Ser Phe Val Val Ser Trp Val Ser Ala Ser
            115                 120                 125

Asp Thr Val Ser Gly Phe Arg Val Glu Tyr Glu Leu Ser Glu Glu Gly
        130                 135                 140

Asp Glu Pro Gln Tyr Leu Asp Leu Pro Ser Thr Ala Thr Ser Val Asn
145                 150                 155                 160

Ile Pro Asp Leu Leu Pro Gly Arg Lys Tyr Ile Val Asn Val Tyr Gln
                165                 170                 175

Ile Ser Glu Asp Gly Glu Gln Ser Leu Ile Leu Ser Thr Ser Gln Thr
            180                 185                 190

Thr Ala Pro Asp Ala Pro Pro Asp Pro Thr Val Asp Gln Val Asp Asp
        195                 200                 205

Thr Ser Ile Val Val Arg Trp Ser Arg Pro Gln Ala Pro Ile Thr Gly
    210                 215                 220

Tyr Arg Ile Val Tyr Ser Pro Ser Val Glu Gly Ser Ser Thr Glu Leu
225                 230                 235                 240

Asn Leu Pro Glu Thr Ala Asn Ser Val Thr Leu Ser Asp Leu Gln Pro
                245                 250                 255

Gly Val Gln Tyr Asn Ile Thr Ile Tyr Ala Val Glu Glu Asn Gln Glu
            260                 265                 270
```

```
Ser Thr Pro Val Val Ile Gln Gln Glu Thr Thr Gly Thr Pro Arg Ser
        275                 280                 285

Asp Gly Ser Ser Gly Ser Ser Gly Ser Ser Pro Thr Asp Leu Arg Phe
        290                 295                 300

Thr Asn Ile Gly Pro Asp Thr Met Arg Val Thr Trp Ala Pro Pro Pro
305                 310                 315                 320

Ser Ile Asp Leu Thr Asn Phe Leu Val Arg Tyr Ser Pro Val Lys Asn
                325                 330                 335

Glu Glu Asp Val Ala Glu Leu Ser Ile Ser Pro Ser Asp Asn Ala Val
                340                 345                 350

Val Leu Thr Asn Leu Leu Pro Gly Thr Glu Tyr Val Val Ser Val Ser
                355                 360                 365

Ser Val Tyr Glu Gln His Glu Ser Thr Pro Leu Arg Gly Arg Gln Lys
        370                 375                 380

Thr Gly Leu Asp Ser Pro Thr Gly Ile Asp Phe Ser Asp Ile Thr Ala
385                 390                 395                 400

Asn Ser Phe Thr Val His Trp Ile Ala Pro Arg Ala Thr Ile Thr Gly
                405                 410                 415

Tyr Arg Ile Arg His His Pro Glu His Phe Ser Gly Arg Pro Arg Glu
        420                 425                 430

Asp Arg Val Pro His Ser Arg Asn Ser Ile Thr Leu Thr Asn Leu Thr
                435                 440                 445

Pro Gly Thr Glu Tyr Val Val Ser Ile Val Ala Leu Asn Gly Arg Glu
        450                 455                 460

Glu Ser Pro Leu Leu Ile Gly Gln Gln Ser Thr Val Ser Asp Val Pro
465                 470                 475                 480

Arg Asp Leu Glu Val Val Ala Ala Thr Pro Thr Ser Leu Leu Ile Ser
                485                 490                 495

Trp Asp Ala Pro Ala Val Thr Val Arg Tyr Tyr Arg Ile Thr Tyr Gly
                500                 505                 510

Glu Thr Gly Gly Asn Ser Pro Val Gln Glu Phe Thr Val Pro Gly Ser
        515                 520                 525

Lys Ser Thr Ala Thr Ile Ser Gly Leu Lys Pro Gly Val Asp Tyr Thr
        530                 535                 540

Ile Thr Val Tyr Ala Val Thr Gly Arg Gly Asp Ser Pro Ala Ser Ser
545                 550                 555                 560

Lys Pro Ile Ser Ile Asn Tyr Arg Thr Glu Ile Asp Lys Pro Ser Met
                565                 570                 575

Ala Ile Pro Ala Pro Thr Asp Leu Lys Phe Thr Gln Val Thr Pro Thr
                580                 585                 590

Ser Leu Ser Ala Gln Trp Thr Pro Pro Asn Val Gln Leu Thr Gly Tyr
        595                 600                 605

Arg Val Arg Val Thr Pro Lys Glu Lys Thr Gly Pro Met Lys Glu Ile
        610                 615                 620

Asn Leu Ala Pro Asp Ser Ser Val Val Ser Gly Leu Met Val
625                 630                 635                 640

Ala Thr Lys Tyr Glu Val Ser Val Tyr Ala Leu Lys Asp Thr Leu Thr
                645                 650                 655

Ser Arg Pro Ala Gln Gly Val Val Thr Thr Leu Glu Asn Val Ser Pro
                660                 665                 670

Pro Arg Arg Ala Arg Val Thr Asp Ala Thr Glu Thr Thr Ile Thr Ile
                675                 680                 685
```

```
Ser Trp Arg Thr Lys Thr Glu Thr Ile Thr Gly Phe Gln Val Asp Ala
690                 695                 700

Val Pro Ala Asn Gly Gln Thr Pro Ile Gln Arg Thr Ile Lys Pro Asp
705                 710                 715                 720

Val Arg Ser Tyr Thr Ile Thr Gly Leu Gln Pro Gly Thr Asp Tyr Lys
            725                 730                 735

Ile Tyr Leu Tyr Thr Leu Asn Asp Asn Ala Arg Ser Ser Pro Val Val
                740                 745                 750

Ile Asp Ala Ser Thr Ala Ile Asp Ala Pro Ser Asn Leu Arg Phe Leu
            755                 760                 765

Ala Thr Thr Pro Asn Ser Leu Leu Val Ser Trp Gln Pro Pro Arg Ala
770                 775                 780

Arg Ile Thr Gly Tyr Ile Ile Lys Tyr Glu Lys Pro Gly Ser Pro Pro
785                 790                 795                 800

Arg Glu Val Val Pro Arg Pro Arg Pro Gly Val Thr Glu Ala Thr Ile
                805                 810                 815

Thr Gly Leu Glu Pro Gly Thr Glu Tyr Thr Ile Tyr Val Ile Ala Leu
            820                 825                 830

Lys Asn Asn Gln Lys Ser Glu Pro Leu Ile Gly Arg Lys Lys Thr Asp
                835                 840                 845

Glu Leu Pro Gln Leu Val Thr Leu Pro His Pro Asn Leu His Gly Pro
850                 855                 860

Glu Ile Leu Asp Val Pro Ser Thr
865                 870

<210> SEQ ID NO 26
<211> LENGTH: 875
<212> TYPE: PRT
<213> ORGANISM: Artificial Sequence
<220> FEATURE:
<223> OTHER INFORMATION: N-terminal 6a.a. deletion of FCH-296

<400> SEQUENCE: 26

Met Phe Ile Thr Glu Thr Pro Ser Gln Pro Asn Ser His Pro Ile Gln
1               5                   10                  15

Trp Asn Ala Pro Gln Pro Ser His Ile Ser Lys Tyr Ile Leu Arg Trp
            20                  25                  30

Arg Pro Lys Asn Ser Val Gly Arg Trp Lys Glu Ala Thr Ile Pro Gly
        35                  40                  45

His Leu Asn Ser Tyr Thr Ile Lys Gly Leu Lys Pro Gly Val Val Tyr
    50                  55                  60

Glu Gly Gln Leu Ile Ser Ile Gln Gln Tyr Gly His Gln Glu Val Thr
65                  70                  75                  80

Arg Phe Asp Phe Thr Thr Thr Ser Thr Ser Thr Pro Val Thr Ser Asn
                85                  90                  95

Thr Val Thr Gly Glu Thr Thr Pro Phe Ser Pro Leu Val Ala Thr Ser
            100                 105                 110

Glu Ser Val Thr Glu Ile Thr Ala Ser Ser Phe Val Val Ser Trp Val
        115                 120                 125

Ser Ala Ser Asp Thr Val Ser Gly Phe Arg Val Glu Tyr Glu Leu Ser
    130                 135                 140

Glu Glu Gly Asp Glu Pro Gln Tyr Leu Asp Leu Pro Ser Thr Ala Thr
145                 150                 155                 160

Ser Val Asn Ile Pro Asp Leu Leu Pro Gly Arg Lys Tyr Ile Val Asn
                165                 170                 175
```

```
Val Tyr Gln Ile Ser Glu Asp Gly Glu Gln Ser Leu Ile Leu Ser Thr
                180                 185                 190

Ser Gln Thr Thr Ala Pro Asp Ala Pro Pro Asp Pro Thr Val Asp Gln
            195                 200                 205

Val Asp Asp Thr Ser Ile Val Val Arg Trp Ser Arg Pro Gln Ala Pro
    210                 215                 220

Ile Thr Gly Tyr Arg Ile Val Tyr Ser Pro Ser Val Glu Gly Ser Ser
225                 230                 235                 240

Thr Glu Leu Asn Leu Pro Glu Thr Ala Asn Ser Val Thr Leu Ser Asp
                245                 250                 255

Leu Gln Pro Gly Val Gln Tyr Asn Ile Thr Ile Tyr Ala Val Glu Glu
            260                 265                 270

Asn Gln Glu Ser Thr Pro Val Val Ile Gln Gln Glu Thr Thr Gly Thr
    275                 280                 285

Pro Arg Ser Asp Gly Ser Ser Gly Ser Ser Gly Ser Ser Pro Thr Asp
290                 295                 300

Leu Arg Phe Thr Asn Ile Gly Pro Asp Thr Met Arg Val Thr Trp Ala
305                 310                 315                 320

Pro Pro Pro Ser Ile Asp Leu Thr Asn Phe Leu Val Arg Tyr Ser Pro
                325                 330                 335

Val Lys Asn Glu Glu Asp Val Ala Glu Leu Ser Ile Ser Pro Ser Asp
            340                 345                 350

Asn Ala Val Val Leu Thr Asn Leu Leu Pro Gly Thr Glu Tyr Val Val
    355                 360                 365

Ser Val Ser Ser Val Tyr Glu Gln His Glu Ser Thr Pro Leu Arg Gly
370                 375                 380

Arg Gln Lys Thr Gly Leu Asp Ser Pro Thr Gly Ile Asp Phe Ser Asp
385                 390                 395                 400

Ile Thr Ala Asn Ser Phe Thr Val His Trp Ile Ala Pro Arg Ala Thr
                405                 410                 415

Ile Thr Gly Tyr Arg Ile Arg His His Pro Glu His Phe Ser Gly Arg
            420                 425                 430

Pro Arg Glu Asp Arg Val Pro His Ser Arg Asn Ser Ile Thr Leu Thr
    435                 440                 445

Asn Leu Thr Pro Gly Thr Glu Tyr Val Val Ser Ile Val Ala Leu Asn
450                 455                 460

Gly Arg Glu Glu Ser Pro Leu Leu Ile Gly Gln Gln Ser Thr Val Ser
465                 470                 475                 480

Asp Val Pro Arg Asp Leu Glu Val Val Ala Ala Thr Pro Thr Ser Leu
                485                 490                 495

Leu Ile Ser Trp Asp Ala Pro Ala Val Thr Val Arg Tyr Tyr Arg Ile
            500                 505                 510

Thr Tyr Gly Glu Thr Gly Gly Asn Ser Pro Val Gln Glu Phe Thr Val
    515                 520                 525

Pro Gly Ser Lys Ser Thr Ala Thr Ile Ser Gly Leu Lys Pro Gly Val
530                 535                 540

Asp Tyr Thr Ile Thr Val Tyr Ala Val Thr Gly Arg Gly Asp Ser Pro
545                 550                 555                 560

Ala Ser Ser Lys Pro Ile Ser Ile Asn Tyr Arg Thr Glu Ile Asp Lys
                565                 570                 575

Pro Ser Met Ala Ile Pro Ala Pro Thr Asp Leu Lys Phe Thr Gln Val
            580                 585                 590

Thr Pro Thr Ser Leu Ser Ala Gln Trp Thr Pro Pro Asn Val Gln Leu
```

```
                595                 600                 605
Thr Gly Tyr Arg Val Arg Val Thr Pro Lys Glu Lys Thr Gly Pro Met
610                 615                 620
Lys Glu Ile Asn Leu Ala Pro Asp Ser Ser Val Val Ser Gly
625                 630                 635                 640
Leu Met Val Ala Thr Lys Tyr Glu Val Ser Val Tyr Ala Leu Lys Asp
                645                 650                 655
Thr Leu Thr Ser Arg Pro Ala Gln Gly Val Val Thr Thr Leu Glu Asn
                660                 665                 670
Val Ser Pro Pro Arg Arg Ala Arg Val Thr Asp Ala Thr Glu Thr Thr
            675                 680                 685
Ile Thr Ile Ser Trp Arg Thr Lys Thr Glu Thr Ile Thr Gly Phe Gln
690                 695                 700
Val Asp Ala Val Pro Ala Asn Gly Gln Thr Pro Ile Gln Arg Thr Ile
705                 710                 715                 720
Lys Pro Asp Val Arg Ser Tyr Thr Ile Thr Gly Leu Gln Pro Gly Thr
                725                 730                 735
Asp Tyr Lys Ile Tyr Leu Tyr Thr Leu Asn Asp Asn Ala Arg Ser Ser
                740                 745                 750
Pro Val Val Ile Asp Ala Ser Thr Ala Ile Asp Ala Pro Ser Asn Leu
            755                 760                 765
Arg Phe Leu Ala Thr Thr Pro Asn Ser Leu Leu Val Ser Trp Gln Pro
770                 775                 780
Pro Arg Ala Arg Ile Thr Gly Tyr Ile Ile Lys Tyr Glu Lys Pro Gly
785                 790                 795                 800
Ser Pro Pro Arg Glu Val Val Pro Arg Pro Arg Pro Gly Val Thr Glu
                805                 810                 815
Ala Thr Ile Thr Gly Leu Glu Pro Gly Thr Glu Tyr Thr Ile Tyr Val
                820                 825                 830
Ile Ala Leu Lys Asn Asn Gln Lys Ser Glu Pro Leu Ile Gly Arg Lys
            835                 840                 845
Lys Thr Asp Glu Leu Pro Gln Leu Val Thr Leu Pro His Pro Asn Leu
            850                 855                 860
His Gly Pro Glu Ile Leu Asp Val Pro Ser Thr
865                 870                 875

<210> SEQ ID NO 27
<211> LENGTH: 876
<212> TYPE: PRT
<213> ORGANISM: Artificial Sequence
<220> FEATURE:
<223> OTHER INFORMATION: N-terminal 5a.a. deletion of FCH-296

<400> SEQUENCE: 27

Met Val Phe Ile Thr Glu Thr Pro Ser Gln Pro Asn Ser His Pro Ile
1               5                   10                  15

Gln Trp Asn Ala Pro Gln Pro Ser His Ile Ser Lys Tyr Ile Leu Arg
                20                  25                  30

Trp Arg Pro Lys Asn Ser Val Gly Arg Trp Lys Glu Ala Thr Ile Pro
            35                  40                  45

Gly His Leu Asn Ser Tyr Thr Ile Lys Gly Leu Lys Pro Gly Val Val
        50                  55                  60

Tyr Glu Gly Gln Leu Ile Ser Ile Gln Gln Tyr Gly His Gln Glu Val
65                  70                  75                  80

Thr Arg Phe Asp Phe Thr Thr Thr Ser Thr Ser Thr Pro Val Thr Ser
```

```
                     85                  90                  95
Asn Thr Val Thr Gly Glu Thr Thr Pro Phe Ser Pro Leu Val Ala Thr
                100                 105                 110

Ser Glu Ser Val Thr Glu Ile Thr Ala Ser Ser Phe Val Val Ser Trp
            115                 120                 125

Val Ser Ala Ser Asp Thr Val Ser Gly Phe Arg Val Glu Tyr Glu Leu
        130                 135                 140

Ser Glu Glu Gly Asp Glu Pro Gln Tyr Leu Asp Leu Pro Ser Thr Ala
145                 150                 155                 160

Thr Ser Val Asn Ile Pro Asp Leu Leu Pro Gly Arg Lys Tyr Ile Val
                165                 170                 175

Asn Val Tyr Gln Ile Ser Glu Asp Gly Glu Gln Ser Leu Ile Leu Ser
                180                 185                 190

Thr Ser Gln Thr Thr Ala Pro Asp Ala Pro Pro Asp Pro Thr Val Asp
            195                 200                 205

Gln Val Asp Asp Thr Ser Ile Val Val Arg Trp Ser Arg Pro Gln Ala
        210                 215                 220

Pro Ile Thr Gly Tyr Arg Ile Val Tyr Ser Pro Ser Val Glu Gly Ser
225                 230                 235                 240

Ser Thr Glu Leu Asn Leu Pro Glu Thr Ala Asn Ser Val Thr Leu Ser
                245                 250                 255

Asp Leu Gln Pro Gly Val Gln Tyr Asn Ile Thr Ile Tyr Ala Val Glu
            260                 265                 270

Glu Asn Gln Glu Ser Thr Pro Val Val Ile Gln Gln Glu Thr Thr Gly
        275                 280                 285

Thr Pro Arg Ser Asp Gly Ser Ser Gly Ser Ser Gly Ser Ser Pro Thr
290                 295                 300

Asp Leu Arg Phe Thr Asn Ile Gly Pro Asp Thr Met Arg Val Thr Trp
305                 310                 315                 320

Ala Pro Pro Pro Ser Ile Asp Leu Thr Asn Phe Leu Val Arg Tyr Ser
                325                 330                 335

Pro Val Lys Asn Glu Glu Asp Val Ala Glu Leu Ser Ile Ser Pro Ser
            340                 345                 350

Asp Asn Ala Val Val Leu Thr Asn Leu Leu Pro Gly Thr Glu Tyr Val
        355                 360                 365

Val Ser Val Ser Ser Val Tyr Glu Gln His Glu Ser Thr Pro Leu Arg
        370                 375                 380

Gly Arg Gln Lys Thr Gly Leu Asp Ser Pro Thr Gly Ile Asp Phe Ser
385                 390                 395                 400

Asp Ile Thr Ala Asn Ser Phe Thr Val His Trp Ile Ala Pro Arg Ala
                405                 410                 415

Thr Ile Thr Gly Tyr Arg Ile Arg His His Pro Glu His Phe Ser Gly
            420                 425                 430

Arg Pro Arg Glu Asp Arg Val Pro His Ser Arg Asn Ser Ile Thr Leu
        435                 440                 445

Thr Asn Leu Thr Pro Gly Thr Glu Tyr Val Val Ser Ile Val Ala Leu
    450                 455                 460

Asn Gly Arg Glu Glu Ser Pro Leu Leu Ile Gly Gln Gln Ser Thr Val
465                 470                 475                 480

Ser Asp Val Pro Arg Asp Leu Glu Val Val Ala Ala Thr Pro Thr Ser
                485                 490                 495

Leu Leu Ile Ser Trp Asp Ala Pro Ala Val Thr Val Arg Tyr Tyr Arg
            500                 505                 510
```

Ile Thr Tyr Gly Glu Thr Gly Asn Ser Pro Val Gln Glu Phe Thr
            515                 520                 525

Val Pro Gly Ser Lys Ser Thr Ala Thr Ile Ser Gly Leu Lys Pro Gly
530                 535                 540

Val Asp Tyr Thr Ile Thr Val Tyr Ala Val Thr Gly Arg Gly Asp Ser
545                 550                 555                 560

Pro Ala Ser Ser Lys Pro Ile Ser Ile Asn Tyr Arg Thr Glu Ile Asp
                565                 570                 575

Lys Pro Ser Met Ala Ile Pro Ala Pro Thr Asp Leu Lys Phe Thr Gln
            580                 585                 590

Val Thr Pro Thr Ser Leu Ser Ala Gln Trp Thr Pro Asn Val Gln
595                 600                 605

Leu Thr Gly Tyr Arg Val Arg Val Thr Pro Lys Glu Lys Thr Gly Pro
            610                 615                 620

Met Lys Glu Ile Asn Leu Ala Pro Asp Ser Ser Val Val Ser
625                 630                 635                 640

Gly Leu Met Val Ala Thr Lys Tyr Glu Val Ser Val Tyr Ala Leu Lys
                645                 650                 655

Asp Thr Leu Thr Ser Arg Pro Ala Gln Gly Val Val Thr Leu Glu
            660                 665                 670

Asn Val Ser Pro Pro Arg Arg Ala Arg Val Thr Asp Ala Thr Glu Thr
                675                 680                 685

Thr Ile Thr Ile Ser Trp Arg Thr Lys Thr Glu Thr Ile Thr Gly Phe
            690                 695                 700

Gln Val Asp Ala Val Pro Ala Asn Gly Gln Thr Pro Ile Gln Arg Thr
705                 710                 715                 720

Ile Lys Pro Asp Val Arg Ser Tyr Thr Ile Thr Gly Leu Gln Pro Gly
                725                 730                 735

Thr Asp Tyr Lys Ile Tyr Leu Tyr Thr Leu Asn Asp Asn Ala Arg Ser
            740                 745                 750

Ser Pro Val Val Ile Asp Ala Ser Thr Ala Ile Asp Ala Pro Ser Asn
                755                 760                 765

Leu Arg Phe Leu Ala Thr Thr Pro Asn Ser Leu Leu Val Ser Trp Gln
            770                 775                 780

Pro Pro Arg Ala Arg Ile Thr Gly Tyr Ile Ile Lys Tyr Glu Lys Pro
785                 790                 795                 800

Gly Ser Pro Pro Arg Glu Val Val Pro Arg Pro Arg Pro Gly Val Thr
                805                 810                 815

Glu Ala Thr Ile Thr Gly Leu Glu Pro Gly Thr Glu Tyr Thr Ile Tyr
            820                 825                 830

Val Ile Ala Leu Lys Asn Asn Gln Lys Ser Glu Pro Leu Ile Gly Arg
                835                 840                 845

Lys Lys Thr Asp Glu Leu Pro Gln Leu Val Thr Leu Pro His Pro Asn
850                 855                 860

Leu His Gly Pro Glu Ile Leu Asp Val Pro Ser Thr
865                 870                 875

<210> SEQ ID NO 28
<211> LENGTH: 878
<212> TYPE: PRT
<213> ORGANISM: Artificial Sequence
<220> FEATURE:
<223> OTHER INFORMATION: N-terminal 3a.a. deletion of FCH-296

<400> SEQUENCE: 28

```
Met Val Glu Val Phe Ile Thr Glu Thr Pro Ser Gln Pro Asn Ser His
1               5                   10                  15

Pro Ile Gln Trp Asn Ala Pro Gln Pro Ser His Ile Ser Lys Tyr Ile
            20                  25                  30

Leu Arg Trp Arg Pro Lys Asn Ser Val Gly Arg Trp Lys Glu Ala Thr
        35                  40                  45

Ile Pro Gly His Leu Asn Ser Tyr Thr Ile Lys Gly Leu Lys Pro Gly
50                  55                  60

Val Val Tyr Glu Gly Gln Leu Ile Ser Ile Gln Gln Tyr Gly His Gln
65                  70                  75                  80

Glu Val Thr Arg Phe Asp Phe Thr Thr Ser Thr Ser Thr Pro Val
                85                  90                  95

Thr Ser Asn Thr Val Thr Gly Glu Thr Thr Pro Phe Ser Pro Leu Val
            100                 105                 110

Ala Thr Ser Glu Ser Val Thr Glu Ile Thr Ala Ser Ser Phe Val Val
        115                 120                 125

Ser Trp Val Ser Ala Ser Asp Thr Val Ser Gly Phe Arg Val Glu Tyr
    130                 135                 140

Glu Leu Ser Glu Glu Gly Asp Glu Pro Gln Tyr Leu Asp Leu Pro Ser
145                 150                 155                 160

Thr Ala Thr Ser Val Asn Ile Pro Asp Leu Leu Pro Gly Arg Lys Tyr
                165                 170                 175

Ile Val Asn Val Tyr Gln Ile Ser Glu Asp Gly Glu Gln Ser Leu Ile
            180                 185                 190

Leu Ser Thr Ser Gln Thr Thr Ala Pro Asp Ala Pro Pro Asp Pro Thr
        195                 200                 205

Val Asp Gln Val Asp Asp Thr Ser Ile Val Val Arg Trp Ser Arg Pro
210                 215                 220

Gln Ala Pro Ile Thr Gly Tyr Arg Ile Val Tyr Ser Pro Ser Val Glu
225                 230                 235                 240

Gly Ser Ser Thr Glu Leu Asn Leu Pro Glu Thr Ala Asn Ser Val Thr
                245                 250                 255

Leu Ser Asp Leu Gln Pro Gly Val Gln Tyr Asn Ile Thr Ile Tyr Ala
            260                 265                 270

Val Glu Glu Asn Gln Glu Ser Thr Pro Val Val Ile Gln Gln Glu Thr
        275                 280                 285

Thr Gly Thr Pro Arg Ser Asp Gly Ser Ser Gly Ser Gly Ser Ser Ser
    290                 295                 300

Pro Thr Asp Leu Arg Phe Thr Asn Ile Gly Pro Asp Thr Met Arg Val
305                 310                 315                 320

Thr Trp Ala Pro Pro Pro Ser Ile Asp Leu Thr Asn Phe Leu Val Arg
                325                 330                 335

Tyr Ser Pro Val Lys Asn Glu Glu Asp Val Ala Glu Leu Ser Ile Ser
            340                 345                 350

Pro Ser Asp Asn Ala Val Val Leu Thr Asn Leu Leu Pro Gly Thr Glu
        355                 360                 365

Tyr Val Val Ser Val Ser Ser Val Tyr Glu Gln His Glu Ser Thr Pro
    370                 375                 380

Leu Arg Gly Arg Gln Lys Thr Gly Leu Asp Ser Pro Thr Gly Ile Asp
385                 390                 395                 400

Phe Ser Asp Ile Thr Ala Asn Ser Phe Thr Val His Trp Ile Ala Pro
                405                 410                 415
```

-continued

Arg Ala Thr Ile Thr Gly Tyr Arg Ile Arg His His Pro Glu His Phe
                420                 425                 430

Ser Gly Arg Pro Arg Glu Asp Arg Val Pro His Ser Arg Asn Ser Ile
                435                 440                 445

Thr Leu Thr Asn Leu Thr Pro Gly Thr Glu Tyr Val Val Ser Ile Val
            450                 455                 460

Ala Leu Asn Gly Arg Glu Glu Ser Pro Leu Leu Ile Gly Gln Gln Ser
465                 470                 475                 480

Thr Val Ser Asp Val Pro Arg Asp Leu Glu Val Val Ala Ala Thr Pro
                485                 490                 495

Thr Ser Leu Leu Ile Ser Trp Asp Ala Pro Ala Val Thr Val Arg Tyr
            500                 505                 510

Tyr Arg Ile Thr Tyr Gly Glu Thr Gly Gly Asn Ser Pro Val Gln Glu
            515                 520                 525

Phe Thr Val Pro Gly Ser Lys Ser Thr Ala Thr Ile Ser Gly Leu Lys
            530                 535                 540

Pro Gly Val Asp Tyr Thr Ile Thr Val Tyr Ala Val Thr Gly Arg Gly
545                 550                 555                 560

Asp Ser Pro Ala Ser Ser Lys Pro Ile Ser Ile Asn Tyr Arg Thr Glu
                565                 570                 575

Ile Asp Lys Pro Ser Met Ala Ile Pro Ala Pro Thr Asp Leu Lys Phe
            580                 585                 590

Thr Gln Val Thr Pro Thr Ser Leu Ser Ala Gln Trp Thr Pro Pro Asn
                595                 600                 605

Val Gln Leu Thr Gly Tyr Arg Val Arg Val Thr Pro Lys Glu Lys Thr
610                 615                 620

Gly Pro Met Lys Glu Ile Asn Leu Ala Pro Asp Ser Ser Ser Val Val
625                 630                 635                 640

Val Ser Gly Leu Met Val Ala Thr Lys Tyr Glu Val Ser Val Tyr Ala
                645                 650                 655

Leu Lys Asp Thr Leu Thr Ser Arg Pro Ala Gln Gly Val Val Thr Thr
                660                 665                 670

Leu Glu Asn Val Ser Pro Pro Arg Arg Ala Arg Val Thr Asp Ala Thr
            675                 680                 685

Glu Thr Thr Ile Thr Ile Ser Trp Arg Thr Lys Thr Glu Thr Ile Thr
            690                 695                 700

Gly Phe Gln Val Asp Ala Val Pro Ala Asn Gly Gln Thr Pro Ile Gln
705                 710                 715                 720

Arg Thr Ile Lys Pro Asp Val Arg Ser Tyr Thr Ile Thr Gly Leu Gln
                725                 730                 735

Pro Gly Thr Asp Tyr Lys Ile Tyr Leu Tyr Thr Leu Asn Asp Asn Ala
                740                 745                 750

Arg Ser Ser Pro Val Val Ile Asp Ala Ser Thr Ala Ile Asp Ala Pro
            755                 760                 765

Ser Asn Leu Arg Phe Leu Ala Thr Thr Pro Asn Ser Leu Leu Val Ser
            770                 775                 780

Trp Gln Pro Pro Arg Ala Arg Ile Thr Gly Tyr Ile Ile Lys Tyr Glu
785                 790                 795                 800

Lys Pro Gly Ser Pro Pro Arg Glu Val Val Pro Arg Pro Arg Pro Gly
                805                 810                 815

Val Thr Glu Ala Thr Ile Thr Gly Leu Glu Pro Gly Thr Glu Tyr Thr
            820                 825                 830

Ile Tyr Val Ile Ala Leu Lys Asn Asn Gln Lys Ser Glu Pro Leu Ile

```
                835                 840                 845
Gly Arg Lys Lys Thr Asp Glu Leu Pro Gln Leu Val Thr Leu Pro His
850                 855                 860
Pro Asn Leu His Gly Pro Glu Ile Leu Asp Val Pro Ser Thr
865                 870                 875

<210> SEQ ID NO 29
<211> LENGTH: 884
<212> TYPE: PRT
<213> ORGANISM: Artificial Sequence
<220> FEATURE:
<223> OTHER INFORMATION: N-terminal 3a.a. insertion of FCH-296

<400> SEQUENCE: 29

Met Pro Ser Ser Gly Pro Val Glu Val Phe Ile Thr Glu Thr Pro
1               5                   10                  15

Ser Gln Pro Asn Ser His Pro Ile Gln Trp Asn Ala Pro Gln Pro Ser
                20                  25                  30

His Ile Ser Lys Tyr Ile Leu Arg Trp Arg Pro Lys Asn Ser Val Gly
            35                  40                  45

Arg Trp Lys Glu Ala Thr Ile Pro Gly His Leu Asn Ser Tyr Thr Ile
50                  55                  60

Lys Gly Leu Lys Pro Gly Val Val Tyr Glu Gly Gln Leu Ile Ser Ile
65                  70                  75                  80

Gln Gln Tyr Gly His Gln Glu Val Thr Arg Phe Asp Phe Thr Thr Thr
                85                  90                  95

Ser Thr Ser Thr Pro Val Thr Ser Asn Thr Val Thr Gly Glu Thr Thr
            100                 105                 110

Pro Phe Ser Pro Leu Val Ala Thr Ser Glu Ser Val Thr Glu Ile Thr
        115                 120                 125

Ala Ser Ser Phe Val Val Ser Trp Val Ser Ala Ser Asp Thr Val Ser
130                 135                 140

Gly Phe Arg Val Glu Tyr Glu Leu Ser Glu Glu Gly Asp Glu Pro Gln
145                 150                 155                 160

Tyr Leu Asp Leu Pro Ser Thr Ala Thr Ser Val Asn Ile Pro Asp Leu
                165                 170                 175

Leu Pro Gly Arg Lys Tyr Ile Val Asn Val Tyr Gln Ile Ser Glu Asp
            180                 185                 190

Gly Glu Gln Ser Leu Ile Leu Ser Thr Ser Gln Thr Thr Ala Pro Asp
        195                 200                 205

Ala Pro Pro Asp Pro Thr Val Asp Gln Val Asp Asp Thr Ser Ile Val
210                 215                 220

Val Arg Trp Ser Arg Pro Gln Ala Pro Ile Thr Gly Tyr Arg Ile Val
225                 230                 235                 240

Tyr Ser Pro Ser Val Glu Gly Ser Ser Thr Glu Leu Asn Leu Pro Glu
                245                 250                 255

Thr Ala Asn Ser Val Thr Leu Ser Asp Leu Gln Pro Gly Val Gln Tyr
            260                 265                 270

Asn Ile Thr Ile Tyr Ala Val Glu Glu Asn Gln Glu Ser Thr Pro Val
        275                 280                 285

Val Ile Gln Gln Glu Thr Thr Gly Thr Pro Arg Ser Asp Gly Ser Ser
290                 295                 300

Gly Ser Ser Gly Ser Ser Pro Thr Asp Leu Arg Phe Thr Asn Ile Gly
305                 310                 315                 320

Pro Asp Thr Met Arg Val Thr Trp Ala Pro Pro Pro Ser Ile Asp Leu
```

```
                    325                 330                 335
Thr Asn Phe Leu Val Arg Tyr Ser Pro Val Lys Asn Glu Glu Asp Val
                340                 345                 350
Ala Glu Leu Ser Ile Ser Pro Ser Asp Asn Ala Val Val Leu Thr Asn
                355                 360                 365
Leu Leu Pro Gly Thr Glu Tyr Val Val Ser Val Ser Ser Val Tyr Glu
            370                 375                 380
Gln His Glu Ser Thr Pro Leu Arg Gly Arg Gln Lys Thr Gly Leu Asp
385                 390                 395                 400
Ser Pro Thr Gly Ile Asp Phe Ser Asp Ile Thr Ala Asn Ser Phe Thr
                405                 410                 415
Val His Trp Ile Ala Pro Arg Ala Thr Ile Thr Gly Tyr Arg Ile Arg
                420                 425                 430
His His Pro Glu His Phe Ser Gly Arg Pro Arg Glu Asp Arg Val Pro
                435                 440                 445
His Ser Arg Asn Ser Ile Thr Leu Thr Asn Leu Thr Pro Gly Thr Glu
                450                 455                 460
Tyr Val Val Ser Ile Val Ala Leu Asn Gly Arg Glu Glu Ser Pro Leu
465                 470                 475                 480
Leu Ile Gly Gln Gln Ser Thr Val Ser Asp Val Pro Arg Asp Leu Glu
                485                 490                 495
Val Val Ala Ala Thr Pro Thr Ser Leu Leu Ile Ser Trp Asp Ala Pro
                500                 505                 510
Ala Val Thr Val Arg Tyr Tyr Arg Ile Thr Tyr Gly Glu Thr Gly Gly
                515                 520                 525
Asn Ser Pro Val Gln Glu Phe Thr Val Pro Gly Ser Lys Ser Thr Ala
                530                 535                 540
Thr Ile Ser Gly Leu Lys Pro Gly Val Asp Tyr Thr Ile Thr Val Tyr
545                 550                 555                 560
Ala Val Thr Gly Arg Gly Asp Ser Pro Ala Ser Ser Lys Pro Ile Ser
                565                 570                 575
Ile Asn Tyr Arg Thr Glu Ile Asp Lys Pro Ser Met Ala Ile Pro Ala
                580                 585                 590
Pro Thr Asp Leu Lys Phe Thr Gln Val Thr Pro Thr Ser Leu Ser Ala
                595                 600                 605
Gln Trp Thr Pro Pro Asn Val Gln Leu Thr Gly Tyr Arg Val Arg Val
                610                 615                 620
Thr Pro Lys Glu Lys Thr Gly Pro Met Lys Glu Ile Asn Leu Ala Pro
625                 630                 635                 640
Asp Ser Ser Ser Val Val Val Ser Gly Leu Met Val Ala Thr Lys Tyr
                645                 650                 655
Glu Val Ser Val Tyr Ala Leu Lys Asp Thr Leu Thr Ser Arg Pro Ala
                660                 665                 670
Gln Gly Val Val Thr Thr Leu Glu Asn Val Ser Pro Pro Arg Arg Ala
                675                 680                 685
Arg Val Thr Asp Ala Thr Glu Thr Thr Ile Thr Ile Ser Trp Arg Thr
                690                 695                 700
Lys Thr Glu Thr Ile Thr Gly Phe Gln Val Asp Ala Val Pro Ala Asn
705                 710                 715                 720
Gly Gln Thr Pro Ile Gln Arg Thr Ile Lys Pro Asp Val Arg Ser Tyr
                725                 730                 735
Thr Ile Thr Gly Leu Gln Pro Gly Thr Asp Tyr Lys Ile Tyr Leu Tyr
                740                 745                 750
```

```
Thr Leu Asn Asp Asn Ala Arg Ser Ser Pro Val Val Ile Asp Ala Ser
        755                 760                 765

Thr Ala Ile Asp Ala Pro Ser Asn Leu Arg Phe Leu Ala Thr Thr Pro
770                 775                 780

Asn Ser Leu Leu Val Ser Trp Gln Pro Arg Ala Arg Ile Thr Gly
785                 790                 795                 800

Tyr Ile Ile Lys Tyr Glu Lys Pro Gly Ser Pro Arg Glu Val Val
            805                 810                 815

Pro Arg Pro Arg Pro Gly Val Thr Glu Ala Thr Ile Thr Gly Leu Glu
                820                 825                 830

Pro Gly Thr Glu Tyr Thr Ile Tyr Val Ile Ala Leu Lys Asn Asn Gln
        835                 840                 845

Lys Ser Glu Pro Leu Ile Gly Arg Lys Lys Thr Asp Glu Leu Pro Gln
850                 855                 860

Leu Val Thr Leu Pro His Pro Asn Leu His Gly Pro Glu Ile Leu Asp
865                 870                 875                 880

Val Pro Ser Thr
```

<210> SEQ ID NO 30
<211> LENGTH: 887
<212> TYPE: PRT
<213> ORGANISM: Artificial Sequence
<220> FEATURE:
<223> OTHER INFORMATION: N-terminal 6a.a. insertion of FCH-296

<400> SEQUENCE: 30

```
Met Gln Thr Tyr Pro Ser Ser Gly Pro Val Glu Val Phe Ile Thr
1               5                   10                  15

Glu Thr Pro Ser Gln Pro Asn Ser His Pro Ile Gln Trp Asn Ala Pro
            20                  25                  30

Gln Pro Ser His Ile Ser Lys Tyr Ile Leu Arg Trp Arg Pro Lys Asn
        35                  40                  45

Ser Val Gly Arg Trp Lys Glu Ala Thr Ile Pro Gly His Leu Asn Ser
    50                  55                  60

Tyr Thr Ile Lys Gly Leu Lys Pro Gly Val Val Tyr Glu Gly Gln Leu
65                  70                  75                  80

Ile Ser Ile Gln Gln Tyr Gly His Gln Glu Val Thr Arg Phe Asp Phe
                85                  90                  95

Thr Thr Thr Ser Thr Ser Thr Pro Val Thr Ser Asn Thr Val Thr Gly
            100                 105                 110

Glu Thr Thr Pro Phe Ser Pro Leu Val Ala Thr Ser Glu Ser Val Thr
        115                 120                 125

Glu Ile Thr Ala Ser Ser Phe Val Val Ser Trp Val Ser Ala Ser Asp
    130                 135                 140

Thr Val Ser Gly Phe Arg Val Glu Tyr Glu Leu Ser Glu Glu Gly Asp
145                 150                 155                 160

Glu Pro Gln Tyr Leu Asp Leu Pro Ser Thr Ala Thr Ser Val Asn Ile
                165                 170                 175

Pro Asp Leu Leu Pro Gly Arg Lys Tyr Ile Val Asn Val Tyr Gln Ile
            180                 185                 190

Ser Glu Asp Gly Glu Gln Ser Leu Ile Leu Ser Thr Ser Gln Thr Thr
        195                 200                 205

Ala Pro Asp Ala Pro Pro Asp Pro Thr Val Asp Gln Val Asp Asp Thr
    210                 215                 220
```

```
Ser Ile Val Val Arg Trp Ser Arg Pro Gln Ala Pro Ile Thr Gly Tyr
225                 230                 235                 240

Arg Ile Val Tyr Ser Pro Ser Val Glu Gly Ser Ser Thr Glu Leu Asn
            245                 250                 255

Leu Pro Glu Thr Ala Asn Ser Val Thr Leu Ser Asp Leu Gln Pro Gly
        260                 265                 270

Val Gln Tyr Asn Ile Thr Ile Tyr Ala Val Glu Glu Asn Gln Glu Ser
    275                 280                 285

Thr Pro Val Val Ile Gln Gln Glu Thr Thr Gly Thr Pro Arg Ser Asp
290                 295                 300

Gly Ser Ser Gly Ser Ser Gly Ser Ser Pro Thr Asp Leu Arg Phe Thr
305                 310                 315                 320

Asn Ile Gly Pro Asp Thr Met Arg Val Thr Trp Ala Pro Pro Ser
                325                 330                 335

Ile Asp Leu Thr Asn Phe Leu Val Arg Tyr Ser Pro Val Lys Asn Glu
            340                 345                 350

Glu Asp Val Ala Glu Leu Ser Ile Ser Pro Ser Asp Asn Ala Val Val
        355                 360                 365

Leu Thr Asn Leu Leu Pro Gly Thr Glu Tyr Val Val Ser Val Ser Ser
370                 375                 380

Val Tyr Glu Gln His Glu Ser Thr Pro Leu Arg Gly Arg Gln Lys Thr
385                 390                 395                 400

Gly Leu Asp Ser Pro Thr Gly Ile Asp Phe Ser Asp Ile Thr Ala Asn
                405                 410                 415

Ser Phe Thr Val His Trp Ile Ala Pro Arg Ala Thr Ile Thr Gly Tyr
            420                 425                 430

Arg Ile Arg His His Pro Glu His Phe Ser Gly Arg Pro Arg Glu Asp
        435                 440                 445

Arg Val Pro His Ser Arg Asn Ser Ile Thr Leu Thr Asn Leu Thr Pro
    450                 455                 460

Gly Thr Glu Tyr Val Val Ser Ile Val Ala Leu Asn Gly Arg Glu Glu
465                 470                 475                 480

Ser Pro Leu Leu Ile Gly Gln Gln Ser Thr Val Ser Asp Val Pro Arg
                485                 490                 495

Asp Leu Glu Val Val Ala Ala Thr Pro Thr Ser Leu Leu Ile Ser Trp
            500                 505                 510

Asp Ala Pro Ala Val Thr Val Arg Tyr Tyr Arg Ile Thr Tyr Gly Glu
        515                 520                 525

Thr Gly Gly Asn Ser Pro Val Gln Glu Phe Thr Val Pro Gly Ser Lys
    530                 535                 540

Ser Thr Ala Thr Ile Ser Gly Leu Lys Pro Gly Val Asp Tyr Thr Ile
545                 550                 555                 560

Thr Val Tyr Ala Val Thr Gly Arg Gly Asp Ser Pro Ala Ser Ser Lys
                565                 570                 575

Pro Ile Ser Ile Asn Tyr Arg Thr Glu Ile Asp Lys Pro Ser Met Ala
            580                 585                 590

Ile Pro Ala Pro Thr Asp Leu Lys Phe Thr Gln Val Thr Pro Thr Ser
        595                 600                 605

Leu Ser Ala Gln Trp Thr Pro Pro Asn Val Gln Leu Thr Gly Tyr Arg
    610                 615                 620

Val Arg Val Thr Pro Lys Glu Lys Thr Gly Pro Met Lys Glu Ile Asn
625                 630                 635                 640

Leu Ala Pro Asp Ser Ser Ser Val Val Ser Gly Leu Met Val Ala
```

```
                        645                 650                 655
Thr Lys Tyr Glu Val Ser Val Tyr Ala Leu Lys Asp Thr Leu Thr Ser
            660                 665                 670

Arg Pro Ala Gln Gly Val Val Thr Leu Glu Asn Val Ser Pro Pro
        675                 680                 685

Arg Arg Ala Arg Val Thr Asp Ala Thr Glu Thr Thr Ile Thr Ile Ser
690                 695                 700

Trp Arg Thr Lys Thr Glu Thr Ile Thr Gly Phe Gln Val Asp Ala Val
705                 710                 715                 720

Pro Ala Asn Gly Gln Thr Pro Ile Gln Arg Thr Ile Lys Pro Asp Val
                725                 730                 735

Arg Ser Tyr Thr Ile Thr Gly Leu Gln Pro Gly Thr Asp Tyr Lys Ile
            740                 745                 750

Tyr Leu Tyr Thr Leu Asn Asp Asn Ala Arg Ser Ser Pro Val Val Ile
            755                 760                 765

Asp Ala Ser Thr Ala Ile Asp Ala Pro Ser Asn Leu Arg Phe Leu Ala
            770                 775                 780

Thr Thr Pro Asn Ser Leu Leu Val Ser Trp Gln Pro Pro Arg Ala Arg
785                 790                 795                 800

Ile Thr Gly Tyr Ile Ile Lys Tyr Glu Lys Pro Gly Ser Pro Pro Arg
                805                 810                 815

Glu Val Val Pro Arg Pro Arg Pro Gly Val Thr Glu Ala Thr Ile Thr
                820                 825                 830

Gly Leu Glu Pro Gly Thr Glu Tyr Thr Ile Tyr Val Ile Ala Leu Lys
            835                 840                 845

Asn Asn Gln Lys Ser Glu Pro Leu Ile Gly Arg Lys Lys Thr Asp Glu
            850                 855                 860

Leu Pro Gln Leu Val Thr Leu Pro His Pro Asn Leu His Gly Pro Glu
865                 870                 875                 880

Ile Leu Asp Val Pro Ser Thr
                885

<210> SEQ ID NO 31
<211> LENGTH: 890
<212> TYPE: PRT
<213> ORGANISM: Artificial Sequence
<220> FEATURE:
<223> OTHER INFORMATION: N-terminal 9a.a. insertion of FCH-296

<400> SEQUENCE: 31

Met Gln Pro Leu Gln Thr Tyr Pro Ser Ser Gly Pro Val Glu Val
1               5                   10                  15

Phe Ile Thr Glu Thr Pro Ser Gln Pro Asn Ser His Pro Ile Gln Trp
            20                  25                  30

Asn Ala Pro Gln Pro Ser His Ile Ser Lys Tyr Ile Leu Arg Trp Arg
        35                  40                  45

Pro Lys Asn Ser Val Gly Arg Trp Lys Glu Ala Thr Ile Pro Gly His
    50                  55                  60

Leu Asn Ser Tyr Thr Ile Lys Gly Leu Lys Pro Gly Val Val Tyr Glu
65                  70                  75                  80

Gly Gln Leu Ile Ser Ile Gln Gln Tyr Gly His Gln Glu Val Thr Arg
                85                  90                  95

Phe Asp Phe Thr Thr Thr Ser Thr Ser Thr Pro Val Thr Ser Asn Thr
            100                 105                 110

Val Thr Gly Glu Thr Thr Pro Phe Ser Pro Leu Val Ala Thr Ser Glu
```

```
            115                 120                 125
Ser Val Thr Glu Ile Thr Ala Ser Ser Phe Val Ser Trp Val Ser
        130                 135                 140
Ala Ser Asp Thr Val Ser Gly Phe Arg Val Glu Tyr Glu Leu Ser Glu
145                 150                 155                 160
Glu Gly Asp Glu Pro Gln Tyr Leu Asp Leu Pro Ser Thr Ala Thr Ser
                165                 170                 175
Val Asn Ile Pro Asp Leu Leu Pro Gly Arg Lys Tyr Ile Val Asn Val
                180                 185                 190
Tyr Gln Ile Ser Glu Asp Gly Glu Gln Ser Leu Ile Leu Ser Thr Ser
            195                 200                 205
Gln Thr Thr Ala Pro Asp Ala Pro Pro Asp Pro Thr Val Asp Gln Val
        210                 215                 220
Asp Asp Thr Ser Ile Val Val Arg Trp Ser Arg Pro Gln Ala Pro Ile
225                 230                 235                 240
Thr Gly Tyr Arg Ile Val Tyr Ser Pro Ser Val Glu Gly Ser Ser Thr
                245                 250                 255
Glu Leu Asn Leu Pro Glu Thr Ala Asn Ser Val Thr Leu Ser Asp Leu
            260                 265                 270
Gln Pro Gly Val Gln Tyr Asn Ile Thr Ile Tyr Ala Val Glu Glu Asn
        275                 280                 285
Gln Glu Ser Thr Pro Val Val Ile Gln Gln Glu Thr Thr Gly Thr Pro
    290                 295                 300
Arg Ser Asp Gly Ser Ser Gly Ser Ser Gly Ser Ser Pro Thr Asp Leu
305                 310                 315                 320
Arg Phe Thr Asn Ile Gly Pro Asp Thr Met Arg Val Thr Trp Ala Pro
                325                 330                 335
Pro Pro Ser Ile Asp Leu Thr Asn Phe Leu Val Arg Tyr Ser Pro Val
                340                 345                 350
Lys Asn Glu Glu Asp Val Ala Glu Leu Ser Ile Ser Pro Ser Asp Asn
            355                 360                 365
Ala Val Val Leu Thr Asn Leu Leu Pro Gly Thr Glu Tyr Val Val Ser
        370                 375                 380
Val Ser Ser Val Tyr Glu Gln His Glu Ser Thr Pro Leu Arg Gly Arg
385                 390                 395                 400
Gln Lys Thr Gly Leu Asp Ser Pro Thr Gly Ile Asp Phe Ser Asp Ile
                405                 410                 415
Thr Ala Asn Ser Phe Thr Val His Trp Ile Ala Pro Arg Ala Thr Ile
                420                 425                 430
Thr Gly Tyr Arg Ile Arg His His Pro Glu His Phe Ser Gly Arg Pro
            435                 440                 445
Arg Glu Asp Arg Val Pro His Ser Arg Asn Ser Ile Thr Leu Thr Asn
        450                 455                 460
Leu Thr Pro Gly Thr Glu Tyr Val Val Ser Ile Val Ala Leu Asn Gly
465                 470                 475                 480
Arg Glu Glu Ser Pro Leu Leu Ile Gly Gln Gln Ser Thr Val Ser Asp
                485                 490                 495
Val Pro Arg Asp Leu Glu Val Val Ala Ala Thr Pro Thr Ser Leu Leu
            500                 505                 510
Ile Ser Trp Asp Ala Pro Ala Val Thr Val Arg Tyr Tyr Arg Ile Thr
        515                 520                 525
Tyr Gly Glu Thr Gly Gly Asn Ser Pro Val Gln Glu Phe Thr Val Pro
    530                 535                 540
```

Gly Ser Lys Ser Thr Ala Thr Ile Ser Gly Leu Lys Pro Gly Val Asp
545                 550                 555                 560

Tyr Thr Ile Thr Val Tyr Ala Val Thr Gly Arg Gly Asp Ser Pro Ala
                565                 570                 575

Ser Ser Lys Pro Ile Ser Ile Asn Tyr Arg Thr Glu Ile Asp Lys Pro
            580                 585                 590

Ser Met Ala Ile Pro Ala Pro Thr Asp Leu Lys Phe Thr Gln Val Thr
        595                 600                 605

Pro Thr Ser Leu Ser Ala Gln Trp Thr Pro Pro Asn Val Gln Leu Thr
    610                 615                 620

Gly Tyr Arg Val Arg Val Thr Pro Lys Glu Lys Thr Gly Pro Met Lys
625                 630                 635                 640

Glu Ile Asn Leu Ala Pro Asp Ser Ser Ser Val Val Val Ser Gly Leu
                645                 650                 655

Met Val Ala Thr Lys Tyr Glu Val Ser Val Tyr Ala Leu Lys Asp Thr
                660                 665                 670

Leu Thr Ser Arg Pro Ala Gln Gly Val Val Thr Thr Leu Glu Asn Val
        675                 680                 685

Ser Pro Pro Arg Arg Ala Arg Val Thr Asp Ala Thr Glu Thr Thr Ile
    690                 695                 700

Thr Ile Ser Trp Arg Thr Lys Thr Glu Thr Ile Thr Gly Phe Gln Val
705                 710                 715                 720

Asp Ala Val Pro Ala Asn Gly Gln Thr Pro Ile Gln Arg Thr Ile Lys
                725                 730                 735

Pro Asp Val Arg Ser Tyr Thr Ile Thr Gly Leu Gln Pro Gly Thr Asp
                740                 745                 750

Tyr Lys Ile Tyr Leu Tyr Thr Leu Asn Asp Asn Ala Arg Ser Ser Pro
        755                 760                 765

Val Val Ile Asp Ala Ser Thr Ala Ile Asp Ala Pro Ser Asn Leu Arg
    770                 775                 780

Phe Leu Ala Thr Thr Pro Asn Ser Leu Leu Val Ser Trp Gln Pro Pro
785                 790                 795                 800

Arg Ala Arg Ile Thr Gly Tyr Ile Ile Lys Tyr Glu Lys Pro Gly Ser
                805                 810                 815

Pro Pro Arg Glu Val Val Pro Arg Pro Arg Pro Gly Val Thr Glu Ala
                820                 825                 830

Thr Ile Thr Gly Leu Glu Pro Gly Thr Glu Tyr Thr Ile Tyr Val Ile
        835                 840                 845

Ala Leu Lys Asn Asn Gln Lys Ser Glu Pro Leu Ile Gly Arg Lys Lys
    850                 855                 860

Thr Asp Glu Leu Pro Gln Leu Val Thr Leu Pro His Pro Asn Leu His
865                 870                 875                 880

Gly Pro Glu Ile Leu Asp Val Pro Ser Thr
                885                 890

<210> SEQ ID NO 32
<211> LENGTH: 892
<212> TYPE: PRT
<213> ORGANISM: Artificial Sequence
<220> FEATURE:
<223> OTHER INFORMATION: N-terminal 11a.a. insertion of FCH-296

<400> SEQUENCE: 32

Met His Cys Gln Pro Leu Gln Thr Tyr Pro Ser Ser Ser Gly Pro Val
1               5                   10                  15

-continued

```
Glu Val Phe Ile Thr Glu Thr Pro Ser Gln Pro Asn Ser His Pro Ile
             20                  25                  30

Gln Trp Asn Ala Pro Gln Pro Ser His Ile Ser Lys Tyr Ile Leu Arg
         35                  40                  45

Trp Arg Pro Lys Asn Ser Val Gly Arg Trp Lys Glu Ala Thr Ile Pro
 50                  55                  60

Gly His Leu Asn Ser Tyr Thr Ile Lys Gly Leu Lys Pro Gly Val Val
 65                  70                  75                  80

Tyr Glu Gly Gln Leu Ile Ser Ile Gln Gln Tyr Gly His Gln Glu Val
                 85                  90                  95

Thr Arg Phe Asp Phe Thr Thr Thr Ser Thr Ser Thr Pro Val Thr Ser
            100                 105                 110

Asn Thr Val Thr Gly Glu Thr Thr Pro Phe Ser Pro Leu Val Ala Thr
        115                 120                 125

Ser Glu Ser Val Thr Glu Ile Thr Ala Ser Ser Phe Val Val Ser Trp
130                 135                 140

Val Ser Ala Ser Asp Thr Val Ser Gly Phe Arg Val Glu Tyr Glu Leu
145                 150                 155                 160

Ser Glu Glu Gly Asp Glu Pro Gln Tyr Leu Asp Leu Pro Ser Thr Ala
                165                 170                 175

Thr Ser Val Asn Ile Pro Asp Leu Leu Pro Gly Arg Lys Tyr Ile Val
            180                 185                 190

Asn Val Tyr Gln Ile Ser Glu Asp Gly Glu Gln Ser Leu Ile Leu Ser
        195                 200                 205

Thr Ser Gln Thr Thr Ala Pro Asp Ala Pro Pro Asp Pro Thr Val Asp
210                 215                 220

Gln Val Asp Asp Thr Ser Ile Val Val Arg Trp Ser Arg Pro Gln Ala
225                 230                 235                 240

Pro Ile Thr Gly Tyr Arg Ile Val Tyr Ser Pro Ser Val Glu Gly Ser
                245                 250                 255

Ser Thr Glu Leu Asn Leu Pro Glu Thr Ala Asn Ser Val Thr Leu Ser
            260                 265                 270

Asp Leu Gln Pro Gly Val Gln Tyr Asn Ile Thr Ile Tyr Ala Val Glu
        275                 280                 285

Glu Asn Gln Glu Ser Thr Pro Val Val Ile Gln Gln Glu Thr Thr Gly
290                 295                 300

Thr Pro Arg Ser Asp Gly Ser Ser Gly Ser Ser Gly Ser Ser Pro Thr
305                 310                 315                 320

Asp Leu Arg Phe Thr Asn Ile Gly Pro Asp Thr Met Arg Val Thr Trp
                325                 330                 335

Ala Pro Pro Pro Ser Ile Asp Leu Thr Asn Phe Leu Val Arg Tyr Ser
            340                 345                 350

Pro Val Lys Asn Glu Glu Asp Val Ala Glu Leu Ser Ile Ser Pro Ser
        355                 360                 365

Asp Asn Ala Val Val Leu Thr Asn Leu Leu Pro Gly Thr Glu Tyr Val
370                 375                 380

Val Ser Val Ser Ser Val Tyr Glu Gln His Glu Ser Thr Pro Leu Arg
385                 390                 395                 400

Gly Arg Gln Lys Thr Gly Leu Asp Ser Pro Thr Gly Ile Asp Phe Ser
                405                 410                 415

Asp Ile Thr Ala Asn Ser Phe Thr Val His Trp Ile Ala Pro Arg Ala
            420                 425                 430
```

```
Thr Ile Thr Gly Tyr Arg Ile Arg His His Pro Glu His Phe Ser Gly
            435                 440                 445

Arg Pro Arg Glu Asp Arg Val Pro His Ser Arg Asn Ser Ile Thr Leu
450                 455                 460

Thr Asn Leu Thr Pro Gly Thr Glu Tyr Val Val Ser Ile Val Ala Leu
465                 470                 475                 480

Asn Gly Arg Glu Glu Ser Pro Leu Leu Ile Gly Gln Gln Ser Thr Val
                485                 490                 495

Ser Asp Val Pro Arg Asp Leu Glu Val Val Ala Ala Thr Pro Thr Ser
                500                 505                 510

Leu Leu Ile Ser Trp Asp Ala Pro Ala Val Thr Val Arg Tyr Tyr Arg
            515                 520                 525

Ile Thr Tyr Gly Glu Thr Gly Gly Asn Ser Pro Val Gln Glu Phe Thr
        530                 535                 540

Val Pro Gly Ser Lys Ser Thr Ala Thr Ile Ser Gly Leu Lys Pro Gly
545                 550                 555                 560

Val Asp Tyr Thr Ile Thr Val Tyr Ala Val Thr Gly Arg Gly Asp Ser
                565                 570                 575

Pro Ala Ser Ser Lys Pro Ile Ser Ile Asn Tyr Arg Thr Glu Ile Asp
                580                 585                 590

Lys Pro Ser Met Ala Ile Pro Ala Pro Thr Asp Leu Lys Phe Thr Gln
            595                 600                 605

Val Thr Pro Thr Ser Leu Ser Ala Gln Trp Thr Pro Pro Asn Val Gln
        610                 615                 620

Leu Thr Gly Tyr Arg Val Arg Val Thr Pro Lys Glu Lys Thr Gly Pro
625                 630                 635                 640

Met Lys Glu Ile Asn Leu Ala Pro Asp Ser Ser Ser Val Val Val Ser
                645                 650                 655

Gly Leu Met Val Ala Thr Lys Tyr Glu Val Ser Val Tyr Ala Leu Lys
            660                 665                 670

Asp Thr Leu Thr Ser Arg Pro Ala Gln Gly Val Val Thr Thr Leu Glu
        675                 680                 685

Asn Val Ser Pro Pro Arg Arg Ala Arg Val Thr Asp Ala Thr Glu Thr
690                 695                 700

Thr Ile Thr Ile Ser Trp Arg Thr Lys Thr Glu Thr Ile Thr Gly Phe
705                 710                 715                 720

Gln Val Asp Ala Val Pro Ala Asn Gly Gln Thr Pro Ile Gln Arg Thr
                725                 730                 735

Ile Lys Pro Asp Val Arg Ser Tyr Thr Ile Thr Gly Leu Gln Pro Gly
            740                 745                 750

Thr Asp Tyr Lys Ile Tyr Leu Tyr Thr Leu Asn Asp Asn Ala Arg Ser
        755                 760                 765

Ser Pro Val Val Ile Asp Ala Ser Thr Ala Ile Asp Ala Pro Ser Asn
770                 775                 780

Leu Arg Phe Leu Ala Thr Thr Pro Asn Ser Leu Leu Val Ser Trp Gln
785                 790                 795                 800

Pro Pro Arg Ala Arg Ile Thr Gly Tyr Ile Ile Lys Tyr Glu Lys Pro
                805                 810                 815

Gly Ser Pro Pro Arg Glu Val Val Pro Arg Pro Arg Pro Gly Val Thr
            820                 825                 830

Glu Ala Thr Ile Thr Gly Leu Glu Pro Gly Thr Glu Tyr Thr Ile Tyr
        835                 840                 845

Val Ile Ala Leu Lys Asn Asn Gln Lys Ser Glu Pro Leu Ile Gly Arg
```

```
                    850                 855                 860
Lys Lys Thr Asp Glu Leu Pro Gln Leu Val Thr Leu Pro His Pro Asn
865                 870                 875                 880

Leu His Gly Pro Glu Ile Leu Asp Val Pro Ser Thr
                885                 890

<210> SEQ ID NO 33
<211> LENGTH: 893
<212> TYPE: PRT
<213> ORGANISM: Artificial Sequence
<220> FEATURE:
<223> OTHER INFORMATION: N-terminal 12a.a. insertion of FCH-296

<400> SEQUENCE: 33

Met Trp His Cys Gln Pro Leu Gln Thr Tyr Pro Ser Ser Gly Pro
1               5                   10                  15

Val Glu Val Phe Ile Thr Glu Thr Pro Ser Gln Pro Asn Ser His Pro
                20                  25                  30

Ile Gln Trp Asn Ala Pro Gln Pro Ser His Ile Ser Lys Tyr Ile Leu
            35                  40                  45

Arg Trp Arg Pro Lys Asn Ser Val Gly Arg Trp Lys Glu Ala Thr Ile
50                  55                  60

Pro Gly His Leu Asn Ser Tyr Thr Ile Lys Gly Leu Lys Pro Gly Val
65                  70                  75                  80

Val Tyr Glu Gly Gln Leu Ile Ser Ile Gln Gln Tyr Gly His Gln Glu
                85                  90                  95

Val Thr Arg Phe Asp Phe Thr Thr Ser Thr Ser Thr Pro Val Thr
                100                 105                 110

Ser Asn Thr Val Thr Gly Glu Thr Thr Pro Phe Ser Pro Leu Val Ala
            115                 120                 125

Thr Ser Glu Ser Val Thr Glu Ile Thr Ala Ser Ser Phe Val Val Ser
130                 135                 140

Trp Val Ser Ala Ser Asp Thr Val Ser Gly Phe Arg Val Glu Tyr Glu
145                 150                 155                 160

Leu Ser Glu Glu Gly Asp Glu Pro Gln Tyr Leu Asp Leu Pro Ser Thr
                165                 170                 175

Ala Thr Ser Val Asn Ile Pro Asp Leu Leu Pro Gly Arg Lys Tyr Ile
            180                 185                 190

Val Asn Val Tyr Gln Ile Ser Glu Asp Gly Glu Gln Ser Leu Ile Leu
        195                 200                 205

Ser Thr Ser Gln Thr Thr Ala Pro Asp Ala Pro Pro Asp Pro Thr Val
210                 215                 220

Asp Gln Val Asp Asp Thr Ser Ile Val Val Arg Trp Ser Arg Pro Gln
225                 230                 235                 240

Ala Pro Ile Thr Gly Tyr Arg Ile Val Tyr Ser Pro Ser Val Glu Gly
                245                 250                 255

Ser Ser Thr Glu Leu Asn Leu Pro Glu Thr Ala Asn Ser Val Thr Leu
            260                 265                 270

Ser Asp Leu Gln Pro Gly Val Gln Tyr Asn Ile Thr Ile Tyr Ala Val
        275                 280                 285

Glu Glu Asn Gln Glu Ser Thr Pro Val Val Ile Gln Gln Glu Thr Thr
290                 295                 300

Gly Thr Pro Arg Ser Asp Gly Ser Ser Gly Ser Gly Ser Ser Pro
305                 310                 315                 320

Thr Asp Leu Arg Phe Thr Asn Ile Gly Pro Asp Thr Met Arg Val Thr
```

```
                    325                 330                 335
Trp Ala Pro Pro Pro Ser Ile Asp Leu Thr Asn Phe Leu Val Arg Tyr
            340                 345                 350
Ser Pro Val Lys Asn Glu Glu Asp Val Ala Glu Leu Ser Ile Ser Pro
            355                 360                 365
Ser Asp Asn Ala Val Val Leu Thr Asn Leu Leu Pro Gly Thr Glu Tyr
            370                 375                 380
Val Val Ser Val Ser Ser Val Tyr Glu Gln His Glu Ser Thr Pro Leu
385                 390                 395                 400
Arg Gly Arg Gln Lys Thr Gly Leu Asp Ser Pro Thr Gly Ile Asp Phe
            405                 410                 415
Ser Asp Ile Thr Ala Asn Ser Phe Thr Val His Trp Ile Ala Pro Arg
            420                 425                 430
Ala Thr Ile Thr Gly Tyr Arg Ile Arg His His Pro Glu His Phe Ser
            435                 440                 445
Gly Arg Pro Arg Glu Asp Arg Val Pro His Ser Arg Asn Ser Ile Thr
            450                 455                 460
Leu Thr Asn Leu Thr Pro Gly Thr Glu Tyr Val Val Ser Ile Val Ala
465                 470                 475                 480
Leu Asn Gly Arg Glu Glu Ser Pro Leu Leu Ile Gly Gln Gln Ser Thr
            485                 490                 495
Val Ser Asp Val Pro Arg Asp Leu Glu Val Val Ala Ala Thr Pro Thr
            500                 505                 510
Ser Leu Leu Ile Ser Trp Asp Ala Pro Ala Val Thr Val Arg Tyr Tyr
            515                 520                 525
Arg Ile Thr Tyr Gly Glu Thr Gly Gly Asn Ser Pro Val Gln Glu Phe
            530                 535                 540
Thr Val Pro Gly Ser Lys Ser Thr Ala Thr Ile Ser Gly Leu Lys Pro
545                 550                 555                 560
Gly Val Asp Tyr Thr Ile Thr Val Tyr Ala Val Thr Gly Arg Gly Asp
            565                 570                 575
Ser Pro Ala Ser Ser Lys Pro Ile Ser Ile Asn Tyr Arg Thr Glu Ile
            580                 585                 590
Asp Lys Pro Ser Met Ala Ile Pro Ala Pro Thr Asp Leu Lys Phe Thr
            595                 600                 605
Gln Val Thr Pro Thr Ser Leu Ser Ala Gln Trp Thr Pro Pro Asn Val
            610                 615                 620
Gln Leu Thr Gly Tyr Arg Val Arg Val Thr Pro Lys Glu Lys Thr Gly
625                 630                 635                 640
Pro Met Lys Glu Ile Asn Leu Ala Pro Asp Ser Ser Ser Val Val Val
            645                 650                 655
Ser Gly Leu Met Val Ala Thr Lys Tyr Glu Val Ser Val Tyr Ala Leu
            660                 665                 670
Lys Asp Thr Leu Thr Ser Arg Pro Ala Gln Gly Val Val Thr Thr Leu
            675                 680                 685
Glu Asn Val Ser Pro Pro Arg Arg Ala Arg Val Thr Asp Ala Thr Glu
            690                 695                 700
Thr Thr Ile Thr Ile Ser Trp Arg Thr Lys Thr Glu Thr Ile Thr Gly
705                 710                 715                 720
Phe Gln Val Asp Ala Val Pro Ala Asn Gly Gln Thr Pro Ile Gln Arg
            725                 730                 735
Thr Ile Lys Pro Asp Val Arg Ser Tyr Thr Ile Thr Gly Leu Gln Pro
            740                 745                 750
```

```
Gly Thr Asp Tyr Lys Ile Tyr Leu Tyr Thr Leu Asn Asp Asn Ala Arg
            755                 760                 765

Ser Ser Pro Val Val Ile Asp Ala Ser Thr Ala Ile Asp Ala Pro Ser
770                 775                 780

Asn Leu Arg Phe Leu Ala Thr Thr Pro Asn Ser Leu Leu Val Ser Trp
785                 790                 795                 800

Gln Pro Pro Arg Ala Arg Ile Thr Gly Tyr Ile Ile Lys Tyr Glu Lys
            805                 810                 815

Pro Gly Ser Pro Pro Arg Glu Val Val Pro Arg Pro Arg Pro Gly Val
                820                 825                 830

Thr Glu Ala Thr Ile Thr Gly Leu Glu Pro Gly Thr Glu Tyr Thr Ile
            835                 840                 845

Tyr Val Ile Ala Leu Lys Asn Asn Gln Lys Ser Glu Pro Leu Ile Gly
        850                 855                 860

Arg Lys Lys Thr Asp Glu Leu Pro Gln Leu Val Thr Leu Pro His Pro
865                 870                 875                 880

Asn Leu His Gly Pro Glu Ile Leu Asp Val Pro Ser Thr
                885                 890

<210> SEQ ID NO 34
<211> LENGTH: 895
<212> TYPE: PRT
<213> ORGANISM: Artificial Sequence
<220> FEATURE:
<223> OTHER INFORMATION: N-terminal 14a.a. insertion of FCH-296

<400> SEQUENCE: 34

Met Gly Glu Trp His Cys Gln Pro Leu Gln Thr Tyr Pro Ser Ser Ser
1               5                   10                  15

Gly Pro Val Glu Val Phe Ile Thr Glu Thr Pro Ser Gln Pro Asn Ser
            20                  25                  30

His Pro Ile Gln Trp Asn Ala Pro Gln Pro Ser His Ile Ser Lys Tyr
        35                  40                  45

Ile Leu Arg Trp Arg Pro Lys Asn Ser Val Gly Arg Trp Lys Glu Ala
    50                  55                  60

Thr Ile Pro Gly His Leu Asn Ser Tyr Thr Ile Lys Gly Leu Lys Pro
65                  70                  75                  80

Gly Val Val Tyr Glu Gly Gln Leu Ile Ser Ile Gln Gln Tyr Gly His
            85                  90                  95

Gln Glu Val Thr Arg Phe Asp Phe Thr Thr Ser Thr Ser Thr Pro
            100                 105                 110

Val Thr Ser Asn Thr Val Thr Gly Glu Thr Thr Pro Phe Ser Pro Leu
            115                 120                 125

Val Ala Thr Ser Glu Ser Val Thr Glu Ile Thr Ala Ser Ser Phe Val
            130                 135                 140

Val Ser Trp Val Ser Ala Ser Asp Thr Val Ser Gly Phe Arg Val Glu
145                 150                 155                 160

Tyr Glu Leu Ser Glu Glu Gly Asp Glu Pro Gln Tyr Leu Asp Leu Pro
            165                 170                 175

Ser Thr Ala Thr Ser Val Asn Ile Pro Asp Leu Leu Pro Gly Arg Lys
            180                 185                 190

Tyr Ile Val Asn Val Tyr Gln Ile Ser Glu Asp Gly Glu Gln Ser Leu
        195                 200                 205

Ile Leu Ser Thr Ser Gln Thr Thr Ala Pro Asp Ala Pro Pro Asp Pro
    210                 215                 220
```

```
Thr Val Asp Gln Val Asp Asp Thr Ser Ile Val Val Arg Trp Ser Arg
225                 230                 235                 240

Pro Gln Ala Pro Ile Thr Gly Tyr Arg Ile Val Tyr Ser Pro Ser Val
                245                 250                 255

Glu Gly Ser Ser Thr Glu Leu Asn Leu Pro Glu Thr Ala Asn Ser Val
            260                 265                 270

Thr Leu Ser Asp Leu Gln Pro Gly Val Gln Tyr Asn Ile Thr Ile Tyr
        275                 280                 285

Ala Val Glu Glu Asn Gln Glu Ser Thr Pro Val Val Ile Gln Gln Glu
    290                 295                 300

Thr Thr Gly Thr Pro Arg Ser Asp Gly Ser Ser Gly Ser Ser Gly Ser
305                 310                 315                 320

Ser Pro Thr Asp Leu Arg Phe Thr Asn Ile Gly Pro Asp Thr Met Arg
                325                 330                 335

Val Thr Trp Ala Pro Pro Ser Ile Asp Leu Thr Asn Phe Leu Val
                340                 345                 350

Arg Tyr Ser Pro Val Lys Asn Glu Glu Asp Val Ala Glu Leu Ser Ile
            355                 360                 365

Ser Pro Ser Asp Asn Ala Val Val Leu Thr Asn Leu Leu Pro Gly Thr
        370                 375                 380

Glu Tyr Val Val Ser Val Ser Ser Val Tyr Glu Gln His Glu Ser Thr
385                 390                 395                 400

Pro Leu Arg Gly Arg Gln Lys Thr Gly Leu Asp Ser Pro Thr Gly Ile
                405                 410                 415

Asp Phe Ser Asp Ile Thr Ala Asn Ser Phe Thr Val His Trp Ile Ala
                420                 425                 430

Pro Arg Ala Thr Ile Thr Gly Tyr Arg Ile Arg His His Pro Glu His
            435                 440                 445

Phe Ser Gly Arg Pro Arg Glu Asp Arg Val Pro His Ser Arg Asn Ser
    450                 455                 460

Ile Thr Leu Thr Asn Leu Thr Pro Gly Thr Glu Tyr Val Val Ser Ile
465                 470                 475                 480

Val Ala Leu Asn Gly Arg Glu Glu Ser Pro Leu Leu Ile Gly Gln Gln
                485                 490                 495

Ser Thr Val Ser Asp Val Pro Arg Asp Leu Glu Val Val Ala Ala Thr
            500                 505                 510

Pro Thr Ser Leu Leu Ile Ser Trp Asp Ala Pro Ala Val Thr Val Arg
        515                 520                 525

Tyr Tyr Arg Ile Thr Tyr Gly Glu Thr Gly Gly Asn Ser Pro Val Gln
    530                 535                 540

Glu Phe Thr Val Pro Gly Ser Lys Ser Thr Ala Thr Ile Ser Gly Leu
545                 550                 555                 560

Lys Pro Gly Val Asp Tyr Thr Ile Thr Val Tyr Ala Val Thr Gly Arg
                565                 570                 575

Gly Asp Ser Pro Ala Ser Ser Lys Pro Ile Ser Ile Asn Tyr Arg Thr
            580                 585                 590

Glu Ile Asp Lys Pro Ser Met Ala Ile Pro Ala Pro Thr Asp Leu Lys
        595                 600                 605

Phe Thr Gln Val Thr Pro Thr Ser Leu Ser Ala Gln Trp Thr Pro Pro
    610                 615                 620

Asn Val Gln Leu Thr Gly Tyr Arg Val Arg Val Thr Pro Lys Glu Lys
625                 630                 635                 640
```

Thr Gly Pro Met Lys Glu Ile Asn Leu Ala Pro Asp Ser Ser Val
            645                 650                 655

Val Val Ser Gly Leu Met Val Ala Thr Lys Tyr Glu Val Ser Val Tyr
        660                 665                 670

Ala Leu Lys Asp Thr Leu Thr Ser Arg Pro Ala Gln Gly Val Val Thr
        675                 680                 685

Thr Leu Glu Asn Val Ser Pro Pro Arg Arg Ala Arg Val Thr Asp Ala
        690                 695                 700

Thr Glu Thr Thr Ile Thr Ile Ser Trp Arg Thr Lys Thr Glu Thr Ile
705                 710                 715                 720

Thr Gly Phe Gln Val Asp Ala Val Pro Ala Asn Gly Gln Thr Pro Ile
                725                 730                 735

Gln Arg Thr Ile Lys Pro Asp Val Arg Ser Tyr Thr Ile Thr Gly Leu
            740                 745                 750

Gln Pro Gly Thr Asp Tyr Lys Ile Tyr Leu Tyr Thr Leu Asn Asp Asn
        755                 760                 765

Ala Arg Ser Ser Pro Val Val Ile Asp Ala Ser Thr Ala Ile Asp Ala
        770                 775                 780

Pro Ser Asn Leu Arg Phe Leu Ala Thr Pro Asn Ser Leu Leu Val
785                 790                 795                 800

Ser Trp Gln Pro Pro Arg Ala Arg Ile Thr Gly Tyr Ile Ile Lys Tyr
                805                 810                 815

Glu Lys Pro Gly Ser Pro Arg Glu Val Val Pro Arg Pro Arg Pro
            820                 825                 830

Gly Val Thr Glu Ala Thr Ile Thr Gly Leu Glu Pro Gly Thr Glu Tyr
        835                 840                 845

Thr Ile Tyr Val Ile Ala Leu Lys Asn Asn Gln Lys Ser Glu Pro Leu
850                 855                 860

Ile Gly Arg Lys Lys Thr Asp Glu Leu Pro Gln Leu Val Thr Leu Pro
865                 870                 875                 880

His Pro Asn Leu His Gly Pro Glu Ile Leu Asp Val Pro Ser Thr
                885                 890                 895

<210> SEQ ID NO 35
<211> LENGTH: 896
<212> TYPE: PRT
<213> ORGANISM: Artificial Sequence
<220> FEATURE:
<223> OTHER INFORMATION: N-terminal 15a.a. insertion of FCH-296

<400> SEQUENCE: 35

Met Ile Gly Glu Trp His Cys Gln Pro Leu Gln Thr Tyr Pro Ser Ser
1               5                   10                  15

Ser Gly Pro Val Glu Val Phe Ile Thr Glu Thr Pro Ser Gln Pro Asn
            20                  25                  30

Ser His Pro Ile Gln Trp Asn Ala Pro Gln Pro Ser His Ile Ser Lys
        35                  40                  45

Tyr Ile Leu Arg Trp Arg Pro Lys Asn Ser Val Gly Arg Trp Lys Glu
    50                  55                  60

Ala Thr Ile Pro Gly His Leu Asn Ser Tyr Thr Ile Lys Gly Leu Lys
65                  70                  75                  80

Pro Gly Val Val Tyr Glu Gly Gln Leu Ile Ser Ile Gln Tyr Gly
                85                  90                  95

His Gln Glu Val Thr Arg Phe Asp Phe Thr Thr Thr Ser Thr Ser Thr
                100                 105                 110

```
Pro Val Thr Ser Asn Thr Val Thr Gly Glu Thr Pro Phe Ser Pro
        115                 120                 125

Leu Val Ala Thr Ser Glu Ser Val Thr Glu Ile Thr Ala Ser Ser Phe
    130                 135                 140

Val Val Ser Trp Val Ser Ala Ser Asp Thr Val Ser Gly Phe Arg Val
145                 150                 155                 160

Glu Tyr Glu Leu Ser Glu Gly Asp Glu Pro Gln Tyr Leu Asp Leu
                165                 170                 175

Pro Ser Thr Ala Thr Ser Val Asn Ile Pro Asp Leu Leu Pro Gly Arg
                180                 185                 190

Lys Tyr Ile Val Asn Val Tyr Gln Ile Ser Glu Asp Gly Glu Gln Ser
            195                 200                 205

Leu Ile Leu Ser Thr Ser Gln Thr Thr Ala Pro Asp Ala Pro Pro Asp
        210                 215                 220

Pro Thr Val Asp Gln Val Asp Asp Thr Ser Ile Val Val Arg Trp Ser
225                 230                 235                 240

Arg Pro Gln Ala Pro Ile Thr Gly Tyr Arg Ile Val Tyr Ser Pro Ser
                245                 250                 255

Val Glu Gly Ser Ser Thr Glu Leu Asn Leu Pro Glu Thr Ala Asn Ser
                260                 265                 270

Val Thr Leu Ser Asp Leu Gln Pro Gly Val Gln Tyr Asn Ile Thr Ile
            275                 280                 285

Tyr Ala Val Glu Glu Asn Gln Glu Ser Thr Pro Val Val Ile Gln Gln
            290                 295                 300

Glu Thr Thr Gly Thr Pro Arg Ser Asp Gly Ser Ser Gly Ser Ser Gly
305                 310                 315                 320

Ser Ser Pro Thr Asp Leu Arg Phe Thr Asn Ile Gly Pro Asp Thr Met
                325                 330                 335

Arg Val Thr Trp Ala Pro Pro Ser Ile Asp Leu Thr Asn Phe Leu
                340                 345                 350

Val Arg Tyr Ser Pro Val Lys Asn Glu Glu Asp Val Ala Glu Leu Ser
            355                 360                 365

Ile Ser Pro Ser Asp Asn Ala Val Val Leu Thr Asn Leu Leu Pro Gly
        370                 375                 380

Thr Glu Tyr Val Val Ser Val Ser Ser Val Tyr Glu Gln His Glu Ser
385                 390                 395                 400

Thr Pro Leu Arg Gly Arg Gln Lys Thr Gly Leu Asp Ser Pro Thr Gly
                405                 410                 415

Ile Asp Phe Ser Asp Ile Thr Ala Asn Ser Phe Thr Val His Trp Ile
                420                 425                 430

Ala Pro Arg Ala Thr Ile Thr Gly Tyr Arg Ile Arg His His Pro Glu
            435                 440                 445

His Phe Ser Gly Arg Pro Arg Glu Asp Arg Val Pro His Ser Arg Asn
        450                 455                 460

Ser Ile Thr Leu Thr Asn Leu Thr Pro Gly Thr Glu Tyr Val Val Ser
465                 470                 475                 480

Ile Val Ala Leu Asn Gly Arg Glu Glu Ser Pro Leu Leu Ile Gly Gln
            485                 490                 495

Gln Ser Thr Val Ser Asp Val Pro Arg Asp Leu Glu Val Val Ala Ala
                500                 505                 510

Thr Pro Thr Ser Leu Leu Ile Ser Trp Asp Ala Pro Ala Val Thr Val
                515                 520                 525

Arg Tyr Tyr Arg Ile Thr Tyr Gly Glu Thr Gly Gly Asn Ser Pro Val
```

```
                                530             535             540
Gln Glu Phe Thr Val Pro Gly Ser Lys Ser Thr Ala Thr Ile Ser Gly
545                 550                 555                 560

Leu Lys Pro Gly Val Asp Tyr Thr Ile Thr Val Tyr Ala Val Thr Gly
                565                 570                 575

Arg Gly Asp Ser Pro Ala Ser Ser Lys Pro Ile Ser Ile Asn Tyr Arg
            580                 585                 590

Thr Glu Ile Asp Lys Pro Ser Met Ala Ile Pro Ala Pro Thr Asp Leu
        595                 600                 605

Lys Phe Thr Gln Val Thr Pro Thr Ser Leu Ser Ala Gln Trp Thr Pro
610                 615                 620

Pro Asn Val Gln Leu Thr Gly Tyr Arg Val Arg Val Thr Pro Lys Glu
625                 630                 635                 640

Lys Thr Gly Pro Met Lys Glu Ile Asn Leu Ala Pro Asp Ser Ser Ser
                645                 650                 655

Val Val Val Ser Gly Leu Met Val Ala Thr Lys Tyr Glu Val Ser Val
                660                 665                 670

Tyr Ala Leu Lys Asp Thr Leu Thr Ser Arg Pro Ala Gln Gly Val Val
                675                 680                 685

Thr Thr Leu Glu Asn Val Ser Pro Pro Arg Arg Ala Arg Val Thr Asp
        690                 695                 700

Ala Thr Glu Thr Thr Ile Thr Ile Ser Trp Arg Thr Lys Thr Glu Thr
705                 710                 715                 720

Ile Thr Gly Phe Gln Val Asp Ala Val Pro Ala Asn Gly Gln Thr Pro
                725                 730                 735

Ile Gln Arg Thr Ile Lys Pro Asp Val Arg Ser Tyr Thr Ile Thr Gly
            740                 745                 750

Leu Gln Pro Gly Thr Asp Tyr Lys Ile Tyr Leu Tyr Thr Leu Asn Asp
        755                 760                 765

Asn Ala Arg Ser Ser Pro Val Val Ile Asp Ala Ser Thr Ala Ile Asp
770                 775                 780

Ala Pro Ser Asn Leu Arg Phe Leu Ala Thr Thr Pro Asn Ser Leu Leu
785                 790                 795                 800

Val Ser Trp Gln Pro Pro Arg Ala Arg Ile Thr Gly Tyr Ile Ile Lys
                805                 810                 815

Tyr Glu Lys Pro Gly Ser Pro Arg Glu Val Val Pro Arg Pro Arg
                820                 825                 830

Pro Gly Val Thr Glu Ala Thr Ile Thr Gly Leu Glu Pro Gly Thr Glu
            835                 840                 845

Tyr Thr Ile Tyr Val Ile Ala Leu Lys Asn Asn Gln Lys Ser Glu Pro
        850                 855                 860

Leu Ile Gly Arg Lys Lys Thr Asp Glu Leu Pro Gln Leu Val Thr Leu
865                 870                 875                 880

Pro His Pro Asn Leu His Gly Pro Glu Ile Leu Asp Val Pro Ser Thr
                885                 890                 895

<210> SEQ ID NO 36
<211> LENGTH: 889
<212> TYPE: PRT
<213> ORGANISM: Artificial Sequence
<220> FEATURE:
<223> OTHER INFORMATION: N-terminal HKRHEEGH insertion of FCH-296

<400> SEQUENCE: 36

Met His Lys Arg His Glu Glu Gly His Ser Gly Pro Val Glu Val Phe
```

```
1               5                   10                  15
Ile Thr Glu Thr Pro Ser Gln Pro Asn Ser His Pro Ile Gln Trp Asn
                20                  25                  30
Ala Pro Gln Pro Ser His Ile Ser Lys Tyr Ile Leu Arg Trp Arg Pro
                35                  40                  45
Lys Asn Ser Val Gly Arg Trp Lys Glu Ala Thr Ile Pro Gly His Leu
 50                  55                  60
Asn Ser Tyr Thr Ile Lys Gly Leu Lys Pro Gly Val Val Tyr Glu Gly
 65                  70                  75                  80
Gln Leu Ile Ser Ile Gln Gln Tyr Gly His Gln Glu Val Thr Arg Phe
                85                  90                  95
Asp Phe Thr Thr Thr Ser Thr Ser Thr Pro Val Thr Ser Asn Thr Val
                100                 105                 110
Thr Gly Glu Thr Thr Pro Phe Ser Pro Leu Val Ala Thr Ser Glu Ser
                115                 120                 125
Val Thr Glu Ile Thr Ala Ser Ser Phe Val Val Ser Trp Val Ser Ala
                130                 135                 140
Ser Asp Thr Val Ser Gly Phe Arg Val Glu Tyr Glu Leu Ser Glu Glu
145                 150                 155                 160
Gly Asp Glu Pro Gln Tyr Leu Asp Leu Pro Ser Thr Ala Thr Ser Val
                165                 170                 175
Asn Ile Pro Asp Leu Leu Pro Gly Arg Lys Tyr Ile Val Asn Val Tyr
                180                 185                 190
Gln Ile Ser Glu Asp Gly Glu Gln Ser Leu Ile Leu Ser Thr Ser Gln
                195                 200                 205
Thr Thr Ala Pro Asp Ala Pro Pro Asp Pro Thr Val Asp Gln Val Asp
210                 215                 220
Asp Thr Ser Ile Val Val Arg Trp Ser Arg Pro Gln Ala Pro Ile Thr
225                 230                 235                 240
Gly Tyr Arg Ile Val Tyr Ser Pro Ser Val Glu Gly Ser Ser Thr Glu
                245                 250                 255
Leu Asn Leu Pro Glu Thr Ala Asn Ser Val Thr Leu Ser Asp Leu Gln
                260                 265                 270
Pro Gly Val Gln Tyr Asn Ile Thr Ile Tyr Ala Val Glu Glu Asn Gln
                275                 280                 285
Glu Ser Thr Pro Val Val Ile Gln Gln Glu Thr Thr Gly Thr Pro Arg
                290                 295                 300
Ser Asp Gly Ser Ser Gly Ser Ser Gly Ser Ser Pro Thr Asp Leu Arg
305                 310                 315                 320
Phe Thr Asn Ile Gly Pro Asp Thr Met Arg Val Thr Trp Ala Pro Pro
                325                 330                 335
Pro Ser Ile Asp Leu Thr Asn Phe Leu Val Arg Tyr Ser Pro Val Lys
                340                 345                 350
Asn Glu Glu Asp Val Ala Glu Leu Ser Ile Ser Pro Ser Asp Asn Ala
                355                 360                 365
Val Val Leu Thr Asn Leu Leu Pro Gly Thr Glu Tyr Val Val Ser Val
                370                 375                 380
Ser Ser Val Tyr Glu Gln His Glu Ser Thr Pro Leu Arg Gly Arg Gln
385                 390                 395                 400
Lys Thr Gly Leu Asp Ser Pro Thr Gly Ile Asp Phe Ser Asp Ile Thr
                405                 410                 415
Ala Asn Ser Phe Thr Val His Trp Ile Ala Pro Arg Ala Thr Ile Thr
                420                 425                 430
```

```
Gly Tyr Arg Ile Arg His His Pro Glu His Phe Ser Gly Arg Pro Arg
            435                 440                 445

Glu Asp Arg Val Pro His Ser Arg Asn Ser Ile Thr Leu Thr Asn Leu
        450                 455                 460

Thr Pro Gly Thr Glu Tyr Val Val Ser Ile Val Ala Leu Asn Gly Arg
465                 470                 475                 480

Glu Glu Ser Pro Leu Leu Ile Gly Gln Gln Ser Thr Val Ser Asp Val
                485                 490                 495

Pro Arg Asp Leu Glu Val Val Ala Ala Thr Pro Thr Ser Leu Leu Ile
            500                 505                 510

Ser Trp Asp Ala Pro Ala Val Thr Val Arg Tyr Tyr Arg Ile Thr Tyr
            515                 520                 525

Gly Glu Thr Gly Gly Asn Ser Pro Val Gln Glu Phe Thr Val Pro Gly
            530                 535                 540

Ser Lys Ser Thr Ala Thr Ile Ser Gly Leu Lys Pro Gly Val Asp Tyr
545                 550                 555                 560

Thr Ile Thr Val Tyr Ala Val Thr Gly Arg Gly Asp Ser Pro Ala Ser
                565                 570                 575

Ser Lys Pro Ile Ser Ile Asn Tyr Arg Thr Glu Ile Asp Lys Pro Ser
            580                 585                 590

Met Ala Ile Pro Ala Pro Thr Asp Leu Lys Phe Thr Gln Val Thr Pro
            595                 600                 605

Thr Ser Leu Ser Ala Gln Trp Thr Pro Pro Asn Val Gln Leu Thr Gly
            610                 615                 620

Tyr Arg Val Arg Val Thr Pro Lys Glu Lys Thr Gly Pro Met Lys Glu
625                 630                 635                 640

Ile Asn Leu Ala Pro Asp Ser Ser Ser Val Val Val Ser Gly Leu Met
                645                 650                 655

Val Ala Thr Lys Tyr Glu Val Ser Val Tyr Ala Leu Lys Asp Thr Leu
            660                 665                 670

Thr Ser Arg Pro Ala Gln Gly Val Val Thr Thr Leu Glu Asn Val Ser
            675                 680                 685

Pro Pro Arg Arg Ala Arg Val Thr Asp Ala Thr Glu Thr Thr Ile Thr
            690                 695                 700

Ile Ser Trp Arg Thr Lys Thr Glu Thr Ile Thr Gly Phe Gln Val Asp
705                 710                 715                 720

Ala Val Pro Ala Asn Gly Gln Thr Pro Ile Gln Arg Thr Ile Lys Pro
                725                 730                 735

Asp Val Arg Ser Tyr Thr Ile Thr Gly Leu Gln Pro Gly Thr Asp Tyr
            740                 745                 750

Lys Ile Tyr Leu Tyr Thr Leu Asn Asp Asn Ala Arg Ser Ser Pro Val
            755                 760                 765

Val Ile Asp Ala Ser Thr Ala Ile Asp Ala Pro Ser Asn Leu Arg Phe
            770                 775                 780

Leu Ala Thr Thr Pro Asn Ser Leu Leu Val Ser Trp Gln Pro Pro Arg
785                 790                 795                 800

Ala Arg Ile Thr Gly Tyr Ile Ile Lys Tyr Glu Lys Pro Gly Ser Pro
                805                 810                 815

Pro Arg Glu Val Val Pro Arg Pro Arg Pro Gly Val Thr Glu Ala Thr
            820                 825                 830

Ile Thr Gly Leu Glu Pro Gly Thr Glu Tyr Thr Ile Tyr Val Ile Ala
            835                 840                 845
```

```
Leu Lys Asn Asn Gln Lys Ser Glu Pro Leu Ile Gly Arg Lys Lys Thr
    850                 855                 860

Asp Glu Leu Pro Gln Leu Val Thr Leu Pro His Pro Asn Leu His Gly
865                 870                 875                 880

Pro Glu Ile Leu Asp Val Pro Ser Thr
                885
```

```
<210> SEQ ID NO 37
<211> LENGTH: 885
<212> TYPE: PRT
<213> ORGANISM: Artificial Sequence
<220> FEATURE:
<223> OTHER INFORMATION: N-terminal HKRH insertion of FCH-296

<400> SEQUENCE: 37

Met His Lys Arg His Ser Gly Pro Val Glu Val Phe Ile Thr Glu Thr
1               5                   10                  15

Pro Ser Gln Pro Asn Ser His Pro Ile Gln Trp Asn Ala Pro Gln Pro
            20                  25                  30

Ser His Ile Ser Lys Tyr Ile Leu Arg Trp Arg Pro Lys Asn Ser Val
        35                  40                  45

Gly Arg Trp Lys Glu Ala Thr Ile Pro Gly His Leu Asn Ser Tyr Thr
50                  55                  60

Ile Lys Gly Leu Lys Pro Gly Val Val Tyr Glu Gly Gln Leu Ile Ser
65                  70                  75                  80

Ile Gln Gln Tyr Gly His Gln Glu Val Thr Arg Phe Asp Phe Thr Thr
                85                  90                  95

Thr Ser Thr Ser Thr Pro Val Thr Ser Asn Thr Val Thr Gly Glu Thr
            100                 105                 110

Thr Pro Phe Ser Pro Leu Val Ala Thr Ser Glu Ser Val Thr Glu Ile
        115                 120                 125

Thr Ala Ser Ser Phe Val Val Ser Trp Val Ser Ala Ser Asp Thr Val
130                 135                 140

Ser Gly Phe Arg Val Glu Tyr Glu Leu Ser Glu Glu Gly Asp Glu Pro
145                 150                 155                 160

Gln Tyr Leu Asp Leu Pro Ser Thr Ala Thr Ser Val Asn Ile Pro Asp
                165                 170                 175

Leu Leu Pro Gly Arg Lys Tyr Ile Val Asn Val Tyr Gln Ile Ser Glu
            180                 185                 190

Asp Gly Glu Gln Ser Leu Ile Leu Ser Thr Ser Gln Thr Thr Ala Pro
        195                 200                 205

Asp Ala Pro Pro Asp Pro Thr Val Asp Gln Val Asp Asp Thr Ser Ile
    210                 215                 220

Val Val Arg Trp Ser Arg Pro Gln Ala Pro Ile Thr Gly Tyr Arg Ile
225                 230                 235                 240

Val Tyr Ser Pro Ser Val Glu Gly Ser Ser Thr Glu Leu Asn Leu Pro
                245                 250                 255

Glu Thr Ala Asn Ser Val Thr Leu Ser Asp Leu Gln Pro Gly Val Gln
            260                 265                 270

Tyr Asn Ile Thr Ile Tyr Ala Val Glu Glu Asn Gln Glu Ser Thr Pro
        275                 280                 285

Val Val Ile Gln Gln Glu Thr Thr Gly Thr Pro Arg Ser Asp Gly Ser
    290                 295                 300

Ser Gly Ser Ser Gly Ser Ser Pro Thr Asp Leu Arg Phe Thr Asn Ile
305                 310                 315                 320
```

```
Gly Pro Asp Thr Met Arg Val Thr Trp Ala Pro Pro Ser Ile Asp
                325                 330                 335

Leu Thr Asn Phe Leu Val Arg Tyr Ser Pro Val Lys Asn Glu Glu Asp
            340                 345                 350

Val Ala Glu Leu Ser Ile Ser Pro Ser Asp Asn Ala Val Val Leu Thr
            355                 360                 365

Asn Leu Leu Pro Gly Thr Glu Tyr Val Val Ser Val Ser Ser Val Tyr
        370                 375                 380

Glu Gln His Glu Ser Thr Pro Leu Arg Gly Arg Gln Lys Thr Gly Leu
385                 390                 395                 400

Asp Ser Pro Thr Gly Ile Asp Phe Ser Asp Ile Thr Ala Asn Ser Phe
                405                 410                 415

Thr Val His Trp Ile Ala Pro Arg Ala Thr Ile Thr Gly Tyr Arg Ile
            420                 425                 430

Arg His His Pro Glu His Phe Ser Gly Arg Pro Arg Glu Asp Arg Val
        435                 440                 445

Pro His Ser Arg Asn Ser Ile Thr Leu Thr Asn Leu Thr Pro Gly Thr
            450                 455                 460

Glu Tyr Val Val Ser Ile Val Ala Leu Asn Gly Arg Glu Glu Ser Pro
465                 470                 475                 480

Leu Leu Ile Gly Gln Gln Ser Thr Val Ser Asp Val Pro Arg Asp Leu
                485                 490                 495

Glu Val Val Ala Ala Thr Pro Thr Ser Leu Leu Ile Ser Trp Asp Ala
            500                 505                 510

Pro Ala Val Thr Val Arg Tyr Tyr Arg Ile Thr Tyr Gly Glu Thr Gly
        515                 520                 525

Gly Asn Ser Pro Val Gln Glu Phe Thr Val Pro Gly Ser Lys Ser Thr
530                 535                 540

Ala Thr Ile Ser Gly Leu Lys Pro Gly Val Asp Tyr Thr Ile Thr Val
545                 550                 555                 560

Tyr Ala Val Thr Gly Arg Gly Asp Ser Pro Ala Ser Ser Lys Pro Ile
                565                 570                 575

Ser Ile Asn Tyr Arg Thr Glu Ile Asp Lys Pro Ser Met Ala Ile Pro
            580                 585                 590

Ala Pro Thr Asp Leu Lys Phe Thr Gln Val Thr Pro Thr Ser Leu Ser
        595                 600                 605

Ala Gln Trp Thr Pro Pro Asn Val Gln Leu Thr Gly Tyr Arg Val Arg
            610                 615                 620

Val Thr Pro Lys Glu Lys Thr Gly Pro Met Lys Glu Ile Asn Leu Ala
625                 630                 635                 640

Pro Asp Ser Ser Ser Val Val Val Ser Gly Leu Met Val Ala Thr Lys
                645                 650                 655

Tyr Glu Val Ser Val Tyr Ala Leu Lys Asp Thr Leu Thr Ser Arg Pro
            660                 665                 670

Ala Gln Gly Val Val Thr Thr Leu Glu Asn Val Ser Pro Pro Arg Arg
        675                 680                 685

Ala Arg Val Thr Asp Ala Thr Glu Thr Thr Ile Thr Ile Ser Trp Arg
            690                 695                 700

Thr Lys Thr Glu Thr Ile Thr Gly Phe Gln Val Asp Ala Val Pro Ala
705                 710                 715                 720

Asn Gly Gln Thr Pro Ile Gln Arg Thr Ile Lys Pro Asp Val Arg Ser
                725                 730                 735

Tyr Thr Ile Thr Gly Leu Gln Pro Gly Thr Asp Tyr Lys Ile Tyr Leu
```

```
                    740                 745                 750
Tyr Thr Leu Asn Asp Asn Ala Arg Ser Ser Pro Val Val Ile Asp Ala
                755                 760                 765

Ser Thr Ala Ile Asp Ala Pro Ser Asn Leu Arg Phe Leu Ala Thr Thr
        770                 775                 780

Pro Asn Ser Leu Leu Val Ser Trp Gln Pro Pro Arg Ala Arg Ile Thr
785                 790                 795                 800

Gly Tyr Ile Ile Lys Tyr Glu Lys Pro Gly Ser Pro Pro Arg Glu Val
                805                 810                 815

Val Pro Arg Pro Arg Pro Gly Val Thr Glu Ala Thr Ile Thr Gly Leu
                820                 825                 830

Glu Pro Gly Thr Glu Tyr Thr Ile Tyr Val Ile Ala Leu Lys Asn Asn
                835                 840                 845

Gln Lys Ser Glu Pro Leu Ile Gly Arg Lys Lys Thr Asp Glu Leu Pro
                850                 855                 860

Gln Leu Val Thr Leu Pro His Pro Asn Leu His Gly Pro Glu Ile Leu
865                 870                 875                 880

Asp Val Pro Ser Thr
                885

<210> SEQ ID NO 38
<211> LENGTH: 883
<212> TYPE: PRT
<213> ORGANISM: Artificial Sequence
<220> FEATURE:
<223> OTHER INFORMATION: N-terminal HH insertion of FCH-296

<400> SEQUENCE: 38

Met His His Ser Gly Pro Val Glu Val Phe Ile Thr Glu Thr Pro Ser
1               5                   10                  15

Gln Pro Asn Ser His Pro Ile Gln Trp Asn Ala Pro Gln Pro Ser His
                20                  25                  30

Ile Ser Lys Tyr Ile Leu Arg Trp Arg Pro Lys Asn Ser Val Gly Arg
            35                  40                  45

Trp Lys Glu Ala Thr Ile Pro Gly His Leu Asn Ser Tyr Thr Ile Lys
        50                  55                  60

Gly Leu Lys Pro Gly Val Val Tyr Glu Gly Gln Leu Ile Ser Ile Gln
65              70                  75                  80

Gln Tyr Gly His Gln Glu Val Thr Arg Phe Asp Phe Thr Thr Thr Ser
                85                  90                  95

Thr Ser Thr Pro Val Thr Ser Asn Thr Val Thr Gly Glu Thr Thr Pro
                100                 105                 110

Phe Ser Pro Leu Val Ala Thr Ser Glu Ser Val Thr Glu Ile Thr Ala
            115                 120                 125

Ser Ser Phe Val Val Ser Trp Val Ser Ala Ser Asp Thr Val Ser Gly
        130                 135                 140

Phe Arg Val Glu Tyr Glu Leu Ser Glu Glu Gly Asp Glu Pro Gln Tyr
145                 150                 155                 160

Leu Asp Leu Pro Ser Thr Ala Thr Ser Val Asn Ile Pro Asp Leu Leu
                165                 170                 175

Pro Gly Arg Lys Tyr Ile Val Asn Val Tyr Gln Ile Ser Glu Asp Gly
                180                 185                 190

Glu Gln Ser Leu Ile Leu Ser Thr Ser Gln Thr Thr Ala Pro Asp Ala
            195                 200                 205

Pro Pro Asp Pro Thr Val Asp Gln Val Asp Asp Thr Ser Ile Val Val
```

-continued

```
                210                 215                 220
Arg Trp Ser Arg Pro Gln Ala Pro Ile Thr Gly Tyr Arg Ile Val Tyr
225                 230                 235                 240

Ser Pro Ser Val Glu Gly Ser Ser Thr Glu Leu Asn Leu Pro Glu Thr
                245                 250                 255

Ala Asn Ser Val Thr Leu Ser Asp Leu Gln Pro Gly Val Gln Tyr Asn
                260                 265                 270

Ile Thr Ile Tyr Ala Val Glu Glu Asn Gln Glu Ser Thr Pro Val Val
                275                 280                 285

Ile Gln Gln Glu Thr Thr Gly Thr Pro Arg Ser Asp Gly Ser Ser Gly
                290                 295                 300

Ser Ser Gly Ser Ser Pro Thr Asp Leu Arg Phe Thr Asn Ile Gly Pro
305                 310                 315                 320

Asp Thr Met Arg Val Thr Trp Ala Pro Pro Ser Ile Asp Leu Thr
                325                 330                 335

Asn Phe Leu Val Arg Tyr Ser Pro Val Lys Asn Glu Glu Asp Val Ala
                340                 345                 350

Glu Leu Ser Ile Ser Pro Ser Asp Asn Ala Val Val Leu Thr Asn Leu
                355                 360                 365

Leu Pro Gly Thr Glu Tyr Val Val Ser Val Ser Ser Val Tyr Glu Gln
                370                 375                 380

His Glu Ser Thr Pro Leu Arg Gly Arg Gln Lys Thr Gly Leu Asp Ser
385                 390                 395                 400

Pro Thr Gly Ile Asp Phe Ser Asp Ile Thr Ala Asn Ser Phe Thr Val
                405                 410                 415

His Trp Ile Ala Pro Arg Ala Thr Ile Thr Gly Tyr Arg Ile Arg His
                420                 425                 430

His Pro Glu His Phe Ser Gly Arg Pro Arg Glu Asp Arg Val Pro His
                435                 440                 445

Ser Arg Asn Ser Ile Thr Leu Thr Asn Leu Thr Pro Gly Thr Glu Tyr
                450                 455                 460

Val Val Ser Ile Val Ala Leu Asn Gly Arg Glu Glu Ser Pro Leu Leu
465                 470                 475                 480

Ile Gly Gln Gln Ser Thr Val Ser Asp Val Pro Arg Asp Leu Glu Val
                485                 490                 495

Val Ala Ala Thr Pro Thr Ser Leu Leu Ile Ser Trp Asp Ala Pro Ala
                500                 505                 510

Val Thr Val Arg Tyr Tyr Arg Ile Thr Tyr Gly Glu Thr Gly Gly Asn
                515                 520                 525

Ser Pro Val Gln Glu Phe Thr Val Pro Gly Ser Lys Ser Thr Ala Thr
                530                 535                 540

Ile Ser Gly Leu Lys Pro Gly Val Asp Tyr Thr Ile Thr Val Tyr Ala
545                 550                 555                 560

Val Thr Gly Arg Gly Asp Ser Pro Ala Ser Ser Lys Pro Ile Ser Ile
                565                 570                 575

Asn Tyr Arg Thr Glu Ile Asp Lys Pro Ser Met Ala Ile Pro Ala Pro
                580                 585                 590

Thr Asp Leu Lys Phe Thr Gln Val Thr Pro Thr Ser Leu Ser Ala Gln
                595                 600                 605

Trp Thr Pro Pro Asn Val Gln Leu Thr Gly Tyr Arg Val Arg Val Thr
                610                 615                 620

Pro Lys Glu Lys Thr Gly Pro Met Lys Glu Ile Asn Leu Ala Pro Asp
625                 630                 635                 640
```

```
Ser Ser Ser Val Val Ser Gly Leu Met Val Ala Thr Lys Tyr Glu
            645                 650                 655

Val Ser Val Tyr Ala Leu Lys Asp Thr Leu Thr Ser Arg Pro Ala Gln
            660                 665                 670

Gly Val Val Thr Thr Leu Glu Asn Val Ser Pro Pro Arg Arg Ala Arg
            675                 680                 685

Val Thr Asp Ala Thr Glu Thr Thr Ile Thr Ile Ser Trp Arg Thr Lys
690                 695                 700

Thr Glu Thr Ile Thr Gly Phe Gln Val Asp Ala Val Pro Ala Asn Gly
705                 710                 715                 720

Gln Thr Pro Ile Gln Arg Thr Ile Lys Pro Asp Val Arg Ser Tyr Thr
                725                 730                 735

Ile Thr Gly Leu Gln Pro Gly Thr Asp Tyr Lys Ile Tyr Leu Tyr Thr
                740                 745                 750

Leu Asn Asp Asn Ala Arg Ser Ser Pro Val Val Ile Asp Ala Ser Thr
                755                 760                 765

Ala Ile Asp Ala Pro Ser Asn Leu Arg Phe Leu Ala Thr Thr Pro Asn
                770                 775                 780

Ser Leu Leu Val Ser Trp Gln Pro Pro Arg Ala Arg Ile Thr Gly Tyr
785                 790                 795                 800

Ile Ile Lys Tyr Glu Lys Pro Gly Ser Pro Arg Glu Val Val Pro
                805                 810                 815

Arg Pro Arg Pro Gly Val Thr Glu Ala Thr Ile Thr Gly Leu Glu Pro
                820                 825                 830

Gly Thr Glu Tyr Thr Ile Tyr Val Ile Ala Leu Lys Asn Asn Gln Lys
                835                 840                 845

Ser Glu Pro Leu Ile Gly Arg Lys Lys Thr Asp Glu Leu Pro Gln Leu
                850                 855                 860

Val Thr Leu Pro His Pro Asn Leu His Gly Pro Glu Ile Leu Asp Val
865                 870                 875                 880

Pro Ser Thr

<210> SEQ ID NO 39
<211> LENGTH: 884
<212> TYPE: PRT
<213> ORGANISM: Artificial Sequence
<220> FEATURE:
<223> OTHER INFORMATION: N-terminal HHH insertion of FCH-296

<400> SEQUENCE: 39

Met His His His Ser Gly Pro Val Glu Val Phe Ile Thr Glu Thr Pro
1               5                   10                  15

Ser Gln Pro Asn Ser His Pro Ile Gln Trp Asn Ala Pro Gln Pro Ser
                20                  25                  30

His Ile Ser Lys Tyr Ile Leu Arg Trp Arg Pro Lys Asn Ser Val Gly
            35                  40                  45

Arg Trp Lys Glu Ala Thr Ile Pro Gly His Leu Asn Ser Tyr Thr Ile
        50                  55                  60

Lys Gly Leu Lys Pro Gly Val Val Tyr Glu Gly Gln Leu Ile Ser Ile
65                  70                  75                  80

Gln Gln Tyr Gly His Gln Glu Val Thr Arg Phe Asp Phe Thr Thr Thr
                85                  90                  95

Ser Thr Ser Thr Pro Val Thr Ser Asn Thr Val Thr Gly Glu Thr Thr
                100                 105                 110
```

-continued

```
Pro Phe Ser Pro Leu Val Ala Thr Ser Glu Ser Val Thr Glu Ile Thr
            115                 120                 125
Ala Ser Ser Phe Val Val Ser Trp Val Ser Ala Ser Asp Thr Val Ser
130                 135                 140
Gly Phe Arg Val Glu Tyr Glu Leu Ser Glu Glu Gly Asp Glu Pro Gln
145                 150                 155                 160
Tyr Leu Asp Leu Pro Ser Thr Ala Thr Ser Val Asn Ile Pro Asp Leu
                165                 170                 175
Leu Pro Gly Arg Lys Tyr Ile Val Asn Val Tyr Gln Ile Ser Glu Asp
            180                 185                 190
Gly Glu Gln Ser Leu Ile Leu Ser Thr Ser Gln Thr Thr Ala Pro Asp
            195                 200                 205
Ala Pro Pro Asp Pro Thr Val Asp Gln Val Asp Asp Thr Ser Ile Val
        210                 215                 220
Val Arg Trp Ser Arg Pro Gln Ala Pro Ile Thr Gly Tyr Arg Ile Val
225                 230                 235                 240
Tyr Ser Pro Ser Val Glu Gly Ser Ser Thr Glu Leu Asn Leu Pro Glu
                245                 250                 255
Thr Ala Asn Ser Val Thr Leu Ser Asp Leu Gln Pro Gly Val Gln Tyr
            260                 265                 270
Asn Ile Thr Ile Tyr Ala Val Glu Glu Asn Gln Glu Ser Thr Pro Val
            275                 280                 285
Val Ile Gln Gln Glu Thr Thr Gly Thr Pro Arg Ser Asp Gly Ser Ser
        290                 295                 300
Gly Ser Ser Gly Ser Ser Pro Thr Asp Leu Arg Phe Thr Asn Ile Gly
305                 310                 315                 320
Pro Asp Thr Met Arg Val Thr Trp Ala Pro Pro Ser Ile Asp Leu
                325                 330                 335
Thr Asn Phe Leu Val Arg Tyr Ser Pro Val Lys Asn Glu Glu Asp Val
            340                 345                 350
Ala Glu Leu Ser Ile Ser Pro Ser Asp Asn Ala Val Val Leu Thr Asn
            355                 360                 365
Leu Leu Pro Gly Thr Glu Tyr Val Val Ser Val Ser Ser Val Tyr Glu
        370                 375                 380
Gln His Glu Ser Thr Pro Leu Arg Gly Arg Gln Lys Thr Gly Leu Asp
385                 390                 395                 400
Ser Pro Thr Gly Ile Asp Phe Ser Asp Ile Thr Ala Asn Ser Phe Thr
                405                 410                 415
Val His Trp Ile Ala Pro Arg Ala Thr Ile Thr Gly Tyr Arg Ile Arg
            420                 425                 430
His His Pro Glu His Phe Ser Gly Arg Pro Arg Glu Asp Arg Val Pro
            435                 440                 445
His Ser Arg Asn Ser Ile Thr Leu Thr Asn Leu Thr Pro Gly Thr Glu
        450                 455                 460
Tyr Val Val Ser Ile Val Ala Leu Asn Gly Arg Glu Glu Ser Pro Leu
465                 470                 475                 480
Leu Ile Gly Gln Gln Ser Thr Val Ser Asp Val Pro Arg Asp Leu Glu
                485                 490                 495
Val Val Ala Ala Thr Pro Thr Ser Leu Leu Ile Ser Trp Asp Ala Pro
            500                 505                 510
Ala Val Thr Val Arg Tyr Tyr Arg Ile Thr Tyr Gly Glu Thr Gly Gly
            515                 520                 525
Asn Ser Pro Val Gln Glu Phe Thr Val Pro Gly Ser Lys Ser Thr Ala
```

```
                   530                535                540
Thr Ile Ser Gly Leu Lys Pro Gly Val Asp Tyr Thr Ile Thr Val Tyr
545                 550                 555                 560

Ala Val Thr Gly Arg Gly Asp Ser Pro Ala Ser Ser Lys Pro Ile Ser
                565                 570                 575

Ile Asn Tyr Arg Thr Glu Ile Asp Lys Pro Ser Met Ala Ile Pro Ala
                580                 585                 590

Pro Thr Asp Leu Lys Phe Thr Gln Val Thr Pro Thr Ser Leu Ser Ala
                595                 600                 605

Gln Trp Thr Pro Pro Asn Val Gln Leu Thr Gly Tyr Arg Val Arg Val
                610                 615                 620

Thr Pro Lys Glu Lys Thr Gly Pro Met Lys Glu Ile Asn Leu Ala Pro
625                 630                 635                 640

Asp Ser Ser Ser Val Val Val Ser Gly Leu Met Val Ala Thr Lys Tyr
                645                 650                 655

Glu Val Ser Val Tyr Ala Leu Lys Asp Thr Leu Thr Ser Arg Pro Ala
                660                 665                 670

Gln Gly Val Val Thr Thr Leu Glu Asn Val Ser Pro Pro Arg Arg Ala
                675                 680                 685

Arg Val Thr Asp Ala Thr Glu Thr Thr Ile Thr Ile Ser Trp Arg Thr
                690                 695                 700

Lys Thr Glu Thr Ile Thr Gly Phe Gln Val Asp Ala Val Pro Ala Asn
705                 710                 715                 720

Gly Gln Thr Pro Ile Gln Arg Thr Ile Lys Pro Asp Val Arg Ser Tyr
                725                 730                 735

Thr Ile Thr Gly Leu Gln Pro Gly Thr Asp Tyr Lys Ile Tyr Leu Tyr
                740                 745                 750

Thr Leu Asn Asp Asn Ala Arg Ser Ser Pro Val Val Ile Asp Ala Ser
                755                 760                 765

Thr Ala Ile Asp Ala Pro Ser Asn Leu Arg Phe Leu Ala Thr Thr Pro
                770                 775                 780

Asn Ser Leu Leu Val Ser Trp Gln Pro Pro Arg Ala Arg Ile Thr Gly
785                 790                 795                 800

Tyr Ile Ile Lys Tyr Glu Lys Pro Gly Ser Pro Pro Arg Glu Val Val
                805                 810                 815

Pro Arg Pro Arg Pro Gly Val Thr Glu Ala Thr Ile Thr Gly Leu Glu
                820                 825                 830

Pro Gly Thr Glu Tyr Thr Ile Tyr Val Ile Ala Leu Lys Asn Asn Gln
                835                 840                 845

Lys Ser Glu Pro Leu Ile Gly Arg Lys Lys Thr Asp Glu Leu Pro Gln
850                 855                 860

Leu Val Thr Leu Pro His Pro Asn Leu His Gly Pro Glu Ile Leu Asp
865                 870                 875                 880

Val Pro Ser Thr
```

LYMPHOCYTE PRODUCTION METHOD

TECHNICAL FIELD

The present invention relates to a method for producing a lymphocyte, which is useful in the medical field.

Living bodies are protected from foreign substances mainly by immune response. The immune system is composed of various cells and soluble factors produced by the cells. Among the cells, lymphocytes, which are one of the subtypes of white blood cells, play a particularly central role. Lymphocytes are mainly classified into three types: T cells (sometimes referred to as T lymphocytes), B cells (sometimes referred to as B lymphocytes), and natural killer cells (sometimes referred to as NK cells).

Further, T cells are subclassified into helper T cells, which express CD (Cluster Designation) 4 and are mainly involved in assisting antibody production and in inducing various immune responses; cytotoxic T cells (also referred to as cytotoxic T lymphocytes or killer T cells), which express CD8 and mainly exhibit cytotoxic activity; and other T cells.

For methods for producing lymphocytes, an extracellular matrix such as Matrigel, laminin, or fibronectin can be used as a substrate for culturing lymphocytes.

A study of a method for producing lymphocytes using a fibronectin fragment is disclosed in, for example, Patent Literature 1. The method disclosed in Patent Literature 1 comprises culturing a progenitor cell in the presence of a recombinant fibronectin fragment such as CH-296 to efficiently induce, maintain or expand a cytotoxic T cell. However, this method produces cytotoxic T cells, and cannot efficiently produce the other types of lymphocytes.

As described above, a technique for producing various types of lymphocytes using a fibronectin fragment has not been established yet.

CITATION LIST

Patent Literatures

Patent Literature 1: WO2005/019450

SUMMARY OF INVENTION

Problem to be Solved by the Invention

For solving the problems of the conventional methods for producing lymphocytes, an object of the present invention is to provide a method for producing various types of lymphocytes using a fibronectin fragment.

Solution for Problem

The present inventors conducted extensive studies to attain the above-mentioned object. As a result, the present inventors found that lymphocytes were efficiently proliferated by culturing the lymphocytes in the presence of a novel recombinant fibronectin fragment. Thus the present invention was completed.

Specifically, the present invention relates to:

[1] A method of producing a lymphocyte, the method comprising a step of culturing a lymphocyte in the presence of:
  (a) a recombinant polypeptide comprising human fibronectin III-1 to 3 repeats, or a recombinant polypeptide comprising an amino acid sequence which differs from the amino acid sequence of the III-1 to 3 repeats by substitution, deletion, insertion or addition of one or several amino acids;
  (b) a recombinant polypeptide comprising human fibronectin III-8 to 10 repeats, or a recombinant polypeptide comprising an amino acid sequence which differs from the amino acid sequence of the III-8 to 10 repeats by substitution, deletion, insertion or addition of one or several amino acids; and
  (c) a recombinant polypeptide comprising human fibronectin III-12 to 14 repeats, or a recombinant polypeptide comprising an amino acid sequence which differs from the amino acid sequence of the III-12 to 14 repeats by substitution, deletion, insertion or addition of one or several amino acids;

[2] The method according to [1], wherein the lymphocyte is cultured in the presence of a recombinant polypeptide containing the recombinant polypeptides (a), (b) and (c) within the same molecule;

[3] The method according to [2], wherein the recombinant polypeptide is a recombinant polypeptide comprising an amino acid sequence set forth in SEQ ID NO: 19, or a recombinant polypeptide comprising an amino acid sequence which differs from the amino acid sequence of SEQ ID NO: 19 by substitution, deletion, insertion or addition of 1 or several amino acids;

[4] The method according to [2], wherein the recombinant polypeptide is a recombinant polypeptide comprising an amino acid sequence set forth in SEQ ID NO: 31, or a recombinant polypeptide comprising an amino acid sequence which differs from the amino acid sequence of SEQ ID NO: 31 by substitution, deletion, insertion or addition of 1 or several amino acids;

[5] The method according to any one of [1] to [4], wherein the lymphocyte is cultured in the presence of the recombinant polypeptide and an anti-CD3 antibody;

[6] The method according to any one of [1] to [5], wherein the step of culturing a lymphocyte in the presence of the recombinant polypeptides is performed in a state where a solid phase coated with the recombinant polypeptides is in contact with the lymphocyte;

[7] The method according to [6], wherein the solid phase is a cell culture device or a cell culture carrier;

[8] The method according to [6], wherein the solid phase is a dish, plate, flask, bag, bead, membrane or glass slide; and

[9] The method according to any one of [1] to [8], wherein the lymphocyte is a human-derived lymphocyte.

Effects of the Invention

The present invention provides a method for producing a lymphocyte. According to the method of the present invention, lymphocytes can be efficiently proliferated, lymphocyte functions can be maintained, and lymphocytes can be efficiently induced. For example, the lymphocytes obtained by the present invention is suitable for use in regenerative medicine. Therefore, the method of the present invention is expected to make a great contribution to the medical field.

BRIEF DESCRIPTION OF DRAWINGS

FIG. 1 is a schematic diagram showing a domain structure of fibronectin.

FIG. 2 shows examples of naive cell rates in lymphocytes obtained by the method of the present invention. In the figure, "−" indicates a negative control which was cultured using a plate not coated with a recombinant polypeptide.

MODE FOR CARRYING OUT THE INVENTION

Hereinafter, the present invention will be explained in detail.
<Fibronectin>
Fibronectin derived from human and mammals has been well studied. The findings mainly on plasma fibronectin derived from human are described below.

Fibronectin is a huge glycoprotein having a molecular weight of about 250 kDa (monomer) present in the blood, cell surface, extracellular matrix and the like. Fibronectin is known to have various functions such as cell adhesion. Fibronectin is composed of a domain structure (see FIG. 1), and its amino acid sequence contains three kinds of similar sequences. The three kinds of similar sequences are called type I repeats, type II repeats, and type III repeats. Among these, a type III repeat is composed of 87 to 96 amino acid residues, and an amino acid sequence homology between the repeats is 17 to 40%. Fifteen type III repeats are present in fibronectin. Among them, the 1st, 2nd, and 3rd repeats (hereinafter referred to as III-1, III-2, and III-3, respectively) are contained in the self-association domain, the 4th, 5th, and 6th repeats (hereinafter referred to as III-4, III-5, and III-6, respectively) are contained in the DNA binding domain, the 8th, 9th, and 10th repeats (hereinafter referred to as III-8, III-9, and III-10, respectively) are contained in the cell binding domain, and the 12th, 13th and 14th repeats (hereinafter referred to as III-12, III-13, and III-14, respectively) are contained in the heparin-binding domain. III-10 contains a region having a binding activity to integrin α5β1 (also referred to as VLA-5), and the core sequence is RGD. In addition, there is a region called IIICS at a position close to the C-terminus of fibronectin. IIICS contains a sequence composed of 25 amino acids which is called CS-1, and the sequence shows a binding activity to integrin α4β1 (also referred to as VLA-4).

The amino acid sequences of human fibronectin III-1 to and CS-1 are shown as SEQ ID NOs: 1 to 14 and 15, respectively in the Sequence Listing of the present specification.

1. Method of Producing Lymphocyte of the Present Invention

The method of producing a lymphocyte of the present invention is characterized by comprising a step of culturing a lymphocyte in the presence of polypeptides which are recombinant fibronectin fragments.

Lymphocytes are classified into various types depending on differences in the expression and/or function of marker molecules. The three major types of lymphocytes are T cells, B cells and natural killer cells (NK cells).

Most mature T cells present in the periphery express either CD4 or CD8 as cell surface marker molecules. T cells expressing CD4 function as helper T cells which induce the functional expression of other T cells or induce differentiation and maturation, and antibody production of B cells. On the other hand, CD8-positive T cells function as cytotoxic T cells which destroy virus-infected cells and the like. In addition, there are NKT cells which have the properties of both NK cells and T cells, and regulatory T cells (also referred to as Treg) which express the CD25 molecule and suppress the activity of other T cells. In recent years, it has been known that there are peripheral T cells that differentiate and mature without going through the thymus gland.

In B cells, the type of antibody to be produced by each cell is fixed. Each B cell activates and initiates the antibody production only when a pathogen suitable for the antibody type of the B cell appears.

In addition, NK cells are a type of cytotoxic lymphocytes that act as a major factor of innate immunity, and are particularly important for the rejection of tumor cells and virus-infected cells.

The lymphocytes used in the present invention may be any lymphocytes as described above. In a preferred embodiment of the present invention, the lymphocytes are preferably T cells, more preferably CD4-expressing lymphocytes, and even more preferably helper T cells.

The method of the present invention is applicable not only to purified lymphocytes but also to a mixture of plural types of lymphocytes, a cell population containing lymphocytes and other cells, and the like. For example, as described in Examples below, lymphocytes can be produced by applying the method of the present invention to a population of mononuclear cells derived from peripheral blood.

The origin of the lymphocyte used in the present invention is not particularly limited, and a lymphocyte derived from any organism, preferably a mammal can be used. The age and sex of the organism are not particularly limited. In one embodiment, a cell derived from a primate (for example, chimpanzee, Japanese monkey, and human) is used. Most preferably, a cell derived from human is used, but the present invention is not limited thereto.

In the case of producing a lymphocyte by the method of the present invention for the purpose of administration to human, preferably, cells collected from a donor having a histocompatibility antigen type that is the same as or similar to the type of a recipient are subjected to the production of lymphocytes. For example, human peripheral blood mononuclear cells (PBMC) collected from the recipient himself/herself are subjected to the production of lymphocytes.

The method of producing a lymphocyte of the present invention is characterized by comprising a step of culturing a lymphocyte in the presence of recombinant polypeptides described below (hereinafter sometimes referred to as the culturing step of the present invention).

In the method of producing a lymphocyte of the present invention, a lymphocyte is cultured in the presence of the polypeptide (a), the polypeptide (b), and the polypeptide (c). In the method of producing a lymphocyte of the present invention, the culturing of a lymphocyte may be carried out in the presence of a mixture of two kinds of polypeptides that are a polypeptide comprising the polypeptide (a) and the polypeptide (b) in the same molecule and the polypeptide (c), in the presence of a mixture of two kinds of polypeptides that are a polypeptide comprising the polypeptide (b) and the polypeptide (c) in the same molecule and the polypeptide (a), in the presence of a mixture of two kinds of polypeptides that are a polypeptide comprising the polypeptide (a) and the polypeptide (c) in the same molecule and the polypeptide (b), in the presence of a mixture of two kinds of polypeptides that are a polypeptide comprising the polypeptide (a) and the polypeptide (b) in the same molecule and a polypeptide comprising the polypeptide (b) and the polypeptide (c) in the same molecule, or in the presence of one kind of polypeptide comprising the polypeptide (a), the polypeptide (b) and the polypeptide (c) in the same molecule. However, the above-described one kind of polypeptide comprising the polypeptide (a), the polypeptide (b) and the polypeptide (c) in the same molecule is different from full-length fibronectin.

The polypeptide (a) is a recombinant polypeptide comprising human fibronectin III-1 to 3 repeats, or a recombinant polypeptide comprising an amino acid sequence which differs from the amino acid sequence of the III-1 to 3 repeats by substitution, deletion, insertion or addition of one or several amino acids. That is, the polypeptide (a) is a polypeptide comprising all of III-1, III-2 and III-3 repeats.

The polypeptide (b) is a recombinant polypeptide comprising human fibronectin III-8 to 10 repeats, or a recombinant polypeptide comprising an amino acid sequence which differs from the amino acid sequence of the III-8 to 10 repeats by substitution, deletion, insertion or addition of one or several amino acids. That is, the polypeptide (b) is a polypeptide comprising all of III-8, III-9 and III-10.

The polypeptide (c) is a recombinant polypeptide comprising human fibronectin III-12 to 14 repeats, or a recombinant polypeptide comprising an amino acid sequence which differs from the amino acid sequence of the III-12 to 14 repeats by substitution, deletion, insertion or addition of one or several amino acids. That is, the polypeptide (c) is a polypeptide comprising all of III-12, III-13, and III-14.

Examples of the polypeptide comprising the polypeptide (a) and the polypeptide (b) in the same molecule include a 120 kDa fibronectin fragment (120k-fr). 120k-fr is a polypeptide having a molecular weight of about 120 kDa which comprises III-1, III-2, III-3, III-4, III-5, III-6, III-7, III-8, III-9 and III-10 from the N-terminal side in order. A predicted amino acid sequence (932 amino acid residues) of 120k-fr is shown as SEQ ID NO: 16 in the Sequence Listing of the present specification. 120k-fr can be produced as a recombinant polypeptide by preparing a DNA encoding the amino acid sequence of 120k-fr and combining it with an appropriate host-vector system. Commercially available 120k-fr may also be used.

Examples of the polypeptide comprising the polypeptide (b) and the polypeptide (c) in the same molecule include CH-271 and CH-296.

CH-271 is a recombinant polypeptide having a molecular weight of about 60 kDa (549 amino acid residues) which comprises III-8, III-9, III-10, III-12, III-13, and III-14 from the N-terminal side in order. The amino acid sequence of CH-271 is shown as SEQ ID NO: 17 in the Sequence Listing of the present specification.

CH-296 is a recombinant polypeptide having a molecular weight of about 63 kDa (574 amino acid residues) which comprises III-8, III-9, III-10, III-12, III-13, III-14, and CS-1 from the N-terminal side in order. The amino acid sequence of CH-296 is shown as SEQ ID NO: 18 in the Sequence Listing of the present specification. CH-296 is commercially available as RetroNectin (registered trademark, manufactured by TAKARA BIO INC.).

For example, the method of producing a lymphocyte of the present invention can be carried out by using 120k-fr in combination with CH-271 or CH-296.

A polypeptide comprising the polypeptide (a), the polypeptide (b) and the polypeptide (c) in the same molecule can be also used for the method of producing a lymphocyte of the present invention. Examples of the polypeptide comprising the polypeptide (a), the polypeptide (b) and the polypeptide (c) in the same molecule include, but not limited to, FCH-296 as described below.

FCH-296 is a recombinant polypeptide having a molecular weight of about 96 kDa (881 amino acid residues) which comprises III-1, III-2, III-3, III-8, III-9, III-10, III-12, III-13, III-14, and CS-1 from the N-terminal side in order. The amino acid sequence of FCH-296 is shown as SEQ ID NO: 19 in the Sequence Listing of the present specification. Amino acids 1 to 298 of SEQ ID NO: 19 correspond to the polypeptide (a), amino acids 299 to 307 of SEQ ID NO: 19 correspond to GS linker, amino acids 308 to 585 of SEQ ID NO: 19 correspond to the polypeptide (b), and amino acids 586 to 856 of SEQ ID NO: 19 correspond to the polypeptide (c), and amino acids 857 to 881 of SEQ ID NO: 19 correspond to CS-1. Meanwhile, amino acids 94 to 111 of SEQ ID NO: 19 form a region other than type III repeats which exists between III-1 and III-2.

Each of the polypeptides (a) to (c) used in the present invention may comprise an amino acid sequence differing from the amino acid sequence of III-1 to 3 repeats, the amino acid sequence of III-8 to 10 repeats or the amino acid sequence of III-12 to 14 repeats by substitution, deletion, insertion or addition of one or several amino acids, as long as the polypeptide is functionally equivalent or retains a function of making lymphocytes proliferate, a function of maintaining the function of lymphocytes, or a function of inducing lymphocytes. As used herein, "one or several" is, but not particularly limited, in the range of 1 to 15, preferably in the range of 1 to 10, more preferably in the range of 1 to 5, and particularly preferably in the range of 1 to 3. For example, the polypeptide includes, but not particularly limited to, a polypeptide comprising, instead of III-1 (SEQ ID NO: 1), an amino acid sequence having deletion of N-terminal 9 amino acids of III-1 (SEQ ID NO: 21), an amino acid sequence having deletion of N-terminal 6 amino acids of III-1 (SEQ ID NO: 22), an amino acid sequence having deletion of N-terminal 5 amino acids of III-1 (SEQ ID NO: 23), or an amino acid sequence having deletion of N-terminal 3 amino acids of III-1 (SEQ ID NO: 24). Further, examples of the polypeptide comprising the polypeptides (a) to (c) include a polypeptide comprising an amino acid sequence differing from the amino acid sequence of FCH-296 (SEQ ID NO: 19) by substitution, deletion, insertion or addition of one or several amino acids. More specific examples thereof include, but not limited to, FCH-296 having deletion of N-terminal 9 amino acids (SEQ ID NO: 25), FCH-296 having deletion of N-terminal 6 amino acids (SEQ ID NO: 26), FCH-296 having deletion of N-terminal 5 amino acids (SEQ ID NO: 27), FCH-296 having deletion of N-terminal 3 amino acids (SEQ ID NO: 28), FCH-296 having insertion of N-terminal 3 amino acids (SEQ ID NO: 29), FCH-296 having insertion of N-terminal 6 amino acids (SEQ ID NO: 30), FCH-296 having insertion of N-terminal 9 amino acids (SEQ ID NO: 31), FCH-296 having insertion of N-terminal 11 amino acids (SEQ ID NO: 32), FCH-296 having insertion of N-terminal 12 amino acids (SEQ ID NO: 33), FCH-296 having insertion of N-terminal 14 amino acids (SEQ ID NO: 34), FCH-296 having insertion of N-terminal 15 amino acids (SEQ ID NO: 35), FCH-296 having insertion of N-terminal HKRHEEGH (SEQ ID NO: 36), FCH-296 having insertion of N-terminal HKRH (SEQ ID NO: 37), FCH-296 having insertion of N-terminal HH (SEQ ID NO: 38), FCH-296 having insertion of N-terminal HHH (SEQ ID NO: 39), and FCH-296 having N-terminal His-tag (SEQ ID NO: 20). As used herein, the expression "FCH-296 having insertion of N-terminal (number) amino acids" means a polypeptide transcribed and translated from a nucleic acid encoding the amino acid sequence of FCH-296 into which a nucleic acid consisting of a nucleotide sequence encoding the number of amino acids is inserted immediately after the start codon. The FCH-296 having insertion of N-terminal amino acids also includes a polypeptide from which methionine encoded by the start codon is removed by post-translational modification. For example, "FCH-296 having insertion of N-terminal 3 amino acids" includes a polypeptide transcribed and translated from a nucleic acid encoding the amino acid sequence of FCH-296 into which a nucleic acid consisting of a nucleotide sequence encoding three amino acids is inserted immediately after the start codon, and the polypeptide from which methionine encoded by the start codon is removed by post-translational modification. Similarly, as used herein, the expression "FCH-296 having deletion of N-terminal (number) amino acids" means a polypeptide transcribed and translated from a nucleic acid encoding the amino acid sequence of FCH-296 from which a nucleic acid consisting of a nucleotide sequence encoding the number of amino acids immediately following the start codon is deleted. The FCH-296 having deletion of N-terminal amino acids also includes a polypeptide from which methionine encoded by the start codon is removed by post-translational modification. For example, "FCH-296 having deletion of N-terminal 3 amino acids" includes a polypeptide transcribed and translated from a nucleic acid encoding the amino acid sequence of FCH-296 from which a nucleic acid consisting of a nucleotide sequence encoding three amino acids immediately following the start codon is deleted, and the polypeptide from which methionine encoded by the start codon is removed by post-translational modification. Similarly, as used herein, "FCH-296 having N-terminal His-tag" includes a polypeptide transcribed and translated from a nucleic acid encoding the amino acid sequence of FCH-296 into which a nucleic acid consisting of a nucleotide sequence encoding a His-tag is inserted immediately after the start codon, and the polypeptide from which methionine encoded by the start codon is removed by post-translational modification.

Each of the polypeptides (a) to (c) used in the present invention may comprise an amino acid sequence having an identity with the amino acid sequence of III-1 to 3 repeats, the amino acid sequence of III-8 to 10 repeats or the amino acid sequence of III-12 to 14 repeats, as long as the polypeptide is functionally equivalent or retains a function of making lymphocytes proliferate, a function of maintaining the function of lymphocytes or a function of inducing lymphocytes. Examples thereof include, but not particularly limited to, a polypeptide having an amino acid sequence having 80% or more, preferably 90% or more, and particularly preferably 95% or more identity with the amino acid sequence of III-1 to 3 repeats, the amino acid sequence of III-8 to 10 repeats or the amino acid sequence of III-12 to 14 repeats.

The substitution, deletion, insertion or addition of amino acid(s) (hereinafter sometimes referred to as "amino acid substitution or the like") may be preferably carried out to the extent that the physicochemical properties or the like of the polypeptide can be changed within a range that can maintain the function of the original polypeptide. For example, the amino acid substitution or the like is preferably conservative in a range that does not substantially change the properties (for example, hydrophobicity, hydrophilicity, charge, pK, and the like) of the original polypeptide. For example, the amino acid substitution is substitution within each group of: 1. glycine, and alanine; 2. valine, isoleucine, and leucine; 3. aspartic acid, glutamic acid, asparagine, and glutamine; 4. serine, and threonine; 5. lysine, and arginine; and 6. phenylalanine, and tyrosine. The amino acid deletion, addition, or insertion is preferably deletion, addition, or insertion of amino acid(s) having similar properties to the properties around a target site in the polypeptide, within a range that does not substantially change the properties around the target site.

The amino acid substitution or the like may be naturally occurring due to species difference or individual difference, or may be artificially introduced. The artificial introduction may be carried out by a known method, which is not particularly limited. For example, substitution, deletion, addition or insertion of nucleotide(s) may be introduced into a nucleic acid encoding the polypeptide by a known method, and the nucleic acid thus obtained may be used to produce a polypeptide comprising an amino acid sequence having substitution or the like of one or several amino acids in the amino acid sequence of the polypeptide.

As used herein, the term "functionally equivalent" or "an equivalent function" means being functionally equivalent or an equivalent function to the corresponding polypeptide into which amino acid substitution or the like has not been introduced. That is, it means that when production of lymphocytes described later is carried out using the polypeptide to be compared, the same cell proliferation rate of lymphocytes as when the corresponding polypeptide into which amino acid substitution or the like has not been introduced is used is obtained, or the same function of lymphocytes as when the corresponding polypeptide into which amino acid substitution or the like has not been introduced is used is maintained, or the same induction rate of lymphocytes as when the corresponding polypeptide into which amino acid substitution or the like has not been introduced is used is obtained. That is, the function of the polypeptide can be appropriately confirmed by evaluating its properties according to the method described in Examples described later.

The polypeptide used in the present invention may contain peptide(s) or amino acid residue(s) other than the above-described type III repeats and/or region(s) present in fibronectin other than the above-described type III repeats such as CS-1, as long as the polypeptide does not lose its utility in culturing lymphocytes. For example, any peptide(s) or amino acid residue(s) can be introduced into region(s) other than the above-described type III repeats. Examples of such a polypeptide used in the present invention include a polypeptide containing amino acid residue(s) or peptide(s) as linker(s) inserted between the repeats, and a polypeptide to which a peptide (tag) useful for purification of a recombinant polypeptide is added. Examples of the linker include, but not limited to, a glycine-serine linker (GS linker). Examples of the tag include, but not limited to, a polyhistidine-tag (His-tag), a Flag-tag, and a Glutathione S-Transferase tag (GST-tag). Examples of the polypeptide used in the present invention include, but not limited to, a FCH-296 polypeptide having a His-tag at the N-terminus (SEQ ID NO: 20).

In the culturing step of the present invention, lymphocytes are cultured at a high cell proliferation rate. The method of producing a lymphocyte of the present invention is very useful because it has a higher cell proliferation rate as compared with a method using CH-296 which is a known fibronectin fragment.

For preparation of polypeptides, information on fibronectin can be seen in Kimiduka F., et al., J. Biochem., Vol. 110, pages 284-291 (1991), Kornbrihtt A. R., et al., EMBO J., Vol. 4, No. 7, 1755-1759 (1985), Sekiguchi K., et al., Biochemistry, Vol. 25, No. 17, 4936-4941 (1986) and the like. In addition, the nucleotide sequence encoding fibronectin and the amino acid sequence of fibronectin are disclosed in Genbank Accession Nos. NM_002026 and NP_002017.

The polypeptide used in the present invention is produced by recombinant DNA technology. From the viewpoint of production or handling of a recombinant, the molecular weight of the polypeptide used in the present invention is preferably 150 kDa or less, 140 kDa or less, 130 kDa or less, 120 kDa or less, 110 kDa or less, or 100 kDa or less. The polypeptide as used herein may be chemically modified, for example acetylated.

In a suitable aspect of the present invention, the culturing of a lymphocyte is carried out in a state where a solid phase coated with the polypeptides is in contact with the lymphocyte. Examples of the solid phase include a vessel or a carrier (a microbead and the like) used for cell culture. The solid phase coated with the polypeptides has the ability to retain lymphocytes stably and is useful for culturing the cells. The culture vessel may be of made of any material as long as it does not inhibit cell maintenance, survival, differentiation, maturation and self-renewal, and may have any shape as long as it does not inhibit cell maintenance, survival, differentiation, maturation and self-replication. Examples of the material for the culture vessel include glass, a synthetic resin including a nonwoven fabric, a natural resin, a metal and the like. Examples of the shape of the culture vessel include a polygonal column such as a triangular prism, a cube, and a rectangular parallelepiped, a cylinder, a polygonal pyramid such as a triangular pyramid, and a quadrangular pyramid, a cone, an any shape such as a gourd, a spherical shape, a hemispherical shape, a circular shape, an elliptical shape, a semicircular shape and the like.

Examples of a device for cell culture which is used for culturing lymphocytes include, but not limited to, a dish, a plate, a flask, a bag, a membrane, a glass slide, a large culture tank, a bioreactor, a hollow fiber type culture device and the like. Preferably, a plate is used, and more preferably a cell culture plate is used.

Examples of the bag include a $CO_2$ gas permeable bag for cell culture. When a large amount of lymphocytes is produced industrially, a large culture tank can be used. Culturing can be carried out in either an open system or a closed system. Preferably culturing is carried out in a closed system from the viewpoint of the safety of the obtained lymphocytes.

Coating of the solid phase, that is, immobilization of the polypeptides on the solid-phase surface may be carried out by a known method. For example, the coating can be carried out by the same method as the immobilization of fibronectin fragments described in WO 97/18318 and WO 00/09168. In the case where the polypeptides are immobilized on a solid phase, after obtaining lymphocytes by the method of the present invention, it is easy to separate the cells and the polypeptides of the present invention merely by separating the cells and the solid phase. Accordingly, contamination of the lymphocytes with the polypeptides and the like can be prevented.

More specifically, a coating solution is prepared by dissolving the polypeptides in sterilized distilled water, a buffer, a physiological saline or the like, and the coating solution can be used for immobilization. Preferably, the coating solution obtained using a phosphate buffered saline (PBS), particularly preferably Dulbecco's PBS (D-PBS) as a solvent may be used.

The molar concentration of the polypeptide in the coating solution is not particularly limited, but examples thereof include 1 to 10,000 nM, preferably 10 to 2000 nM, and more preferably 30 to 1000 nM. When FCH-296 is used as the polypeptide, the above-described molar concentration is expressed as weight concentration of 0.1 to 1000 μg/mL, preferably 1 to 200 μg/mL, and more preferably 3 to 100 μg/mL.

In a suitable embodiment of the present invention, the coating solution further contains an anti-CD3 antibody. The concentration of an anti-CD3 antibody contained in the coating solution used in the embodiment is, for example, a final concentration of 0.5 to 100 μg/mL, preferably 1 to 20 μg/mL, or more preferably 2 to 10 μg/mL. The coating solution may further contain other components and the like as long as the effects of the present invention are not impaired.

Coating can be carried out by adding the coating solution to the culture vessel and keeping it for an appropriate period of time. Conditions for keeping the coating solution may be appropriately determined, but examples of the conditions include a condition at room temperature for 1 hour, and a condition at 4° C. overnight.

The vessel coated with the fibronectin fragment can be used as it is or can be stored at a low temperature, for example at a temperature of 0 to 10° C. until use. Immediately before use, the coating solution is removed from the culture vessel, and the culture vessel is washed twice with, for example, D-PBS and then once with a cell culture medium if necessary, and then the culture vessel is subjected to cell culture.

The method of producing a lymphocyte of the present invention is performed by carrying out the culturing step in the presence of the polypeptides in the whole period or in any part of the period of culturing for the lymphocyte production. That is, the present invention includes any method comprising the culturing step of the present invention as a part of lymphocyte production process. For example, a method comprising using a cell population that does not contain lymphocytes to start the lymphocyte production process, inducing lymphocytes after the start of lymphocyte production process and culturing the lymphocytes in the presence of the polypeptides is included in the present invention.

The culturing step of the present invention includes induction of lymphocytes, maintenance of lymphocytes and/or expansion culture of lymphocytes. Accordingly, the present invention provides, for example, a method of producing a lymphocyte comprising inducing, maintaining, and expansion culturing a lymphocyte in the presence of the above-described recombinant polypeptides (a), (b) and (c); a method of producing a lymphocyte comprising inducing and maintaining a lymphocyte in the presence of the above-described recombinant polypeptides (a), (b) and (c); a method of producing a lymphocyte comprising maintaining and expansion culturing a lymphocyte in the presence of the above-described recombinant polypeptides (a), (b) and (c); a method of producing a lymphocyte comprising inducing a lymphocyte in the presence of the above-described recombinant polypeptides (a), (b) and (c); a method of producing a lymphocyte comprising maintaining a lymphocyte in the presence of the above-described recombinant polypeptides. (a), (b) and (c); and a method of producing a lymphocyte comprising expansion culturing a lymphocyte in the presence of the above-described recombinant polypeptides (a), (b) and (c). In the method of producing a lymphocyte of the present invention, a lymphocyte useful for regenerative medicine or the like can be produced by appropriately adjusting the type of a lymphocyte to be subjected to the method, culture conditions and the like to culture the lymphocyte. As used herein, a lymphocyte means a cell population containing lymphocytes.

For the purpose of induction of lymphocytes, in the culturing step of the present invention, the type of a cell to be used at the start of the culturing and a method for inducing lymphocytes are not particularly limited. The cell at the start of the culturing may be a pluripotent stem cell such as iPS cell or ES cell, a further differentiated cell such as hematopoietic stem cell, a precursor cell of lymphocyte, or a naive cell. The method for inducing lymphocytes may be a known method, which is not particularly limited.

For the purpose of maintaining and expansion culturing lymphocytes, the cell concentration at the start of the culture in the culturing step of the present invention is not particularly limited, but it is, for example, 0.005 to $20 \times 10^5$ cells/mL, preferably 0.02 to $5 \times 10^5$ cells/mL, or more preferably 0.05 to $2 \times 10^5$ cells/mL.

Various media used for culturing lymphocytes can be used in the culturing step of the present invention. Preferable examples include a medium not containing a xenogeneic component such as a fetal bovine serum (FBS) or a fetal calf serum (FCS) or a sheep serum, a serum-free medium, a medium not containing an unknown component (a defined medium) and the like. Such a xeno-free medium which is free from xenogeneic components can be appropriately prepared, but a known medium or a commercially available medium may be used as it is or modified. For example, GT-T551 medium (manufactured by TAKARA BIO INC.) may be used as a commercially available xeno-free medium.

In a suitable embodiment of the present invention, the medium further contains interleukin-2 (IL-2). The concentration of IL-2 used in this embodiment is, for example, a final concentration of 10 to 1000 IU/mL, preferably 50 to 500 IU/mL, or more preferably 100 to 300 IU/mL. The medium may further contain other components as long as the effects of the present invention are not impaired.

Culture conditions for cells are not particularly limited, and ordinary cell culture conditions can be employed. Examples of the culture conditions include, but not limited to, a culture condition at a temperature of 37° C., a humidity of 95% and a $CO_2$ concentration of 5%. Examples thereof include a culture condition at a temperature of 30 to 40° C., a humidity of 90 to 98%, and a $CO_2$ concentration of 3 to 7%. However, a temperature, a humidity and a $CO_2$ concentration outside the above-described ranges may be employed as long as desired lymphocyte proliferation can be achieved. During the culturing, it is preferable to dilute a cell culture medium with a fresh medium, replace the medium with a fresh medium, or, if needed, replace a culture vessel with a fresh one at appropriate time intervals. The medium to be used, and other components and the like to be used at the same time can be appropriately determined.

In a suitable aspect of the present invention, for the purpose of maintaining and expansion culturing lymphocytes, the lymphocytes are cultured in an appropriate medium in a vessel coated with the polypeptides used in the present invention. For example, they are cultured for 5 days or more, preferably for 10 days or more while medium replacement and passage are performed. By this culturing, lymphocytes can be proliferated.

The lymphocytes obtained by the production method of the present invention can be classified based on expression of marker molecules. The expression of marker molecules can be determined, for example, by using antibodies that recognize the marker molecules.

Examples of the marker molecules for lymphocytes include, but not limited to, CD3, CD4, and CD8. CD3 is a glycoprotein expressed on mature T lymphocytes and is one of cell surface antigens. CD4 is expressed on helper T cells, monocytes, macrophages, dendritic cells and the like. Generally, CD3-positive and CD4-positive cells (CD3+CD4+) are helper T cells. On the other hand, CD8 is expressed on cytotoxic T cells and some NK cells. Generally, CD3-positive and CD8-positive cells (CD3+CD8+) are cytotoxic T cells.

The lymphocytes obtained by the production method of the present invention highly express CD4. For example, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more of the lymphocytes obtained by the production method of the present invention express CD4. As compared to culturing in the absence of polypeptides (a) to (c) (negative control), the lymphocytes obtained by the production method of the present invention have a high proportion of CD4-expressing cells. The proportion of CD4-expressing cells in the lymphocytes obtained by the production method of the present invention is, for example, 1.3 or more times, 1.5 or more times, 1.7 or more times, 2 or more times, 2.3 or more times, 2.5 or more times, 2.7 or more times, or 3 or more times higher than the CD4-expressing cell proportion in the case of culturing in the absence of polypeptides (a) to (c) (negative control).

Other examples of the marker molecules for lymphocytes include CD45RA and CCR7. Generally, a CD45RA-positive and CCR7-positive (CD45RA+ CCR7+) phenotype is known as the phenotype of naive cells, a CD45RA-negative and CCR7-positive (CD45RA− CCR7+) phenotype is known as the phenotype of central memory cells, and a CD45RA-negative and CCR7-negative (CD45RA− CCR7−) phenotype is known as the phenotype of effector memory cells.

The lymphocytes obtained by the production method of the present invention have a high proportion of CD45RA-positive and CCR7-positive (CD45RA+ CCR7+) cells, that is, naive cells. For example, 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more of the lymphocytes obtained by the production method of the present invention express CD45RA and CCR7. As compared to culturing in the absence of polypeptides (a) to (c) (negative control), the lymphocytes obtained by the production method of the present invention have a high proportion of cells expressing CD45RA and CCR7. The proportion of cells expressing CD45RA and CCR7 in the lymphocytes obtained by the production method of the present invention is, for example, 1.3 or more times, 1.5 or more times, 1.7 or more times, 2 or more times, 2.3 or more times, 2.5 or more times, 2.7 or more times, or 3 or more times higher than the CD45RA- and CCR7-expressing cell proportion in the case of culturing in the absence of polypeptides (a) to (c) (negative control).

Further, a desired lymphocyte can be isolated from a cell population obtained by the production method of the present invention, and thereby a lymphocyte separated from other cells can be obtained. An antibody that recognizes a molecule characteristic of the desired lymphocyte is useful for isolating and purifying the lymphocyte obtained according to the present invention. The lymphocyte thus isolated can be established as a cell line by a known method. That is, as one aspect of the present invention, a method of producing a lymphocyte comprising a step of a process for producing a cell population containing the lymphocyte of the present invention and a step of isolating the lymphocyte from the obtained cell population is provided.

The lymphocytes obtained by the present invention can also be used for, for example, research on lymphocytes, drug screening for various diseases, evaluation of efficacy and safety of drug candidate compounds and the like. According to the present invention, because many lymphocytes can be obtained by a single operation, unlike conventional methods, it is possible to obtain reproducible research results without being influenced by differences between lots of cells.

The present invention provides lymphocytes for use in medicines, and lymphocytes for use in manufacture of pharmaceutical compositions. The lymphocyte is a cell population produced by the present invention. A pharmaceutical composition containing the lymphocyte is suitable for use in immunotherapy. For example, the lymphocyte produced by the present invention as an active ingredient can be formulated into an infusion or an injection by optionally mixing it with other ingredients (known organic or inorganic carriers suitable for parenteral administration, activators, stabilizers, etc.). The content of the cell population of the present invention in the therapeutic agent, the dose of the therapeutic agent, and various conditions regarding the use of the therapeutic agent can be appropriately determined according to known immunotherapy. Furthermore, immunotherapy with the therapeutic agent may be used in combination with drug therapy comprising administration of a known drug, radiation therapy, or surgical operation.

Examples of diseases for which administration of the cell population is effective include, but not limited to, cancer, leukemia, malignant tumor, hepatitis, and infectious diseases (for example, influenza, tuberculosis, human immunodeficiency virus infection, AIDS, MRSA infection, VRE infection, and deep-seated mycosis). The administration of the cell population is particularly useful for the treatment of HIV infection caused by HIV infecting CD4-positive T cells and AIDS (acquired immunodeficiency syndrome). Further, the lymphocyte produced by the method of the present invention can be used in combination with prevention of infectious diseases in an immunodeficiency state after bone marrow transplant, irradiation or the like, or the conventional therapy such as donor lymphocyte infusion for the purpose of remission of relapsed leukemia, anti-cancer drug treatment, radiation therapy, antibody therapy, hyperthermia therapy, or other immunotherapy. Further, it is also possible to introduce a desired foreign gene into the lymphocytes, and thereby produce lymphocytes useful for the treatment or prevention of various diseases which exhibit an effect due to the expression of the foreign gene.

EXAMPLES

The present invention is described more specifically by the following Examples, to which the scope of the present invention is not limited.

Example 1: Preparation of FCH-296

An FCH-296 polypeptide having a His-tag composed of a methionine residue and 6 histidine residues at the N-terminus (SEQ ID NO: 20) was prepared by the following procedure.

A DNA encoding the polypeptide was artificially synthesized and incorporated into an expression plasmid. *Escherichia coli* was transformed with the plasmid, and the resulting transformant was cultured under the conditions that allowed the expression of the polypeptide. The microbial cells collected from the culture were disrupted with an ultrasonic crusher (manufactured by KUBOTA Corporation) to obtain a cell-free extract. Using the extract as a starting material, FCH-296 was purified by a series of column chromatography of Ni-Chelating Sepharose (manufactured by GE Healthcare), Hydroxyapatite (40 μm, manufactured by Bio-Rad Laboratories, Inc.) and SP-Sepharose (manufactured by GE Healthcare). Confirmation of FCH-296 in the purification process was carried out by SDS-PAGE/CBB staining. The buffer of the obtained sample was replaced with a buffer [0.2 g/L KCl, 0.2 g/L $KH_2PO_4$, 8 g/L NaCl, 1.15 g/L $Na_2HPO_4$] to obtain 6 mL of an FCH-296 sample.

The FCH-296 sample showed a single band with SDS-PAGE/CBB staining. The protein concentration of the FCH-296 sample was 1.21 mg/mL (12.4 μM calculated from the molecular weight) as measured by using a BCA protein quantification kit (manufactured by Pierce).

Example 2: Coating with Anti-Human CD3 Antibody and FCH-296

On a culture device to be used in Examples described later, an anti-human CD3 antibody (OKT3, manufactured by TAKARA BIO INC.) and the FCH-296 with His-tag prepared in Example 1 were immobilized. The immobilization was carried out by adding 0.4 mL/well of D-PBS (C-40232; manufactured by PromoCell .GmbH) containing the anti-human CD3 antibody at a final concentration of 5 μg/mL and the FCH-296 with His-tag at a final concentration of 25 μg/mL to a 24-well cell culture plate (manufactured by Falcon), and then allowing the plate to stand still at 37° C. in a 5% $CO_2$ incubator for 5 hours or more. Immediately before use, a solution was removed from the immobilized plate, and the plate washed twice with 0.5 mL/well of D-PBS. As a control, a plate coated with D-PBS containing CH-296 (RetroNectin: manufactured by TAKARA BIO INC.) at a final concentration of μg/mL and the anti-human CD3 antibody at a final concentration of 5 μg/mL was prepared in the same way. As a negative control, an uncoated plate was used.

Example 3: Culture of Lymphocyte (TC0033)

(1) Expansion Culture of Cell Population

Human peripheral blood mononuclear cells (PBMC) were prepared from a human healthy donor (TC0033) from whom informed consent was obtained according to a conventional method, and then suspended at $1\times10^5$ cells/mL in a GT-T551 medium (manufactured by TAKARA BIO INC.; hereinafter referred to as GT-T551CM) containing IL-2 (Proleukin, manufactured by Nipro) at a final concentration of 200 IU/mL. The cells were seeded at $2.8\times10^5$ cells/well on the plate (N=2) and cultured at 37° C. and 5% $CO_2$ (day 0).

The cells were subcultured on day 4 and day 7. On day 4, 2.612 mL/well of GT-T551CM and 0.358 mL/well of the cell suspension were mixed in an uncoated 12-well cell culture plate (manufactured by Corning), and the culture was continued. On day 7, 1.485 mL/well of GT-T551CM and 1.485 mL/well of the cell suspension were mixed in an uncoated 12-well cell culture plate, and the culture was continued. The number of the cells in each test group was counted by trypan blue staining on day 4 and day 7 which were the days when the cells were subcultured, and on day 10 which was the day when the culture was terminated. Table 1 shows the number of the cells on day 4, day 7 and day 10, relative to the number of the cells on day 0.

TABLE 1

| Donor | Coating | Day 0 | Day 4 | Day 7 | Day 10 |
|---|---|---|---|---|---|
| TC0033 | None (negative control) | 1 | 1.8 | 49 | 193 |
| | CH-296 | 1 | 1.7 | 54 | 249 |
| | FCH-296 | 1 | 5.2 | 192 | 594 |

As compared to the negative control and the plate coated with CH-296, a high cell proliferation rate was found on the plate coated with FCH-296.

(2) Analysis of Cell Surface Marker

The cell population on day 10 obtained in Example 3-(1) was washed with PBS containing 0.1% bovine serum albumin (manufactured by SIGMA) (hereinafter, referred to as 0.1% BSA/PBS). The cell population was suspended in 0.1% BSA/PBS, and reacted with an antibody cocktail of an FITC-labeled mouse anti-human CD8 antibody, an RD-1 labeled mouse anti-human CD4 antibody and a PC-5 labeled mouse anti-human CD3 antibody (manufactured by Beckman Coulter, Inc.). Then, the cell population was washed twice with 0.1% BSA/PBS, and suspended again in 0.1% BSA/PBS. The cell population thus obtained was subjected to flow cytometry (FC-500, manufactured by Beckman Coulter, Inc.), and a proportion of CD3-positive and CD4-positive cells (CD3+ CD4+) in each cell population was calculated. Results of the cell surface marker measurement are shown in Table 2. The proportion of CD3-positive cells in all the cells was 94% or more in all test groups.

TABLE 2

| Donor | Coating | CD3+CD4+ |
|---|---|---|
| TC0033 | None (negative control) | 31.6% |
|  | CH-296 | 29.7% |
|  | FCH-296 | 47.4% |

As compared to the negative control and the plate coated with CH-296, a high proportion of CD3+CD4+ was found on the plate coated with FCH-296. Generally, CD3+CD4+ represents helper T cells. From the results of Table 1 and Table 2, it was shown that helper T cells efficiently proliferate on a plate coated with FCH-296.

Example 4: Culture of Lymphocyte from Plural Donors (TC0033 and TC0071)

(1) Expansion Culture of Cell Population

PBMC was prepared from the same human healthy donor (TC0033) as in Example 3 and a different human healthy donor (TC0071), and then cultured in the same manner as in Example 3-(1). Table 3 shows the number of the cells on day 4, day 7 and day 10, relative to the number of the cells on day 0.

TABLE 3

| Donor | Coating | Day 0 | Day 4 | Day 7 | Day 10 |
|---|---|---|---|---|---|
| TC0033 | None (negative control) | 1 | 1.1 | 10.1 | 99.7 |
|  | CH-296 | 1 | 2.2 | 76.1 | 501 |
|  | FCH-296 | 1 | 3.1 | 74.9 | 629 |
| TC0071 | None (negative control) | 1 | 2.0 | 13.7 | 71.2 |
|  | CH-296 | 1 | 4.0 | 126 | 623 |
|  | FCH-296 | 1 | 4.5 | 146 | 685 |

In the both cases of donors TC0033 and TC0071, high cell proliferation rates were found on the plates coated with FCH-296.

(2) Analysis of Cell Surface Marker

The cell surface markers of the cell populations on day 10 obtained in Example 4-(1) were measured in the same manner as in Example 3-(2). Results are shown in Table 4. The proportion of CD3-positive cells in all the cells was 94% or more in all test groups.

TABLE 4

| Donor | Coating | CD3+CD4+ |
|---|---|---|
| TC0033 | None (negative control) | 39.4% |
|  | CH-296 | 37.3% |
|  | FCH-296 | 57.5% |
| TC0071 | None (negative control) | 13.4% |
|  | CH-296 | 20.5% |
|  | FCH-296 | 26.1% |

In the both cases of donors TC0033 and TC0071, high proportions of CD3+CD4+ were found on the plates coated with FCH-296. Generally, CD3+CD4+ represents helper T cells. From the results of Table 3 and Table 4, it was shown that helper T cells efficiently proliferate on a plate coated with FCH-296 regardless of donor.

Example 5: Measurement of Proportion of CD45RA-Positive and CCR7-Positive Cell (Naive Cell)

(1) Expansion Culture of Cell Population

PBMC prepared from human healthy donors (TC0033 and TC0071) was suspended at $1\times10^5$ cells/mL in GT-T551CM containing IL-2 at a final concentration of 200 IU/mL. The cells were seeded at $2.8\times10^5$ cells/well on a plate (N=2) and then cultured at 37° C. and 5% $CO_2$ (day 0). For culture from day 0 to day 4, a plate coated with an anti-human CD3 antibody, and an FCH-296 polypeptide (with His-tag, SEQ ID NO: 20) or an FCH-296 polypeptide having insertion of 9 amino acids at the N-terminus (SEQ ID NO: 31) was used. The cells were subcultured on day 4 and day 7. On day 4, 2.612 mL/well of GT-T551CM and 0.358 mL/well of the cell suspension were mixed in an uncoated 12-well cell culture plate, and the culture was continued. On day 7, 1.485 mL/well of GT-T551CM and 1.485 mL/well of the cell suspension were mixed in an uncoated 12-well cell culture plate, and the culture was continued. As a negative control, an uncoated plate was used from day 0 of culture. The FCH-296 polypeptide having insertion of 9 amino acids at the N-terminus was prepared by a conventional method using an ordinary column such as SP Sepharose (registered trademark) Fast Flow (manufactured by GE Healthcare).

(2) Analysis of Cell Surface Marker

The cell surface markers of the cell populations on day 10 were measured in the same manner as in Example 3-(2). Results are shown in Table 5. The proportion of CD3-positive cells in all the cells was 94% or more in all test groups.

TABLE 5

| Donor | Coating | CD3+CD4+ |
|---|---|---|
| TC0033 | None (negative control) | 18.0% |
|  | FCH-296 | 46.4% |
|  | N-terminal 9 a.a. insertion of FCH-296 | 48.6% |
| TC0071 | None (negative control) | 16.7% |
|  | FCH-296 | 24.5% |
|  | N-terminal 9 a.a. insertion of FCH-296 | 23.1% |

In the both cases of donors TC0033 and TC0071, high proportions of CD3+CD4+ were found on the plates coated with the FCH-296 polypeptide or the FCH-296 polypeptide having insertion of 9 amino acids at the N-terminus ("N-terminal 9 a.a. insertion of FCH-296" in Table 5).

(3) Analysis of Naive Cell Proportion

The cell population on day 10 obtained in Example 5-(1) was washed with PBS containing 0.1% bovine serum albumin (manufactured by SIGMA) (hereinafter, referred to as 0.1% BSA/PBS). The cell population was suspended in 0.1% BSA/PBS, and reacted with an RD-1 labeled IgG1 mouse anti-human 2H4 (CD45RA) antibody (manufactured by Beckman Coulter, Inc.) and an FITC-labeled IgG2A mouse anti-human CCR7 antibody (manufactured by R & D). Then, the cell population was washed twice with 0.1% BSA/PBS, and suspended again in 0.1% BSA/PBS. The cell population thus obtained was subjected to flow cytometry, and a proportion of naive cells (CD45RA+CCR7+) in each cell population was calculated. Measurement results are shown in FIG. 2.

In the both cases of donors TC0033 and TC0071, high proportions of naive cells (CD45RA+ CCR7+) were found on the plates coated with FCH-296 or "N-terminal 9 a.a. insertion of FCH-296".

Example 6: Evaluation of FCH-296 Having Various N-Terminal Sequences

A variety of FCH-296 having various N-terminal sequences was prepared. That is, FCH-296 having deletion of N-terminal 9 amino acids (SEQ ID NO: 25), FCH-296 having deletion of N-terminal 6 amino acids (SEQ ID NO: 26), FCH-296 having deletion of N-terminal 5 amino acids (SEQ ID NO: 27), FCH-296 having deletion of N-terminal 3 amino acids (SEQ ID NO: 28), FCH-296 (SEQ ID NO: 19), FCH-296 having insertion of N-terminal 3 amino acids (SEQ ID NO: 29), FCH-296 having insertion of N-terminal 6 amino acids (SEQ ID NO: 30), FCH-296 having insertion of N-terminal 11 amino acids (SEQ ID NO: 32), FCH-296 having insertion of N-terminal 12 amino acids (SEQ ID NO: 33), FCH-296 having insertion of N-terminal 14 amino acids (SEQ ID NO: 34), FCH-296 having insertion of N-terminal 15 amino acids (SEQ ID NO: 35), FCH-296 having insertion of N-terminal HKRHEEGH (SEQ ID NO: 36), FCH-296 having insertion of N-terminal HKRH (SEQ ID NO: 37), FCH-296 having insertion of N-terminal HH (SEQ ID NO: 38), and FCH-296 having insertion of N-terminal HHH (SEQ ID NO: 39) were prepared.

Using the above-described FCH-296 having various N-terminal sequences instead of FCH-296 (with His-tag, SEQ ID NO: 20) and FCH-296 having insertion of N-terminal 9 amino acids (SEQ ID NO: 31), the experiments described in Examples 2 to 5 are carried out. The FCH-296 having various N-terminal sequences has the same effect as FCH-296 (with His-tag, SEQ ID NO: 20) and FCH-296 having insertion of N-terminal 9 amino acids (SEQ ID NO: 31).

Industrial Applicability

According to the present invention, a method of producing a large amount of lymphocytes in a short period of time is provided.

SEQUENCE LISTING FREE TEXT

SEQ ID NO:1; Partial region of fibronectin named III-1
SEQ ID NO:2; Partial region of fibronectin named III-2
SEQ ID NO:3; Partial region of fibronectin named III-3
SEQ ID NO:4; Partial region of fibronectin named III-4
SEQ ID NO:5; Partial region of fibronectin named III-5
SEQ ID NO:6; Partial region of fibronectin named III-6
SEQ ID NO:7; Partial region of fibronectin named III-7
SEQ ID NO:8; Partial region of fibronectin named III-8
SEQ ID NO:9; Partial region of fibronectin named III-9
SEQ ID NO:10; Partial region of fibronectin named III-10
SEQ ID NO:11; Partial region of fibronectin named III-11
SEQ ID NO:12; Partial region of fibronectin named III-12
SEQ ID NO:13; Partial region of fibronectin named III-13
SEQ ID NO:14; Partial region of fibronectin named III-14
SEQ ID NO:15; Partial region of fibronectin named CS-1
SEQ ID NO:16; Fibronectin fragment named 120k-fr
SEQ ID NO:17; Fibronectin fragment named CH-271
SEQ ID NO:18 Fibronectin fragment named CH-296 (RetroNectin)
SEQ ID NO:19; Fibronectin fragment named FCH-296
SEQ ID NO:20; His-tag FCH-296
SEQ ID NO:21; N-terminal 9a.a. deletion of III-1
SEQ ID NO:22; N-terminal 6a.a. deletion of III-1
SEQ ID NO:23; N-terminal 5a.a. deletion of III-1
SEQ ID NO:24; N-terminal 3a.a. deletion of III-1
SEQ ID NO:25; N-terminal 9a.a. deletion of FCH-296
SEQ ID NO:26; N-terminal 6a.a. deletion of FCH-296
SEQ ID NO:27; N-terminal 5a.a. deletion of FCH-296
SEQ ID NO:28; N-terminal 3a.a. deletion of FCH-296
SEQ ID NO:29; N-terminal 3a.a. insertion of FCH-296
SEQ ID NO:30; N-terminal 6a.a. insertion of FCH-296
SEQ ID NO:31; N-terminal 9a.a. insertion of FCH-296
SEQ ID NO:32; N-terminal 11a.a. insertion of FCH-296
SEQ ID NO:33; N-terminal 12a.a. insertion of FCH-296
SEQ ID NO:34; N-terminal 14a.a. insertion of FCH-296
SEQ ID NO:35; N-terminal 15a.a. insertion of FCH-296
SEQ ID NO:36; N-terminal HKRHEEGH insertion of FCH-296
SEQ ID NO:37; N-terminal HKRH insertion of FCH-296
SEQ ID NO:38; N-terminal HH insertion of FCH-296
SEQ ID NO:39; N-terminal HHH insertion of FCH-296

The invention claimed is:

1. A method of producing a lymphocyte, the method comprising a step of culturing a lymphocyte in the presence of:
(a) a recombinant polypeptide comprising human fibronectin III repeats 1-3;
(b) a recombinant polypeptide comprising human fibronectin III repeats 8-10; and
(c) a recombinant polypeptide comprising human fibronectin III repeats 12-14 wherein the recombinant polypeptides of (a), (b) and (c) are not full-length human fibronectin, and wherein the lymphocytes produced by the method have a higher proportion of CD4-expressing cells than those obtained by culturing in the absence of the recombinant polypeptides of (a), (b) and (c).

2. The method according to claim 1, wherein the lymphocyte is cultured in the presence of a recombinant polypeptide containing the recombinant polypeptides (a), (b) and (c) within the same molecule, wherein the recombinant polypeptide is not full-length human fibronectin.

3. The method according to claim 2, wherein the recombinant polypeptide is a recombinant polypeptide comprising the amino acid sequence set forth in SEQ ID NO: 19.

4. The method according to claim 2, wherein the recombinant polypeptide is a recombinant polypeptide comprising the amino acid sequence set forth in SEQ ID NO: 31.

5. The method according to claim 1, wherein the lymphocyte is cultured in the presence of the recombinant polypeptides (a)-(c) and an anti-CD3 antibody.

6. The method according to claim 1, wherein the step of culturing a lymphocyte in the presence of the recombinant polypeptides is performed in a state where a solid phase coated with the recombinant polypeptides is in contact with the lymphocyte.

7. The method according to claim 6, wherein the solid phase is a cell culture device or a cell culture carrier.

8. The method according to claim 6, wherein the solid phase is a dish, plate, flask, bag, bead, membrane or glass slide.

9. The method according to claim 1, wherein the lymphocyte is a human-derived lymphocyte.

10. The method according to claim 1, wherein a population of peripheral blood mononuclear cells (PBMC) as the lymphocyte is cultured.

* * * * *